(12) United States Patent
Tveito et al.

(10) Patent No.: US 11,846,631 B2
(45) Date of Patent: Dec. 19, 2023

(54) METHODS FOR DETERMINING DRUG EFFECTS ON A MATURE CARDIOMYOCYTE

(71) Applicant: ORGANOS, INC., Berkeley, CA (US)

(72) Inventors: Aslak Tveito, Lysaker (NO); Samuel Wall, Lysaker (NO); Karoline Horgmo Jaeger, Lysaker (NO)

(73) Assignee: ORGANOS, INC., Berkeley, CA (US)

( * ) Notice: Subject to any disclaimer, the term of this patent is extended or adjusted under 35 U.S.C. 154(b) by 677 days.

(21) Appl. No.: 16/265,849

(22) Filed: Feb. 1, 2019

(65) Prior Publication Data

US 2019/0242879 A1 Aug. 8, 2019

Related U.S. Application Data

(60) Provisional application No. 62/625,621, filed on Feb. 2, 2018.

(51) Int. Cl.
| | | |
|---|---|---|
| *C12N 5/077* | (2010.01) | |
| *G01N 33/50* | (2006.01) | |
| *G16B 5/20* | (2019.01) | |
| *G16H 50/50* | (2018.01) | |
| *G01N 33/52* | (2006.01) | |
| *G01N 33/68* | (2006.01) | |

(52) U.S. Cl.
CPC ....... *G01N 33/5061* (2013.01); *C12N 5/0657* (2013.01); *G01N 33/5026* (2013.01); *G01N 33/52* (2013.01); *G01N 33/6872* (2013.01); *G16B 5/20* (2019.02); *G16H 50/50* (2018.01); *G01N 2458/30* (2013.01); *G01N 2500/10* (2013.01)

(58) Field of Classification Search
CPC .......... G01N 33/5061; G01N 33/5026; G01N 2500/10; C12N 5/05657; C12N 5/0657; G16H 50/50
See application file for complete search history.

(56) References Cited

U.S. PATENT DOCUMENTS

| | | |
|---|---|---|
| 2013/0096888 A1 | 4/2013 | Hickman et al. |
| 2016/0266144 A1 | 9/2016 | Kralj et al. |

OTHER PUBLICATIONS

Bedut et al. High-Throughput Drug Profiling With Voltage- and Calcium-Sensitive Fluorecent Probes in Human IPSC-Derived Cardiomyocytes; American Journal of Physiology Hear and Circulatory Physiology, vol. 311, pp. H44-H53. (Year: 2016).*

Shinnawi et al. Monitoring Human-Induced Pluripotent Stem-Cell-Derived Cardiomyocytes With Genetically Encoded Calcium and Voltage Fluorescent Reporters; Stem Cell Reports, vol. 5, No. 4, pp. 582-596. (Year: 2015).*

Ma et al., "High Purity Human-Induced Pluripotent Stem Cell-Derived Cardiomyocytes: Electrophysiological Properties of Action Potentials and Ionic Currents", American Journal of Physiology, vol. 301, No. 5, Nov. 1, 2011, pp. H2006-H2017.

Paci et al., "Computational Models of Ventricular- and Atrial-Like Human Induced Pluripotent Stem Cell Derived Cardiomyocytes", Annals of Biomedical Engineering, vol. 41, No. 11, May 31, 2013, pp. 2334-2348.

Paci et al., "Human Induced Pluripotent Stem Cell-Derived Versus Adult Cardiomyocytes: an in Silico Electrophysiological Study on Effects of Ionic Current Block", British Journal of Pharmacology, vol. 172, No. 21, Nov. 1, 2015, pp. 5147-5160.

International Patent Application No. PCT/IB2019/050840 , "International Preliminary Report on Patentability", dated Aug. 13, 2020, 13 pages.

International Patent Application No. PCT/IB2019/050840 , "International Search Report and Written Opinion", dated May 7, 2019, 18 pages.

et al., "Integrating Cardiomyocytes from Human Pluripotent Stem Cells in Safety Pharmacology: Has the Time Come?", British Journal of Pharmacology, vol. 174, No. 21, Nov. 1, 2017, pp. 3749-3765.

Tveito et al., "Inversion and Computational Maturation of Drug Response Using human Stem Cell Derived Cardiomyocytes in Microphysiological Systems", Scientific Reports, vol. 8, No. 1, Dec. 1, 2018, 14 pages.

* cited by examiner

*Primary Examiner* — Jeanette M Lieb
*Assistant Examiner* — Paul C Martin
(74) *Attorney, Agent, or Firm* — KILPATRICK TOWNSEND & STOCKTON LLP

(57) ABSTRACT

The present invention provides a method for determining the effect of a drug on a mature cardiomyocyte. In some embodiments, the method comprises using transmembrane voltage and/or intracellular calcium data obtained from control immature cardiomyocytes and those that have been contacted with the drug to parameterize models of immature cardiomyocytes, then applying a maturation matrix to generate a mature cardiomyocyte model. The method is useful for, among other things, predicting whether a drug may have proarrhythmic properties and for determining whether a particular drug should be administered to a patient.

25 Claims, 21 Drawing Sheets

FIG. 6A

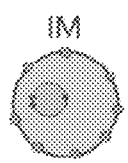

- Membrane protein (type 1)
- Membrane protein (type 2)
- SR release protein
- SR uptake protein In the IM state, the cell membrane is populated by a certain number of proteins of different types. The intracellular space contains the sarcoplasmic reticulum (SR) equipped with specialized proteins for release and uptake of calcium.

FIG. 6B

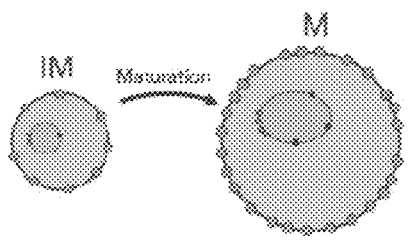

As the cell evolves from the IM to the M state, the number of proteins, the membrane area and the cell volume increase. Each specific type of protein may increase at different rates.

FIG. 6C

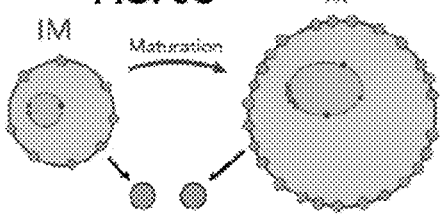

Individual proteins are functionally invariant during maturation.

FIG. 6D

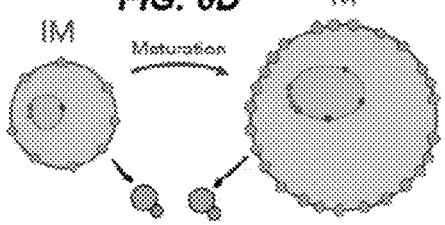

A drug affects individual proteins of an IM cell in exactly the same manner as for an M cell.

FIG. 6E

METHODS FOR DETERMINING DRUG EFFECTS ON A MATURE CARDIOMYOCYTE

CROSS-REFERENCES TO OTHER APPLICATIONS

This application claims priority to U.S. Provisional Patent Application No. 62/625,621, entitled "METHODS FOR DETERMINING DRUG EFFECTS" filed on Feb. 2, 2018, which is hereby incorporated by reference in its entirety for all purposes.

BACKGROUND OF THE INVENTION

The discovery of human induced pluripotent stem cells (hiPSCs) has started a new era in biological science and medicine. These reprogrammed somatic cells can be differentiated into a wide variety of cell lineages, and allow in vitro examination of cellular properties at the level of the human individual. In particular, this technology has large implications in drug development, moving us away from well-studied but often unrepresentative animal models towards direct testing of compounds in specific human phenotypes and genotypes. This new access offers the potential for creating better, safer drug treatments; both from the ability to target precision, patient-specific approaches, and to reveal possible side effects of drugs in the broader human population. However, despite its promise, the technology needed to fully utilize hiPSCs for drug testing is still under development and currently faces many difficulties limiting practical applicability.

In particular, the problem of maturation is a major challenge to the successful use of hiPSCs. Although hiPSCs can be used to create specialized human cells and tissues, these rapidly grown cells and tissues may have significant proteomic and structural differences to, and are often more fetal-like than, their adult in vivo counterpart. This is especially true in hiPSC derived cardiomyocytes (hiPSC-CMs), where the adult cells they are intended to represent have undergone decades of growth and development under cyclical physiological loading and stimulation. However, despite this limitation, hiPSC-CMs have already been successfully used to assess unwanted side effects of drugs (see, e.g., [1, 2] in Example 1), and new technologies such as microphysiological systems (MPSs) (see, e.g., [3] in Example 1) are emerging to improve maturation and better capture drug effects. Still, the overall applicability of hiPSC-CMs to find unwanted side effects of drugs for adult cardiomyocytes remains limited by the fact that only relatively immature cells are available for analysis (see, e.g., [4, 5, 6, 7] in Example 1). And, as pointed out in numerous papers (see, e.g., [8, 9, 10, 11, 12] in Example 1), the electrophysiological characteristics of hiPSC-CMs and adult cardiomyocytes differ significantly and, for determining potential dangerous drug side-effects, these differences may lead to both false positives and false negatives (see, e.g., [13, 3] in Example 1). Thus, there remains a need for new methods to utilize immature CMs for drug screening. The present invention satisfies this need, and provides related advantages as well.

BRIEF SUMMARY OF THE INVENTION

In one aspect, the present invention provides a method for determining an effect of a drug on a mature cardiomyocyte (CM). In some embodiments, the method comprises:

(a) obtaining one or more first measurements of transmembrane voltage ($V_m$) and/or one or more first measurements of intracellular calcium concentration ($Ca_i$) in a control immature CM;

(b) storing data representing said one or more first measurements of $V_m$ in vector $v^c$ and/or storing data representing said one or more first measurements of $Ca_i$ in vector $c^C$;

(c) contacting the immature CM with a composition comprising a sufficient amount of the drug to produce a drug-treated immature CM;

(d) obtaining one or more second measurements of $V_m$ and/or one or more second measurements of $Ca_i$ in the drug-treated immature CM;

(e) storing data representing said one or more second measurements of $V_m$ in vector $v^D$ and/or storing data representing said one or more second measurements of $Ca_i$ in vector $c^D$;

(f) inverting the data stored in $v^C$ and/or $c^C$ to update the value of one or more parameters in an immature base CM model, stored in vector $p^{IM,B}$, to yield vector $p^{IM,C}$ that parameterizes an immature control CM model;

(g) inverting the data stored in $v^D$ and/or $c^D$ to update the value of one or more parameters stored in vectore $p^{IM,C}$ to yield vector $p^{IM,D}$ that parameterizes an immature drug-treated CM model;

(h) updating one or more values in a diagonal maturation matrix $Q$ such that the equality $Qp^{IM,C}=p^M$ is satisfied, wherein $p^M$ is a vector that parameterizes a mature base CM model and wherein before $Q$ is updated, $Q$ satisfies the equality $p^M=Qp^{IM,B}$;

(i) multiplying $P^{IM,D}$ by $Q$ to generate vector $p^{M,D}$, wherein $p^{M,D}$ parameterizes a mature drug-treated CM model;

(j) using the mature base and drug-treated CM models to generate a simulated mature control action potential (AP) and a simulated mature drug-treated AP, respectively; and (k) comparing one or more morphological properties of the simulated mature control AP and the simulated mature drug-treated AP in order to calculate a difference, thereby determining the effect of the drug.

In some embodiments, the one or more parameters represent the number of one or more proteins in the CM model, the dynamics of one or more proteins in the CM model, cell volume in the CM model, cell surface area in the CM model, cell membrane capacitance in the CM model, or a combination thereof. In some instances, the one or more proteins are selected from the group consisting of an ion channel, an ion exchanger, an ion pump, and a combination thereof. In some embodiments, the one or more parameters represent the maximum conductance of an ion channel or the maximum rate of an ion exchanger or ion pump. In some instances, the ion channel is a potassium channel, a calcium channel, or a sodium channel.

In some embodiments, inverting the data comprises minimizing a cost function. In particular embodiments, minimizing the cost function comprises minimizing the differences between a characteristic determined in an experimentally-observed AP or calcium transient and the corresponding characteristic in an AP or calcium transient generated by the immature base CM model or the immature control CM model; wherein the characteristic is selected from the group consisting of $V_m$, $APD_{V,n}$, $APD_{Ca,n}$, maximum upstroke velocity of the calcium concentration, and a combination thereof; and wherein $APD_{V,n}$ and $APD_{Ca,n}$, are the duration of the $V_m$ action potential and calcium transients, respectively, wherein each value of n is independently selected and represents a percentage of the maximum $V_m$ value. In some instances, each value of n is independently selected from the group consisting of 30, 50, and 80.

In some embodiments, the cost function is iteratively minimized. In some instances, between 2 and 100 iterations are used. In some embodiments, during each iteration, between 1,000 and 5,000 values for each parameter being updated are randomly selected from within an interval of allowed values. In some embodiments, during each iteration, the length of an interval of allowed values for a parameter being updated is decreased by 90%.

In some embodiments, when $v^D$ or $c^D$ are inverted, the simulated drug effect is that of reducing the maximum conductance of an ion channel or the maximum rate of an ion pump or ion exchanger. In some embodiments, only $v^C$ and $v^D$ are inverted. In other embodiments, only $c^C$ and $c^D$ are inverted. In still other embodiments, $v^C$, $c^C$, $v^D$, and $c^D$ are inverted.

In some embodiments, multiplying a vector p by $Q$ changes the number of one or more proteins, the cell volume, and/or the cell surface area in the CM model that is parameterized by p. In some embodiments, the immature CM is an induced pluripotent stem cell-derived cardiomyocyte (iPSC-CM).

In some embodiments, the immature control and drug-treated CMs are different CMs. In other embodiments, the immature control and drug-treated CMs are the same CM. In some embodiments, the composition is contacted with the CM for at least about 15 minutes before the one or more second measurements of $V_m$ and/or the one or more second measurements of $Ca_i$ are obtained. In some embodiments, the drug is a calcium channel blocker, a potassium channel blocker, a sodium channel blocker, or a combination thereof. In some embodiments, the effects of two or more drugs are determined.

In some embodiments, a fluorescent indicator or dye is used to measure $V_m$ and/or $Ca_i$. In some instances, the fluorescent indicator or dye comprises Berkeley Red Sensor of Transmembrane Potential (BeRST1) and/or GCaMP. In some embodiments, at least about 100 $V_m$ and/or $Ca_i$ measurements are made per second. In particular embodiments, between about 100 and about 3,000 $V_m$ and/or $Ca_i$ measurements are made per second. In some embodiments, the $V_m$ and/or $Ca_i$ measurements are made for at least about 1 second. In particular embodiments, the $V_m$ and/or $Ca_i$ measurements are made for between about 1 second and about 30 minutes.

In some embodiments, the one or more morphological properties are selected from the group consisting of $APD_{V,n}$, $APD_{Ca,n}$, maximum $V_m$ upstroke velocity ($(dv/dt)_{max}$), resting membrane potential, maximum $Ca_i$ upstroke velocity ($(dc/dt)_{max}$), peak $Ca_i$, and a combination thereof wherein $APD_{V,n}$ and $APD_{Ca,n}$, are the duration of the $V_m$ action potential and calcium transients, respectively; and wherein each value of n is independently selected and represents a percentage of the maximum $V_m$ value. In some instances, each value of n is independently selected from the group consisting of 30, 50, and 80.

In some embodiments, the drug is determined to have a proarrhythmic effect when at least one of the morphological properties in the simulated mature drug-treated AP is at least about 1.5-fold higher or lower compared to the corresponding morphological property in the simulated mature control AP. In particular embodiments, the drug is determined to have a proarrhythmic effect when at least one of the morphological properties in the simulated mature drug-treated AP is at least about 3-fold higher or lower compared to the corresponding morphological property in the simulated mature control AP.

In some embodiments, the immature CM is derived from a cell obtained from a subject. In particular embodiments, the subject is a patient who is to be administered the drug. In some embodiments, the subject is not administered the drug when the drug is determined to have a proarrhythmic effect.

In another aspect, the present invention provides a method for selecting a drug that does not have a proarrhythmic effect on a mature cardiomyocyte (CM). In some embodiments, the method comprises:

(a) obtaining one or more first measurements of transmembrane voltage ($V_m$) and/or one or more first measurements of intracellular calcium concentration ($Ca_i$) in a control immature CM;

(b) storing data representing said one or more first measurements of $V_m$ in vector $v^C$ and/or storing data representing said one or more first measurements of $Ca_i$ in vector $c^C$;

(c) contacting the immature CM with a composition comprising a sufficient amount of the drug to produce a drug-treated immature CM;

(d) obtaining one or more second measurements of $V_m$ and/or one or more second measurements of $Ca_i$ in the drug-treated immature CM;

(e) storing data representing said one or more second measurements of $V_m$ in vector $v^D$ and/or storing data representing said one or more second measurements of $Ca_i$ in vector $c^D$;

(f) inverting the data stored in $v^C$ and/or $c^C$ to update the value of one or more parameters in an immature base CM model, stored in vector $p^{IM,B}$, to yield vector $p^{IM,C}$ that parameterizes an immature control CM model;

(g) inverting the data stored in $v^D$ and/or $c^D$ to update the value of one or more parameters stored in vector $p^{IM,C}$ to yield vector $p^{IM,D}$ that parameterizes an immature drug-treated CM model;

(h) updating one or more values in a diagonal maturation matrix $Q$ such that the equality $Qp^{IM,C}=p^M$ is satisfied, wherein $p^M$ is a vector that parameterizes a mature base CM model and wherein before $Q$ is updated, $Q$ satisfies the equality $p^M=Qp^{IM,B}$;

(i) multiplying $p^{IM,D}$ by $Q$ to generate vector $p^{M,D}$, wherein $p^{M,D}$ parameterizes a mature drug-treated CM model;

(j) using the mature base and drug-treated CM models to generate a simulated mature control action potential (AP) and a simulated mature drug-treated AP, respectively;

(k) comparing a morphological property of the simulated mature control AP to the morphological property of the simulated mature drug-treated AP in order to calculate a difference; and (l) based upon the difference in the morphological property between the simulated mature control and drug-treated APs, determining that the drug does not have a proarrhythmic effect and selecting the drug when it does not have a proarrhythmic effect.

In some embodiments, the drug is selected for administration to a subject. In some embodiments, the immature CM is derived from a cell obtained from the subject. In some instances, the immature CM is an induced pluripotent stem cell-derived cardiomyocyte (iPSC-CM).

In some embodiments, two or more morphological properties are compared. In some embodiments, the morphological property is selected from the group consisting of $APD_{v,n}$, $APD_{Ca,n}$, maximum $V_m$ upstroke velocity $((dv/dt)_{max})$, resting membrane potential, maximum $Ca_i$ upstroke velocity $((dc/dt)_{max})$, peak $Ca_i$, and a combination thereof; wherein $APD_{v,n}$ and $APD_{Ca,n}$, are the duration of the $V_m$ action potential and calcium transients, respectively; and wherein each value of n is independently selected and represents a percentage of the maximum $V_m$ value. In some instances, each value of n is independently selected from the group consisting of 30, 50, and 80.

In some embodiments, the drug is selected when the morphological property in the simulated mature control AP is less than about 3-fold lower or higher compared to the morphological property in the simulated mature drug-treated AP. In some instances, the drug is selected when the morphological property in the simulated mature control AP is less than about 1.5-fold lower or higher compared to the morphological property in the simulated mature drug-treated AP.

In some embodiments, the one or more parameters represent the number of one or more proteins in the CM model, the dynamics of one or more proteins in the CM model, cell volume in the CM model, cell surface area in the CM model, cell membrane capacitance in the CM model, or a combination thereof. In some instances, the one or more proteins are selected from the group consisting of an ion channel, an ion exchanger, an ion pump, and a combination thereof. In some embodiments, the one or more parameters represent the maximum conductance of an ion channel or the maximum rate of an ion exchanger or ion pump. In some instances, the ion channel is a potassium channel, a calcium channel, or a sodium channel.

In some embodiments, inverting the data comprises minimizing a cost function. In particular embodiments, minimizing the cost function comprises minimizing the differences between a characteristic determined in an experimentally-observed AP or calcium transient and the corresponding characteristic in an AP or calcium transient generated by the immature base CM model or the immature control CM model; wherein the characteristic is selected from the group consisting of $V_m$, $APD_{v,n}$, $APD_{Ca,n}$, maximum upstroke velocity of the calcium concentration, and a combination thereof; and wherein $APD_{V,n}$ and $APD_{Ca,n}$, are the duration of the $V_m$ action potential and calcium transients, respectively, wherein each value of n is independently selected and represents a percentage of the maximum $V_m$ value. In some instances, each value of n is independently selected from the group consisting of 30, 50, and 80.

In some embodiments, the cost function is iteratively minimized. In some instances, between 2 and 100 iterations are used. In some embodiments, during each iteration, between 1,000 and 5,000 values for each parameter being updated are randomly selected from within an interval of allowed values. In some embodiments, during each iteration, the length of an interval of allowed values for a parameter being updated is decreased by 90%.

In some embodiments, when $v^D$ or $c^D$ are inverted, the simulated drug effect is that of reducing the maximum conductance of an ion channel or the maximum rate of an ion pump or ion exchanger. In some embodiments, only $v^C$ and $v^D$ are inverted. In other embodiments, only $c^C$ and $c^D$ are inverted. In still other embodiments, $v^C$, $c^C$, $v^D$, and $c^D$ are inverted.

In some embodiments, multiplying a vector p by Q changes the number of one or more proteins, the cell volume, and/or the cell surface area in the CM model that is parameterized by p. In some embodiments, the immature control and drug-treated CMs are different CMs. In other embodiments, the immature control and drug-treated CMs are the same CM. In some embodiments, the composition is contacted with the CM for at least about 15 minutes before the one or more second measurements of $V_m$ and/or the one or more second measurements of $Ca_i$ are obtained. In some embodiments, the drug is a calcium channel blocker, a potassium channel blocker, a sodium channel blocker, or a combination thereof. In some embodiments, two or more drugs are selected.

In some embodiments, a fluorescent indicator or dye is used to measure $V_m$ and/or $Ca_i$. In some instances, the fluorescent indicator or dye comprises Berkeley Red Sensor of Transmembrane Potential (BeRST1) and/or GCaMP. In some embodiments, at least about 100 $V_m$ and/or $Ca_i$ measurements are made per second. In particular embodiments, between about 100 and about 3,000 $V_m$ and/or $Ca_i$ measurements are made per second. In some embodiments, the $V_m$ and/or $Ca_i$ measurements are made for at least about 1 second. In particular embodiments, the $V_m$ and/or $Ca_i$ measurements are made for between about 1 second and about 30 minutes.

Other objects, features, and advantages of the present invention will be apparent to one of skill in the art from the following detailed description and figures.

BRIEF DESCRIPTION OF THE DRAWINGS

FIGS. 6A-6E show an illustration of the assumptions underlying the model of maturation. FIG. 6A depicts the immature cell with two types of membrane proteins, with a cytosolic space containing the sarcoplasmic reticulum with associated release and uptake proteins. FIG. 6B depicts the concept that maturation is multiplication in the sense that the number of proteins increases at a protein-specific rate. FIG. 6C depicts that a specific protein in the IM cell is the same as in the M cell. FIG. 6D depicts that a drug affects every single protein in the IM cell in exactly the same manner as for the M cell. FIG. 6E shows a model of the transmembrane potential for IM and M cells, and the relation between these models; and how these models are affected when a drug is applied.

DETAILED DESCRIPTION OF THE INVENTION

I. Introduction

Figure 1:
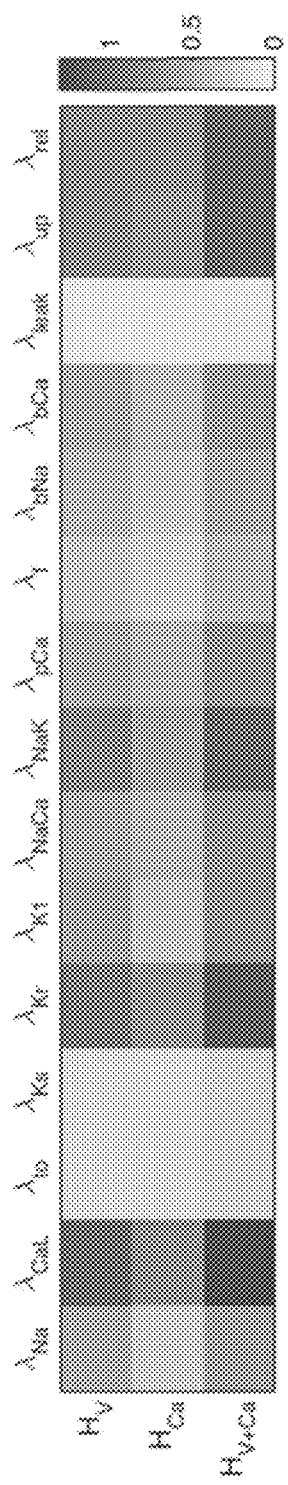
FIG. 1 shows the sensitivity of maximum conductances of the immature base model assessed by the three cost functions defined in equations (7)(8) in Example 1 (or equations (3)-(4) in Example 2) with ε=0.2. The intensities correspond to the sum of perturbing the maximum conductance of one single current (or flux) by +/−10%.

The present invention relates to how computational models of immature (IM) and mature (M) cardiomyocytes can contribute to the improvement of the applicability of using hiPSC-CMs for drug screening. Despite remarkable progress in handling hiPSC-CMs under lab conditions (see, e.g., [14] in Example 1), the ability to create fully mature hiPSC-CMs for drug screening is likely to remain a significant challenge. As described herein, computational modeling (in silico analysis) can be used to deduce properties of mature (adult) cardiomyocytes based on measurements of their immature counterpart. In silico investigation of the properties of the action potential (AP) of excitable cells is a well-developed field (see, e.g., [15, 16, 17] in Example 1) and includes models of human cardiomyocytes (see, e.g., [18, 19, 20, 21] in Example 1) and models where the effect of drugs are taken into account (see e.g., [22, 23, 24] in Example 1). Also, mathematical models of the action potential of hiPSC-CMs have been developed (see, e.g., [9, 25] in Example 1) based on measurements reported previously (see, e.g., [8, 26, 27, 28] in Example 1). This field has progressed to the point where computational models are now an active part of cardiotoxicity research (see, e.g., [29] in Example 1), and are being integrated into guidelines for comprehensive drug arrhythmia analysis.

A key to the present invention is the assumption that individual proteins are functionally invariant under maturation. Therefore, maturation is multiplication in the sense that, for every type of protein, the number of proteins multiply during maturation, but the function of every protein remains unaltered. In addition, the surface area of the cell and the cell volume also increase significantly during maturation, leading to large changes in current densities between the IM and M cells. The invariance of the functional properties of the IM and M versions of every protein suggests a proportionality between the associated individual currents of the IM and M cells which may explain the results obtained previously (see e.g., [12] in Example 1). The present invention is based, in part, on the discovery that the proportionality between the individual currents can be used to define a maturation matrix that maps the parameterization of a model of an IM cell to the parameterization of a model of an M cell. Furthermore, a consequence of the functional equivalence is that a Markov model that is used to represent the dynamics of a single ion channel can be used for both IM and M cells without modification.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typical, exemplary degrees of error are within 20 percent (%), preferably within 10%, and more preferably within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

As used herein the term "drug" refers to any molecule or composition that produces a pharmacological effect on a cell, tissue, organ, body system, or whole organism, e.g., when a sufficient amount is contacted with a cell, tissue, or organ, or when a sufficient amount is administered to a subject. The term covers molecules or compositions that are known or expected to exert an effect on cardiac cells or tissues, as well as molecules or compositions that are not known or expected to exert an effect on cardiac cells or tissues. In some embodiments, a drug exerts an effect on one or more proteins in a cardiac cell or tissue (e.g., transmembrane and/or sarcoplasmic reticulum proteins such as ion channels, exchangers, pumps, release proteins, and/or uptake proteins that permit the passage of ions (e.g., sodium, potassium, calcium, magnesium, chloride, bicarbonate, protons, hydroxide ions, or other relevant ions), proteins, or other species). In some embodiments, a drug is a sodium channel blocker, a calcium channel blocker, a calcium channel blocker, or a combination thereof. Drugs may be synthetic or naturally occurring. The term includes prodrugs as well.

As used herein, the term "mature cardiomyocyte" or "mature CM" refers to an adult cardiomyocyte. In contrast, the term "immature cardiomyocyte" or "immature CM" refers to a non-adult CM or a CM that is not fully differentiated, e.g., a fetal cardiomyocyte or a cardiomyocyte derived from a stem cell such as a pluripotent stem cell. In some instances, the immature CM is derived from a human pluripotent stem cell (hPSC-CM). In some embodiments, the immature cardiomyocyte is an induced pluripotent stem cell-derived cardiomyocyte (iPSC-CM). In some embodiments, the immature CM is derived from a cell (e.g., a stem cell such as a pluripotent stem cell) that is obtained from a subject (e.g., a subject that is to be administered, or potentially administered a drug that is assessed for proarrhythmic effects according to methods of the present invention).

Mature and immature CMs can be differentiated from each other in a number of ways, including but not limited to differences in morphology, electrophysiology, and the expression of various proteins. For example, mature CMs tend to be rod-shaped, whereas immature CMs tend to be rounded. In addition, mitochondria in mature CMs tend to be oval-shaped, whereas mitochondria in immature CMs and smaller than those found in mature CMs and/or are more rounded in shape. Mature CMs typically exhibit synchronous contraction, whereas immature CMs typically do not. Mature CMs tend to exhibit faster upstroke velocities (e.g., around 250 mV/ms) and faster conduction velocities (e.g., about 60 cm/s) than immature CMs (e.g., upstroke velocities of about 50 mV/ms and conduction velocities of about 10-20 cm/s (for hPSC-CMs)). Immature CMs also tend to have a more depolarized resting membrane potential (e.g., about −60 mV) as compared to mature CMs (e.g., about −90 mV).

In mature CMs, various ion transporters, sarcomeric proteins, and calcium handling proteins are upregulated as compared to immature CMs. Non-limiting examples include KCNA4, KCNA5, KCNAB1, KCNAB2, KCND2, KCND3, KCNE4, KCNG1, KCNH2, KCNH7, KCNIp2, KCNJ2, KCNJ3, KCNJS, KCNJ8, KCNK1, KCNQ1, KCNV1, SCN1A, SCN1B, SCN2B, SCN3A, SCN4B, SCNSA, HCN1, HCN4, C ACNA1C, C ACNA1D, C ACNA1H, CACNA1G, CACNA2D1, CACNB2, SLC8A1,TRPC3, TRPC4, TRPC6, CFTR, ATp2A2, PLN, CASQ2, RYR2, RYR3, TRDN, ITPR1, ITPR3, ASPH, S100A1, HRC, MYL2, TNNI3, ACTN2, MYH7, MYL3, TNNC1, TNNT2, MYH11, SORBS1, CASQ2, RyR, SERCA, and L-type calcium channels. In addition, certain proteins are downregulated in mature CMs, including aMHC, T-type calcium channels, Titin, and N2BA. Additional information regarding differences between mature and immature CMs can be found, e.g., in Jiang et al. *Mol. Cells* (2018) 41(7):613-621, hereby incorporated by reference in its entirety for all purposes.

Unless specified otherwise, the term "transmembrane voltage" or "$V_m$" refers to the difference in electrical potential (e.g., in millivolts (mV)) between the interior and exterior of a cell (e.g., a cardiomyocyte), and is determined with respect to the exterior of the cell (i.e., a negative $V_m$ means that the interior of the cell is negative with respect to the exterior of the cell).

Unless specified otherwise, the term "intracellular calcium" or "$Ca_i$" refers to cytosolic calcium ions, and does not include calcium ions located in the endoplasmic reticulum, sarcoplasmic reticulum, or mitochondria. In particular embodiments, the term also excludes calcium that is not in ionized for and/or calcium that is bound to a protein or chelator.

The term "proarrhythmic" refers to any effect that results in an increased likelihood that an arrhythmia will occur. Evidence of proarrhythmic effects may be observed at the cellular level (e.g., decreased $(dv/dt)_{max}$, prolongation of the $APD_{V,n}$ or $APD_{Ca,n}$, increased $Ca_i$, depolarization of the resting membrane potential, etc.), tissue level (e.g., decreased conduction velocity, increased automaticity, etc.), or organ level (e.g., prolongation of the QT or corrected QT interval, repolarization abnormalities that manifest as changes in T wave morphology on electrocardiogram, etc.). The arrhythmia may be an atrial arrhythmia, a ventricular arrhythmia, a reentrant arrhythmia, or a combination thereof. In some embodiments, a proarrhythmic effect is caused by modification of the function or properties of a cardiac cell protein (e.g., ion channel, pump, exchanger, SR release protein, or SR uptake protein) by a drug. As a non-limiting example, proarrhythmic effects can be caused by decreased ion channel conductance that is secondary to interactions between a drug and the ion channel.

The term "$APD_{V,n}$" refers to the duration of the $V_m$ action potential (e.g., measured in milliseconds) and is taken to be the time from when the value of the transmembrane potential, in the upstroke, is n % below its maximum value ($t_0$) until it is again repolarized to n % of its maximum value ($t_1$). The term "$APD_{Ca,n}$" represents the corresponding transient duration (e.g., in milliseconds) for the intracellular calcium concentration. The value of n can be any number between 0 and 100, excluding 0 (e.g., 5, 10, 15, 20, 25, 30, 35, 40, 45, 50, 55, 60, 65, 70, 75, 80, 85, 90, or 95). In some embodiments, n is 30, 50, or 80.

The terms "subject," "individual," and "patient" are used interchangeably herein to refer to a vertebrate, preferably a mammal, more preferably a human. Mammals include, but are not limited to, rodents (e.g., mice, rats), simians, humans, farm animals, sport animals, and pets.

III. Description of the Embodiments

In one aspect, the present invention provides a method for determining an effect of a drug on a mature cardiomyocyte (CM). In some embodiments, the method comprises:
(a) obtaining one or more first measurements of transmembrane voltage ($V_m$) and/or one or more first measurements of intracellular calcium concentration ($Ca_i$) in a control immature CM;
(b) storing data representing said one or more first measurements of $V_m$ in vector $v^C$ and/or storing data representing said one or more first measurements of $Ca_i$ in vector $c^C$;
(c) contacting the immature CM with a composition comprising a sufficient amount of the drug to produce a drug-treated immature CM;
(d) obtaining one or more second measurements of $V_m$ and/or one or more second measurements of $Ca_i$ in the drug-treated immature CM;
(e) storing data representing said one or more second measurements of $V_m$ in vector $v^D$ and/or storing data representing said one or more second measurements of $Ca_i$ in vector $c^D$;
(f) inverting the data stored in $v^C$ and/or $c^C$ to update the value of one or more parameters in an immature base CM model, stored in vector $p^{IM,B}$, to yield vector $p^{IM,C}$ that parameterizes an immature control CM model;
(g) inverting the data stored in $v^D$ and/or $c^D$ to update the value of one or more parameters stored in vector $p^{IM,C}$ to yield vector $p^{IM,D}$ that parameterizes an immature drug-treated CM model;
(h) updating one or more values in a diagonal maturation matrix $Q$ such that the equality $Qp^{IM,C}=p^M$ is satisfied, wherein $p^M$ is a vector that parameterizes a mature base CM model and wherein before $Q$ is updated, $Q$ satisfies the equality $p^M=Qp^{IM,B}$;
(i) multiplying $p^{IM,D}$ by $Q$ to generate vector $p^{M,D}$, wherein $p^{M,D}$ parameterizes a mature drug-treated CM model;
(j) using the mature base and drug-treated CM models to generate a simulated mature control action potential (AP) and a simulated mature drug-treated AP, respectively; and
(k) comparing one or more morphological properties of the simulated mature control AP and the simulated mature drug-treated AP in order to calculate a difference, thereby determining the effect of the drug.

In another aspect, the present invention provides a method for selecting a drug (e.g., for administration to a subject) that does not have a proarrhythmic effect on a mature cardiomyocyte (CM). In some embodiments, the method comprises:
(a) obtaining one or more first measurements of transmembrane voltage ($V_m$) and/or one or more first measurements of intracellular calcium concentration ($Ca_i$) in a control immature CM;
(b) storing data representing said one or more first measurements of $V_m$ in vector $v^C$ and/or storing data representing said one or more first measurements of $Ca_i$ in vector $c^C$;

(c) contacting the immature CM with a composition comprising a sufficient amount of the drug to produce a drug-treated immature CM;

(d) obtaining one or more second measurements of $V_m$ and/or one or more second measurements of $Ca_i$ in the drug-treated immature CM;

(e) storing data representing said one or more second measurements of $V_m$ in vector $v^D$ and/or storing data representing said one or more second measurements of $Ca_i$ in vector $c^D$;

(f) inverting the data stored in $v^C$ and/or $c^C$ to update the value of one or more parameters in an immature base CM model, stored in vector $p^{IM,B}$, to yield vector $p^{IM,C}$ that parameterizes an immature control CM model;

(g) inverting the data stored in $v^D$ and/or $c^D$ to update the value of one or more parameters stored in vector $p^{IM,C}$ to yield vector $p^{IM,D}$ that parameterizes an immature drug-treated CM model;

(h) updating one or more values in a diagonal maturation matrix $Q$ such that the equality $Qp^{IM,C}=p^M$ is satisfied, wherein $p^M$ is a vector that parameterizes a mature base CM model and wherein before $Q$ is updated, $Q$ satisfies the equality $p^M=Qp^{IM,B}$;

(i) multiplying $p^{IM,D}$ by $Q$ to generate vector $p^{M,D}$, wherein $p^{M,D}$ parameterizes a mature drug-treated CM model;

(j) using the mature base and drug-treated CM models to generate a simulated mature control action potential (AP) and a simulated mature drug-treated AP, respectively;

(k) comparing a morphological property of the simulated mature control AP to the morphological property of the simulated mature drug-treated AP in order to calculate a difference; and (l) based upon the difference in the morphological property between the simulated mature control and drug-treated APs, determining that the drug does not have a proarrhythmic effect and selecting the drug when it does not have a proarrhythmic effect.

A. Measuring Transmembrane Voltage and Intracellular Calcium

In some embodiments, only $V_m$ is measured (e.g., in the immature CM). In some embodiments, only $Ca_i$ is measured. In some embodiments, both $V_m$ and $Ca_i$ are measured.

In some embodiments, $V_m$ and/or $Ca_i$ are optically measured, e.g., using a voltage- and/or calcium-sensitive indicator or sensor (e.g., a dye), respectively. For optical measurements, the indicator or sensor will typically be fluorescent. Indicator(s) and/or sensor(s) that produce signals in the visible, far-red, and/or near-infrared spectrum can be used. Such measurements can be made using a microphysiological system (MPS). The use of microphysiological systems to measure $V_m$ and/or $Ca_i$ is described in the Examples section below and also described, e.g., in Anurag Mathur. et al. *Scientific reports* (2015) 5:8883, which is incorporated herein in its entirety for all purposes.

As a brief non-limiting example, an MPS system is loaded and matured prior to drug exposure. On the day upon which studies are performed, freshly measured drug is dissolved into an appropriate solvent (e.g., DMSO) or cell media and serially diluted. Each concentration of the drug to be tested is preheated (e.g., for about 15-20 minutes) in a water bath (e.g., at about 37° C.) and subsequently sequentially injected in the device. At each dose, after an appropriate exposure time (e.g., about 5 minutes), the drug's response on the microtissue is recorded using a suitable imaging device (e.g., a Nikon Eclipse TE300 microscope fitted with a QImaging camera). Fluorescent images are acquired at a suitable frame rate (e.g., at 100 frames per second) using appropriate filters to capture fluorescence from the selected indicator(s) (e.g., GCaMP for $Ca_i$ and/or and BeRST-1 for $V_m$). Images are obtained across the entire chip for a suitable length of time (e.g., about 6-8 seconds), with cell excitation paced at an appropriate frequency (e.g., about 1 Hz), to capture multiple beats for processing. Fluorescence videos are then analyzed using software (e.g., Python software utilizing the open source Bio-Formats tool or other suitable software) to produce characteristic voltage and calcium waveforms for each chip and tested drug dose. Briefly, for each analysis, the fluorescent signal for the entire visual field is averaged, excluding pixels which do not change significantly in intensity over the acquisition. The signal is then smoothed (e.g., using a 3 point median filter), and an appropriate number (e.g., 5-7) individual action potentials or calcium transients are overlayed by aligning the maximum dF/dt and then averaged into a single transient.

In some embodiments, $V_m$ and/or $Ca_i$ (e.g., in an immature CM) are detected by observing or recording a signal (e.g., optical signal). In particular embodiments, the signal is displayed on a device (e.g., computer monitor or other electronic display) and/or recorded on an analog and/or digital recording medium. As non-limiting examples, devices that can be used to detect a signal (e.g., optical signal, such as a fluorescent signal) include, CCD cameras, video cameras, photographic film, laser-scanning devices, fluorometers, photodiodes, quantum counters, epifluorescence microscopes, scanning microscopes, fluorescence microplate readers, and signal amplification using photomultiplier tubes. Typically, the signal-detecting device will need to be coupled to a microscope. In addition, appropriate filter(s) may be used, depending on the choice of indicator(s) to detect $V_m$- and/or $Ca_i$-related signals. In some embodiments, detecting a fluorescent signal comprises detecting a change in fluorescence (e.g., a change in fluorescence intensity, fluorescence excitation or emission wavelength distribution, fluorescent lifetime, and/or fluorescence polarization).

For measurement of $V_m$, in some embodiments, the signal is generated using a fluorescent voltage indicator or sensor (e.g., a voltage-sensitive fluorescent dye). Voltage-sensitive dyes change their absorbance or fluorescence when there is a change in the membrane potential of the cell to which they are bound. Generally, voltage-sensitive dyes are grouped into slow dyes and fast dyes. Slow dyes respond to changes in voltage with a time constant of milliseconds to seconds. Fast dyes respond with time constants in the microsecond range. A non-limiting example of a suitable fluorescent voltage indicator is Berkeley Red Sensor of Transmembrane Potential (BeRST1). Non-limiting examples of other indicators include carbocyanines, rhodamines, ionic oxonols, and those based on aminonaphthylethenylpyridinium (ANEP) and aminonapthylbutydienylquinolinium (ANBDQ) backbones (e.g., Di-1-ANEPEQ, Di-1-ANEPPQ, Di-2-ANEPEQ, Di-2-ANBDQPQ, Di-2-AN(F)EPPTEA, Di-3-ANEPPDHQ, Di-4-ANEPPS, Di-4-AN(F)EPPTEA, Di-4-AN(F)EP(F)PTEA, Di-4-ANEP(F2)PTEA, Di-4-ANBDQBS, Di-4-ANBDQPQ, Di-4-ANEQ(F)PTEA, and Di-8-ANEPPS).

For measurement of $Ca_i$, in some embodiments, the signal is generated using a fluorescent calcium indicator or sensor (e.g., a calcium-sensitive fluorescent dye). In some embodiments, the signal is proportional (e.g., directly proportional)

to the intracellular calcium concentration. In other embodiments, the signal is inversely proportional to the intracellular calcium concentration. Non-limiting examples of suitable fluorescent calcium indicators or sensors include GCaMP, bis-fura-2, BTC, calcium green-1, calcium green-2, calcium green-5n, calcium orange, calcium crimson, fluo-3, fluo-4, fluo-5F, fluo-4FF, fluo-5N, fura-2, fura-4f, fura-6F, fura-FF, fura red, indo-1, mag-fluo-4, mag-fura-2, mag-indo-1, magnesium green, Oregon green 488 BAPTA-1, Oregon green 488 BAPTA-2, Oregon green 488 BAPTA-6F, Oregon green 488 BAPTA-5N, quin-2, rhod-2, rhod-3, rhod-FF, rhod-5N, X-rhod-1, X-rhod-5F, a genetically-encoded sensor, analogs thereof, acetoxymethyl esters thereof, acetate esters thereof, water soluble salts thereof, dextran variants thereof, cadaverine variants thereof, thiol-reactive iodoacetamides thereof, and combinations thereof.

In some embodiments, a non-ratiometric fluorescent calcium indicator or sensor is used, wherein the intracellular calcium concentration is determined by a relative increase in fluorescence intensity. Non-ratiometric indicators or sensors primarily work in the visible wavelength range, and are advantageous in that the use of a single excitation wavelength allows for simpler instrumentation and/or simultaneous observation of other parameters. In some embodiments, the relationship between fluorescence and the absolute calcium concentration (e.g., absolute intracellular calcium concentration) is represented by the following equation:

$$[Ca^{2+}]=K_d \times (F-F_{min})/(F_{max}-F)$$

where $K_d$ is the dissociation constant of the fluorescent indicator and $F_{min}$ and $F_{max}$ are fluorescence values obtained at minimum and maximum calcium concentrations (e.g., 0 and saturating values). $K_d$ is commonly determined for each experimental condition, as $K_d$ can be modified by factors such as pH, protein concentration, ionic strength, and lipid interactions.

In some embodiments, a ratiometric fluorescent calcium indicator or sensor is used, wherein the intracellular calcium concentration is measured as a ratio between two fluorescence intensity values that are measured at two different excitation or emission wavelengths. Ratiometric indicators or sensors are advantageous in that they allow for correction for unequal dye loading, bleaching, or focal plane shift.

In some embodiments, more than one measurement of $V_m$ and/or $Ca_i$ is obtained in the control immature CM. In some embodiments, more than one measurement of $V_m$ and/or $Ca_i$ is obtained in the drug-treated immature CM. When both $V_m$ and $Ca_i$ are measured, the number of measurements can be different, or they can be the same. The number of measurements will depend on the measurement frequency and the length of time that measurements are made. In some embodiments, about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 1,500,000, 2,000,000, 2,500,000, 3,000,000, 3,500,000, 4,000,000, 4,500,000, 5,000,000, 5,500,000, or more measurements of $V_m$ and/or $Ca_i$ (e.g., in a control and/or drug-treated immature CM) are obtained.

In some embodiments, at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 $V_m$ and/or $Ca_i$ measurements are made per second. In some embodiments, about 100, 150, 200, 250, 300, 350, 400, 450, 500, 550, 600, 650, 700, 750, 800, 850, 900, 950, 1,000, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,150, 2,200, 2,250, 2,300, 2,350, 2,400, 2,450, 2,500, 2,550, 2,600, 2,650, 2,700, 2,750, 2,800, 2,850, 2,900, 2,950, 3,000 $V_m$ and/or $Ca_i$ measurements are made per second. When both $V_m$ and $Ca_i$ are measured, the measurement frequencies for $V_m$ and $Ca_i$ can be different, or they can be the same.

In some embodiments, $V_m$ and/or $Ca_i$ measurements are made for at least about 1 second. In some embodiments, $V_m$ and/or $Ca_i$ measurements are made for about least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds. In some embodiments, $V_m$ and/or $Ca_i$ measurements are made for about least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes.

In some embodiments, $V_m$ and/or $Ca_i$ measurements are made for between about 1 second and about 60 seconds, between about 1 second and about 50 seconds, between about 1 second and about 40 seconds, between about 1 second and about 30 seconds, between about 1 second and about 20 seconds, or between about 1 second and about 10 seconds. In some embodiments, $V_m$ and/or $Ca_i$ measurements are made for between about 1 minute and about 30 minutes, between about 1 minute and about 25 minutes, between about 1 minute and about 20 minutes, between about 1 minute and about 15 minutes, between about 1 minute and about 10 minutes, between about 1 minute and about 9 minutes, between about 1 minute and about 8 minutes, between about 1 minute and about 7 minutes, between about 1 minute and about 6 minutes, between about 1 minute and about 5 minutes, between about 1 minute and about 4 minutes, between about 1 minute and about 3 minutes, or between about 1 minute and about 2 minutes.

In some embodiments, the control immature CM and the drug-treated immature CM are the same (i.e., one or more $V_m$ and/or $Ca_i$ measurements are obtained in the control immature CM, and then one or more $V_m$ and/or $Ca_i$ measurements are obtained in the same immature CM after the immature CM has been contacted with the composition comprising the sufficient amount of the drug). In other embodiments, the control immature CM and the drug-treated immature CM are different cells. In some embodiments, measurements of $V_m$ and/or $Ca_i$ are obtained in one control and/or one drug-treated immature CM. In other embodiments, measurements of $V_m$ and/or $Ca_i$ are obtained in 2, 3, 4, 5, 6, 7, 8, 9, 10, 11, 12, 13, 14, 15, 16, 17, 18, 19, 20, or more control and/or drug-treated immature CMs.

In some embodiments, the composition comprising the sufficient amount of the drug is contacted with the CM for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds before the one or more second measurements of $V_m$ and/or the one or more second measurements of $Ca_i$ are obtained. In some embodiments, the composition comprising the sufficient amount of the drug is contacted with the CM for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes before the one or more second measurements of $V_m$ and/or the one or more second measurements of $Ca_i$ are obtained.

B. Inversion and Maturation

According to methods of the present invention, $V_m$ and/or $Ca_i$ measurements are obtained in the control and drug-treated immature CMs. The choice of whether $V_m$, $Ca_i$, or both are measured will depend, e.g., on the particular drug(s) being studied, the anticipated effects (e.g., on a cardiac action potential (AP)), the phase of the cardiac AP that is of most interest, etc. The one or more measurements of $V_m$ (or a subset thereof) obtained in the control immature CM are stored in vector $v^C$. Similarly, the one or more measurements of $Ca_i$ (or a subset thereof) are stored in vector $c^C$. The values stored in $v^C$ and/or $c^C$ (again, depending on whether it is desirable to use voltage and/or intracellular calcium concentration data for a particular study) are used to update one or more parameters in a computational model, specifically a model of an immature CM. Models are discussed in more detail below, and the choice of a suitable model will readily be apparent to one of skill in the art. The choice of model will be dictated, e.g., by the particular drug(s) being studied, the choice of model organism (e.g., human, dog, pig, guinea pig, mouse, or rat), the specific properties of the cardiac AP that are of interest, etc. The parameters of the computational model of the immature CM (e.g., the parameters that are to be updated based on $V_m$ and/or $Ca_i$ measurements) are stored in vector $p^{IM,B}$, which represents the base model. Vectors $v^C$ and/or $c^C$ are inverted to update the value of one or more parameters stored in $p^{IM,B}$, which yields vector $p^{IM,C}$. $p^{IM,C}$ parameterizes or characterizes the computational model of the immature control CM. In other words, the $V_m$ and/or $Ca_i$ data obtained from measurements obtained from the control immature CM (i.e., stored in $v^C$ and/or $c^C$, respectively), are used to update the computational base model so that it better fits or reproduces action potentials that were observed in the control immature CM.

Furthermore, the one or more measurements of $V_m$ (or a subset thereof) obtained in the control immature CM are stored in vector) $v^D$. Similarly, the one or more measurements of $Ca_i$ (or a subset thereof) are stored in vector $c^D$. Vectors $v^D$ and/or $c^D$ are inverted to update the value of one or more parameters stored in $p^{IM,C}$, which yields vector $p^{IM,D}$. $p^{IM,D}$ parameterizes or characterizes the computational model of the immature drug-treated CM. In other words, the $V_m$ and/or $Ca_i$ data obtained from measurements of the drug-treated immature CM (i.e., stored in $v^D$ and/or $c^D$, respectively), are used to update the computational model of the control immature CM so that it better fits or reproduces action potentials that were observed in the drug-treated immature CM. Accordingly, it follows from above that in some embodiments only $v^C$ and $V^D$ are inverted, in other embodiments only $c^C$ and $c^D$ are inverted, and in still other embodiments $v^c$, $c^C$, $v^D$, and $c^D$ are inverted. For inversion of $v^D$ and/or $c^D$, in some embodiments, the effect of a drug is simulated. In particular embodiments, the simulated drug effect is that of reducing maximum conductance (e.g., of an ion channel) and/or reducing the maximum rate of an ion pump and/or an ion exchanger.

In some embodiments, inverting the data (e.g., stored in $v^C$, $c^C$, $v^D$, and/or $c^D$) comprises minimizing a cost function. In some embodiments, minimizing the cost function comprises minimizing the differences between one or more characteristics determined in an experimentally-observed AP or calcium transient (e.g., measured in a control or drug-treated immature CM) and the corresponding characteristic(s) in an AP or calcium transient generated by the immature base CM model or the immature control CM model (e.g., initially generated by the immature base CM model or the immature control CM model, before the immature base or control CM model has been optimized to more closely match the data obtained from the immature control or drug-treated CM, respectively).

In some embodiments, the cost function is only based on voltage. In these embodiments, the one or more characteristics may comprise $V_m$, $APD_{V,n}$ (e.g., $APD_{V,30}$, $APD_{V,50}$, and/or $APD_{V,80}$), $(dv/dt)_{max}$, resting membrane potential, or a combination thereof. In other embodiments, the cost function is only based on $Ca_i$. In these embodiments, the one or more characteristics may comprise $APD_{Ca,n}$ (e.g., $APD_{Ca,30}$, $APD_{Cs,50}$, and/or $APD_{Ca,80}$), maximum upstroke velocity of the calcium concentration $((dc/dt)_{max})$, $Ca_i$ (e.g., peak $Ca_i$), or a combination thereof. In some other embodiments, the cost function is based on voltage and $Ca_i$. In these embodiments, the one or more characteristics may comprise $V_m$, $APD_{V,n}$ (e.g., $APD_{V,30}$, $APD_{V,50}$, and/or $APD_{V,80}$), $(dv/dt)_{max}$, resting membrane potential, $APD_{Ca,n}$ (e.g., $APD_{Ca,30}$, $APD_{Cs,50}$, and/or $APD_{Ca,80}$), maximum upstroke velocity of the calcium concentration $((dc/dt)_{max})$, $Ca_i$, or a combination thereof. It is understood that each instance of n is independently selected. Furthermore, multiple instances of n can be selected (e.g., $APD_{V,30}$, $APD_{V,50}$, and/or $APD_{V,80}$ can be used, and/or $APD_{Ca,30}$, $APD_{Ca,50}$, and/or $APD_{Ca,80}$, can be used).

In some embodiments, the cost function is iteratively minimized. In some embodiments, between 2 and 100 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) iterations are used. In some embodiments, more than 100 iterations are used.

In some embodiments, during each iteration, for each parameter that is being updated, 1 or more values for the parameter are selected (e.g., randomly selected). In particular embodiments, the one or more values for each parameter are selected from within an interval of allowed values. In some instances, between about 1,000 and about 5,000 (e.g., about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, or 5,000) values for each parameter being updated are selected (e.g., randomly selected). In some embodiments, more than 5,000 values are selected. When an interval of allowed values (i.e. for a parameter that is being updated in a given iteration) is used, in some embodiments, the length or size of the interval is decreased with each iteration. In some embodiments, the length or size of the interval is decreased with each iteration by about 90%, 80%, 70%, 60%, 50%, 40%, 30%, 20%, or 10%.

In order to arrive at a computational model of the mature drug-treated CM (which is parameterized by the vector $p^{M,D}$), a diagonal matrix (i.e., a diagonal maturation matrix, denoted $Q$), is used. Before being used to generate vector $p^{M,D}$, $Q$ is updated. In particular, one or more values in $Q$ are updated such that the equality $Q p^{IM,C} = p^M$ is satisfied. Initially, before being updated, $Q$ satisfies the equality $p^M = Qp^{IM,B}$. $p^M$ is a vector that parameterizes a computational base model of the mature CM.

To generate the vector $p^{M,D}$ (i.e., which parameterizes the model of the mature drug-treated CM), the vector $p^{IM,D}$ (which parameterizes the model of the immature drug-treated CM) is multiplied by the maturation matrix $Q$. The concept of maturation by multiplication is illustrated in FIG. 6. Multiplying a vector p by $Q$ may change any number of model features in a computational CM model that is parameterized by p. As non-limiting examples, multiplying a vector p by $Q$ may change the number of one or more proteins, the cell volume, and/or the cell surface area in the CM model that is parameterized by p. The one or more proteins may include, as non-limiting examples, membrane proteins (e.g., ion channels, pumps, and/or exchangers), sarcoplasmic reticulum (SR) release proteins, SR uptake proteins, or combinations thereof.

C. Cardiomyocyte Models

According to methods of the present invention, cardiac action potentials (APs) are simulated using computational cardiomyocyte models, which are parameterized by a vector p (e.g., $p^M$ and $p^{M,D}$ for mature control and drug-treated CMs, respectively). The vector p does not necessarily need to contain all of the parameters that are present in a given computational CM model, so long as p contains the parameters that are relevant to fitting the computational models to the data obtained from the control and drug-treated CMs.

The parameters contained in vector p may represent any number of components, properties, or properties of components that are present within a simulated CM. The one or more parameters may represent, as non-limiting examples, the number of one or more proteins in the simulated cell, the dynamics of one or more proteins in the simulated cell, the volume of the simulated cell, the surface area of the simulated cell, the cell membrane capacitance of the simulated cell, or a combination thereof. The one or more proteins may be, as non-limiting examples, transmembrane protein(s) (e.g., ion channel(s), ion exchanger(s), ion pump(s), or any combination thereof), sarcoplasmic reticulum (SR) protein(s) (e.g., SR release and/or uptake protein(s)), or any combination thereof. The one or more proteins (e.g., ion channel(s), exchanger(s), pump(s), release protein(s), and/or uptake protein(s)) may transport or permit the passage of ions (sodium, potassium, calcium, magnesium, chloride, bicarbonate, protons, hydroxide ions, or other relevant ions), proteins, or other species, e.g., into or out of the simulated cell, or into or out of a particular compartment, subspace, or organelle within the simulated cell. In some embodiments, the one or more parameters represent a maximum conductance (e.g., of an ion channel) and/or a maximum rate (e.g., of an ion exchanger or pump). In some embodiments, the one or more parameters represent a value (e.g., a time constant) that is associated with the rate of opening or closing of an ion channel (e.g., an ion channel gating variable), an association constant, a dissociation constant, or a combination thereof.

Available computational CM models will be known to one of skill in the art. The choice of model will be dictated by, e.g., the particular organism of interest (e.g., human, dog, pig, guinea pig, mouse, or rat), cell type of interest (e.g., atrial or ventricular cell), the particular drug(s) being studied, particular electrophysiological properties or effects of interest (e.g., that are potentially modulated by the drug), specific diseases, pathologies, or mutations, etc.

In some embodiments, a candidate CM model is further analyzed for parameter sensitivity. As discussed in Examples 1 and 2 below, some currents in particular CM models can be identified using $V_m$ and/or $Ca_i$ data, whereas other membrane currents are practically invisible using this data. Therefore, in some embodiments, methods provided herein (described in Example 3 below) are used to evaluate the identifiability of ion channel conductances (e.g., in a CM model) based on, for example, observations of $V_m$. In particular, identifiability indices are computed for various transmembrane currents in a CM model, based on singular value decomposition (SVD). Accordingly, in some embodiments, a CM model for use in methods of the present invention is selected based on parameter sensitivity (i.e., as assessed using identifiability indices of transmembrane currents in the CM model).

Non-limiting examples or available models are described in the examples provided herein and are also described, e.g., in Ten Tusscher et al. (*American Journal of Physiology-Heart and Circulatory Physiology*, 291(3):H1088-H1100, 2006), Grandi et al. (*Journal of Molecular and Cellular Cardiology*, 48(1):112-121, 2010), O'Hara et al. (*PLoS Computational Biology*, 7(5):e1002061, 2011), and Paci et al. (*Annals of Biomedical Engineering*, 41(11):2334-2348, 2013), the disclosures of which are incorporated in their entirety for all purposes.

D. Determining Drug Effects

In order to determine the effects of a drug (e.g., on a mature CM) or to select a drug (e.g., that does not have a proarrhythmic effect on a mature CM) according to methods of the present invention, the mature base CM model and the mature drug-treated CM model (i.e., parameterized by vectors $p^M$ and $p^{M,D}$, respectively) are used to generate a simulated mature control AP and a simulated mature drug-treated AP, respectively. One or more morphological properties are then compared between the simulated mature control AP and the simulated mature drug-treated AP in order to calculate difference(s) between the two action potentials, and the difference(s) are used to determine the effect(s) of the drug and/or to select a drug.

In some embodiments, more than one simulated mature control AP and/or more than one simulated mature drug-treated AP are generated. In particular embodiments, a number of simulated APs (e.g., at least 2, 3, 4, 5, 6, 7, 8, 9, 10, 15, 20, 30, 40, 50, 60, 70, 80, 90, 100, 200, 300, 400, 500, 600, 700, 800, 900, 1,000, or more) are generated before specific simulated APs are selected comparison of morphological properties. In some instances, the number of simulated APs that are generated depends on the simulated pacing rate, choice of specific CM model, mathematical method used to solve equations in the CM model, how quickly parameter(s) in the CM model approach steady state, etc. In some embodiments, only one simulated mature control AP and/or only one simulated mature drug-treated AP are selected for comparison of morphological properties. In some embodiments, more than one (e.g., at least 2, 3, 4, 5, 6, 7, 8, 9, 10, 11, 12, 13, 14, 15, 16, 17, 18, 19, 20, or more) simulated mature control APs and/or simulated mature drug-treated APs are selected for comparison of morphological properties.

In some embodiments, the one or more morphological properties (e.g., that are compared between simulated mature control and drug-treated APs) are selected from the group consisting of $APD_{V,n}$, $APD_{Ca,n}$, maximum $V_m$ upstroke velocity $((dv/dt)_{max})$, resting membrane potential, maximum $Ca_i$ upstroke velocity $((dc/dt)_{max})$, $Ca_i$ (e.g., peak $Ca_i$), and a combination thereof. It is understood that each instance of n is independently selected. Furthermore, multiple instances of n can be selected (e.g., $APD_{V,30}$, $APD_{V,50}$, and/or $APD_{V,80}$ can be used in one comparison, and/or $APD_{Ca,30}$, $APD_{Ca,50}$, and/or $APD_{Ca,80}$, can be used in one comparison). In some embodiments, more than 1 (e.g., 2, 3, 4, 5, 6 or more) morphological property is compared. In some embodiments, the effect of more than 1 (e.g., 2, 3, 4, 5, 6, or more) drug on a mature CM is determined, or more than 1 (e.g., 2, 3, 4, 5, 6, or more) drug is selected that does not have a proarrhythmic effect of a mature CM.

In some embodiments, a drug is determined to have a proarrhythmic effect (e.g., on a mature CM) when at least one of the morphological properties (e.g., $APD_{V,n}$ or $APD_{Ca,n}$) in the simulated mature drug-treated AP is higher (e.g., at least about 0.1-fold, 0.2-fold, 0.3-fold, 0.4-fold, 0.5-fold, 0.6-fold 0.7-fold, 0.8-fold, 0.9-fold, 1-fold 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold higher) compared to the corresponding morphological property in the simulated mature control AP.

In some embodiments, a drug is determined to have a proarrhythmic effect (e.g., on a mature CM) when at least one of the morphological properties (e.g., $(dv/dt)_{max}$) in the simulated mature drug-treated AP is lower (e.g., at least about 0.1-fold, 0.2-fold, 0.3-fold, 0.4-fold, 0.5-fold, 0.6-fold, 0.7-fold, 0.8-fold, 0.9-fold, 1-fold 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold lower) compared to the corresponding morphological property in the simulated mature control AP.

In some embodiments, a subject (e.g., a patient) is not administered the drug when the drug is determined to have a proarrhythmic effect (e.g., on a mature CM).

In some embodiments, a drug is selected (e.g., for a subject such as a patient) or is determined to not have a proarrhythmic effect (e.g., on a mature CM) when the morphological property (e.g., $APD_{V,n}$ or $APD_{Ca,n}$) in the simulated mature control AP is less than about 0.1-fold, 0.2-fold, 0.3-fold, 0.4-fold, 0.5-fold, 0.6-fold, 0.7-fold, 0.8-fold, 0.9-fold, 1-fold 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold lower compared to the morphological property in the simulated mature drug-treated AP.

In some embodiments, a drug is selected (e.g., for a subject such as a patient) or is determined to not have a proarrhythmic effect (e.g., on a mature CM) when the morphological property (e.g., $(dv/dt)max$) in the simulated mature control AP is less than about 0.1-fold, 0.2-fold, 0.3-fold, 0.4-fold, 0.5-fold, 0.6-fold, 0.7-fold, 0.8-fold, 0.9-fold, 1-fold 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold higher compared to the morphological property in the simulated mature drug-treated AP.

In some embodiments, the methods of the present invention further comprise administration of a drug (e.g., a drug selected according to methods of the present invention) to a subject (e.g., a patient or a subject in need thereof).

E. Computer Systems

The methods of the present invention may be performed (e.g., partially performed) using a computer system, which may include one or more processors that can be configured to perform steps of the disclosed methods. Thus, embodiments of the present invention can be directed to computer systems configured to perform one or more steps of any of the methods provided herein, potentially with different components performing a respective step or a respective group of steps. As non-limiting examples, computer system(s) can be used in methods of the present invention to execute CM models, compare or analyze APs generated by CM models, perform vector inversion operations, perform maturation operations, perform matrix update operations, record, analyze, transform, or display data (e.g., optical data), or any combination thereof.

A computer system can include a plurality of the same components or subsystems, e.g., connected together by external or internal interfaces. In some embodiments, a computer system includes a single computer apparatus, containing subsystems that can be the components of the computer apparatus. In other embodiments, a computer system can include multiple computer apparatuses, each being a subsystem, with internal components. A computer system can include desktop computers, laptop computers, tablets, mobile phones, and/or other mobile devices. In some embodiments, computer systems, subsystems, or apparatuses can communicate over a network. In such instances, one computer can be considered a client and another computer a server, where each can be part of a same computer system. A client and a server can each include multiple systems, subsystems, or components.

The subsystems can be interconnected via system busses. Additional subsystems may include a printer, a keyboard, storage device(s), monitor(s), and/or input device(s) such as imaging device(s). Peripherals and input/output (I/O) devices, which can be coupled to an I/O controller, can be connected to the computer system by any number of means known in the art such as input/output (I/O) ports (e.g., USB,)FireWire®. For example, an I/O port or an external interface (e.g., Ethernet, Wi-Fi, etc.) can be used to connect a computer system to a wide area network such as the Internet, a mouse input device, or a scanner or other imaging device. Interconnection via a system bus allows a central processor to communicate with subsystems and to control the execution of a plurality of instructions from system memory and/or storage device(s) (e.g., flash memory, a fixed disk, such as a hard drive, or optical disk), as well as the exchange of information between subsystems. System memory and/or storage device(s) may embody a computer readable medium. Any of the data described herein can be output from one component to another component and/or can be output to the user.

Embodiments of the present invention may be implemented in the form of control logic using computer software with a generally programmable processor in a modular or integrated manner and/or using hardware (e.g., an application specific integrated circuit or field programmable gate array). As used herein, a processor includes a single-core processor, multi-core processor on a same integrated chip, or multiple processing units on a single circuit board or networked. A person of ordinary skill in the art will be aware of other ways and/or methods to implement embodiments of the present invention using a combination of hardware and software.

Software components or functions used to perform steps in methods of the present invention may be implemented as software code to be executed by a processor using any suitable computer language such as, for example, Java, C, C++, C#, Objective-C, Swift, or a scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or digital versatile disk (DVD), flash memory, and the like. The computer readable medium may be any combination of such storage or transmission devices.

Programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, flash memory, a CD, or an entire computer system), and may be present on or within different computer products within a system or network.

IV. Examples

The present invention will be described in greater detail by way of specific examples. The following exampled are offered for illustrative purposes, and are not intended to limit the invention in any manner. Those of skill in the art will readily recognize a variety of noncritical parameters which can be changed or modified to yield essentially the same results.

Example 1

Detecting Side Effects of Drugs by In Silico Maturation of hiPSC-Derived Cardiomyocytes Introduction Our approach to estimate effects of drugs on M cells based on measurements of IM cells can be summarized as follows:
1. An MPS that uses voltage and calcium sensitive dyes is used to record average traces of the transmembrane potential and the intracellular (cytosolic) calcium concentration of hiPSC-CMs. Data are collected for the cells both before and after a drug has been applied.
2. The voltage and calcium traces are inverted in order to define a mathematical model of the AP of the given IM cells. The effect of the drug is reflected in terms of changes in the maximum conductances of the AP model.
3. The IM models are multiplied by a maturation matrix in order to obtain models for the M cells. The effect of the drug for adult cells is estimated by comparing the AP models of the M cells.

This report briefly describes how the above may be accomplished.

Results

Our aim is to demonstrate that drug effects for mature cardiomyocytes can be estimated using data from their immature counterpart. We start by demonstrating that a cost function, measuring the difference between data and model, is sensitive with respect to changes in the maximum conductance of some major currents. Next, we show that this sensitivity is sufficient to invert simulated data and obtain a mathematical model. This model can be mapped from the IM case to the M case simply by multiplying a parameter vector by a diagonal maturation matrix. Finally, we apply the method of inversion to obtain an IM model based on measured data using voltage- and calcium-sensitive dyes in an MPS. Again, the IM model is mapped to an M model. The effects of drugs are identified by inverting MPS data (voltage and cytosolic calcium concentration) and then mapping the resulting model from IM to M giving a mathematical model of the mature cardiomyocytes under the influence of a drug.

The $H_{V+Ca}$ Cost Function is Sensitive with Respect to Perturbations of Major Currents For correct inversion of data to determine the current responsible for voltage or calcium waveform changes, it is necessary that the chosen cost function is sensitive with respect to perturbations in the maximum conductance of the model currents and fluxes. We first assessed theoretical sensitivity, generating control data using the simulator and evaluating its sensitivity through perturbing the maximum conductance of currents and fluxes. In FIG. 1, we illustrate the sensitivity of three chosen cost functions where the base model (see the Methods section) is defined by a modified version of the Paci et al. model [9].

We see that the chosen cost function using voltage alone, $H_V$, is sensitive to only some of the currents and fluxes. It should be mentioned here, that the maximum upstroke velocity of the action potential is not added as a part of the $H_V$ cost function. Adding this component would improve sensitivity (especially for the sodium current), but the measured data to be addressed below does not (at present) provide sufficient accuracy of the upstroke velocity and therefore this component is not part of $H_V$. However, the upstroke velocity of the calcium transient can be accurately estimated from the MPS measurements and is therefore a part of the cost function describing the calcium mismatch, $H_{Ca}$. This cost function is, in general, less sensitive than the $H_V$ version. Finally, we consider the cost function combining both the voltage and calcium data, $H_{V+Ca}$, and observe that it is more sensitive to perturbations than both $H_V$ and $H_{Ca}$ alone, although some currents are still largely invisible.

Simulated Channel Block Identification

Figure 2:
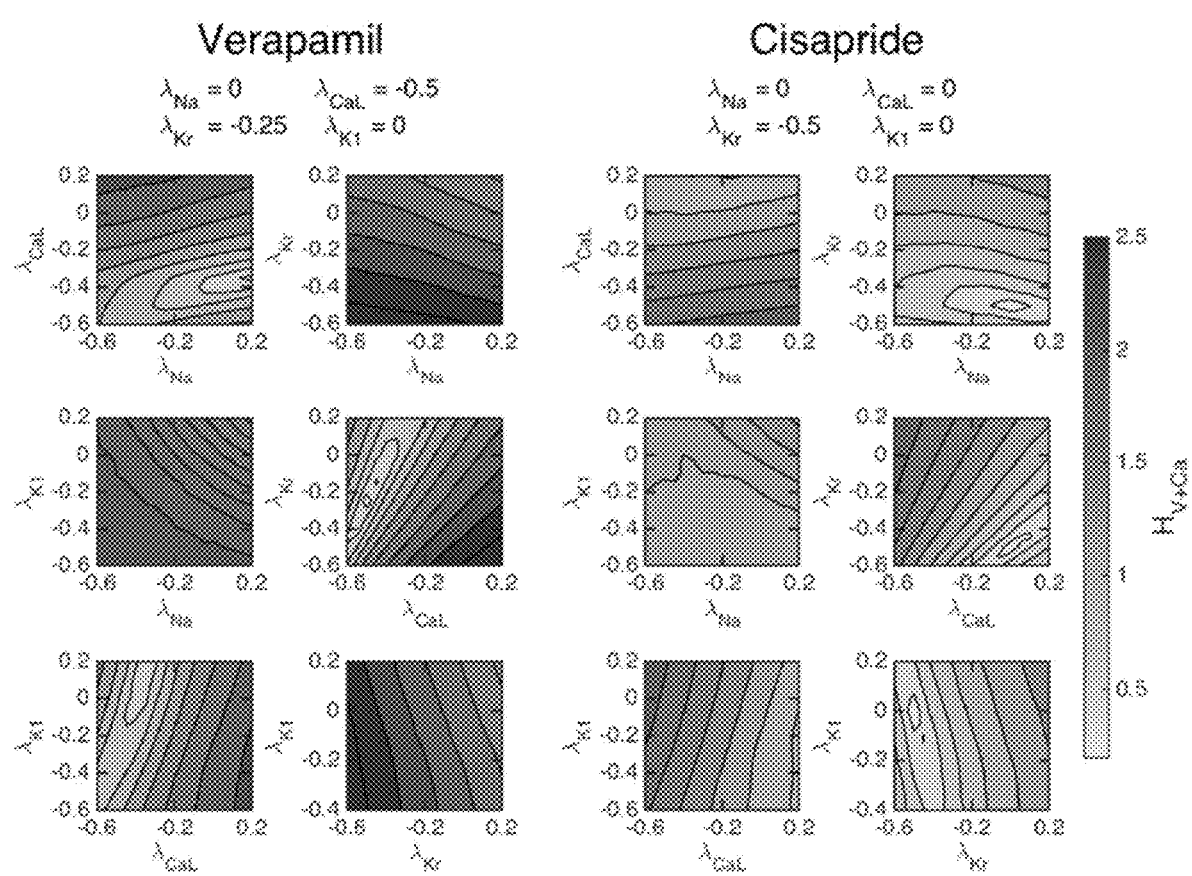
FIG. 2 shows that the cost function (8) in Example 1 (or (4) in Example 2) with ε=0.2 was evaluated using simulated data for pairwise perturbations of maximum conductances to examine if a unique minimum could be found corresponding to chosen drug effects. Left panels: the effect of verapamil was simulated by blocking the $I_{caL}$ and $I_{Kr}$ by 50% and 25%, respectively. Right panels: the effect of cisapride was simulated by blocking the $I_{Kr}$ by 50%. For both drugs, clear minimums were observed at the specified channel blockages.

Although FIG. 1 shows the sensitivity of the computed cost functions with respect to individual currents, we need to establish that the cost functions are adequately sensitive when multiple currents are allowed to vary. In FIG. 2, we show the values of $H_{V+Ca}$, as a function of pairwise perturbations in the maximum conductances of four major channels. The traces are theoretically computed using known effects of two chosen drugs; verapamil, which blocks $I_{CaL}$, and IKr, and cisapride which blocks $I_{Kr}$, see [29].

Our results indicate that the cost function using both voltage and calcium can theoretically identify the simulated channel block of the chosen drugs. The left panels show the value of $H_{V+Ca}$ as a function of the maximum conductances when the control data are computed using the specified blocking due to the application of verapamil. Six different configurations of pairwise blocking perturbations were tested and a minimum is clearly obtained close to the correct blocking of Ica, and IKr. Meanwhile, in the right panel, we show the values of $H_{V+Ca}$ when $I_{Kr}$ is blocked by 50%, simulating the effect of cisapride. The pairwise perturbations clearly identify that IKr is blocked by around 50%.

Simulated Drug Effect Identification Using the Inversion Procedure

Figure 3:
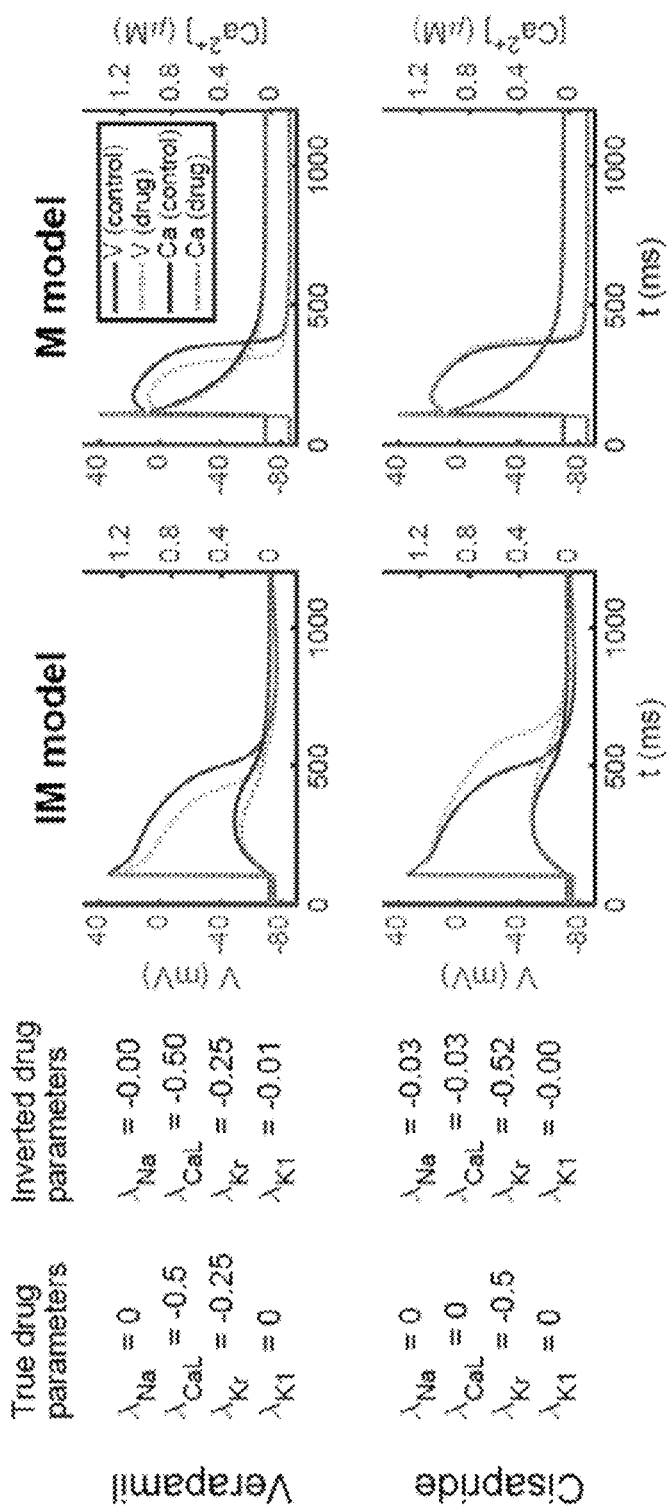
FIG. 3 shows identification of drug effects on M cells based on simulated data of IM cells. Left panel: results of inversion by minimizing the cost function (8) in Example 1 with ε=0.2. Middle panel: action potential (blue) and calcium transient (red) before and after (dotted) the drug is applied. Right panel: model results after application of the maturation matrix.

In the Methods below, we describe the inversion of calcium and voltage waveforms into parameterized models for IM cells which can then be mapped into parameterized models for M cells. By applying this inversion for cells before and after a drug has been applied, we can estimate the effect of the drug on M cells. This procedure is first illustrated in FIG. 3 using simulated data. The inversion process is used to identify the theoretical effect of the drug, again in the case of verapamil and cisapride. From the left panel, we observe that the inversion algorithm is able to identify the effect of both verapamil and cisapride very accurately. This is consistent with the results of FIG. 2. The figure also shows the IM (middle panel) and M (right panel) action potentials and calcium transients. The M models are computed using the maturation map introduced in the Methods section.

Channel Block Identification Using MPS Data

Figure 4:
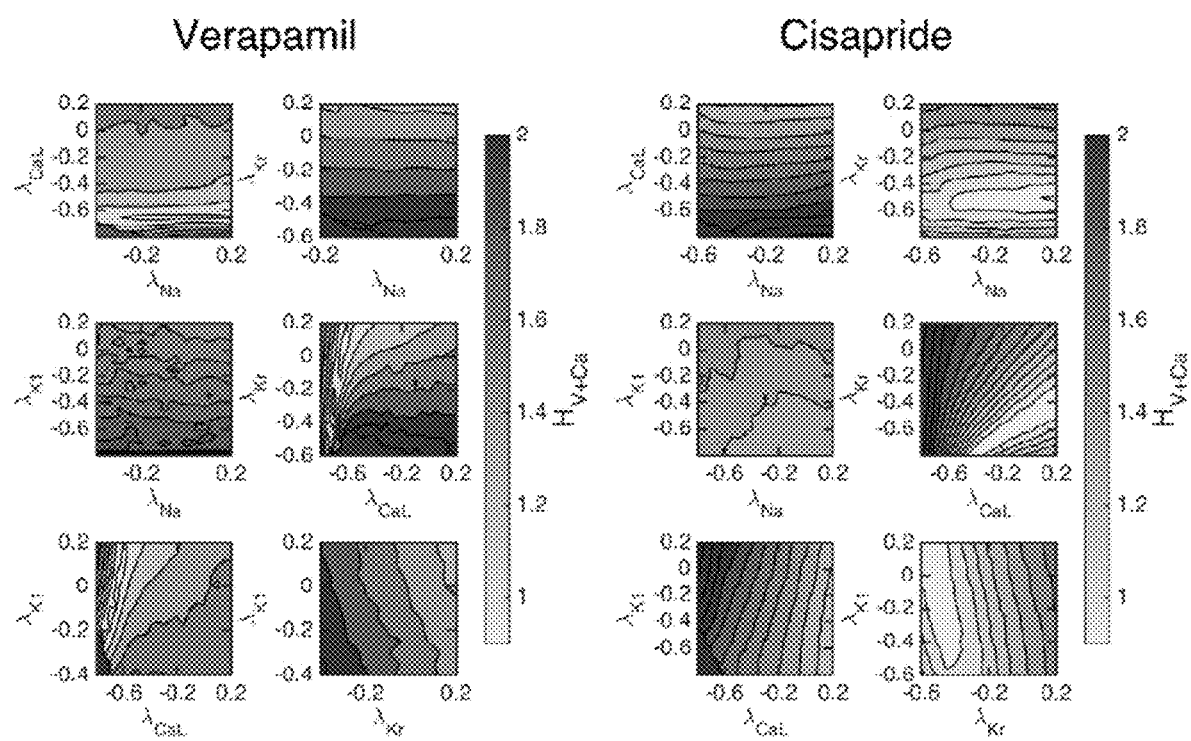
FIG. 4 shows that the cost function (8) in Example 1 (or (4) in Example 2) with ε=0.2 was evaluated for pairwise perturbations of maximum conductances using measured data from the MPS. Left panels: the effect of a dose of 100 nM of verapamil is shown; it clearly blocks $I_{caL}$ and it also blocks $I_{Kr}$. Right panels: the effect of a dose of 10 nM of cisapride is shown; it clearly blocks $I_{Kr}$. The results of the inversion are given in FIG. 5.

After demonstrating the theoretical sensitivity of inversion and drug effect prediction, we turn to the application of inverting actual cardiac MPS data. Average voltage and calcium traces (v,Ca)=(v(t),Ca(t)) from an MPS [3] were inverted to yield parameterized mathematical models of the IM cells. This was done first for control data, denoted by $(v^C, Ca^C)$ to yield a control model. We then show the sensitivity of the cost function $H_{V-Ca}$ comparing this model with obtained voltage and calcium waveforms under the effect of actual doses of verapamil and cisapride, $(v^D, Ca^D)$. In FIG. 4, we present pairwise perturbations of maximum conductances and we observe again that the cost function $H_{V+Ca}$ is sensitive to these perturbations. For verapamil, we see that the cost function clearly indicates that $I_{caL}$, is blocked by around 50%. Furthermore, $I_{Kr}$ seems to be blocked significantly, but it is not clear from the figure the extent of block. In the right panel, we also consider the effect of cisapride. Here, the cost function indicates that $I_{Kr}$ is blocked to a large extent.

The full inversion procedure (see the Methods section) is then applied, and it finds that $I_{CaL}$ is blocked by 71% and IKr is blocked by 19% (see FIG. 5) for verapamil, in rough agreement with known properties of verapamil at this dose. For cisapride, the inversion predicts that $I_{Kr}$ is blocked by 52%, and it predicts that the other currents are nearly unaffected by the drug.

Mature AP Change Prediction Using MPS Data

Figure 5:
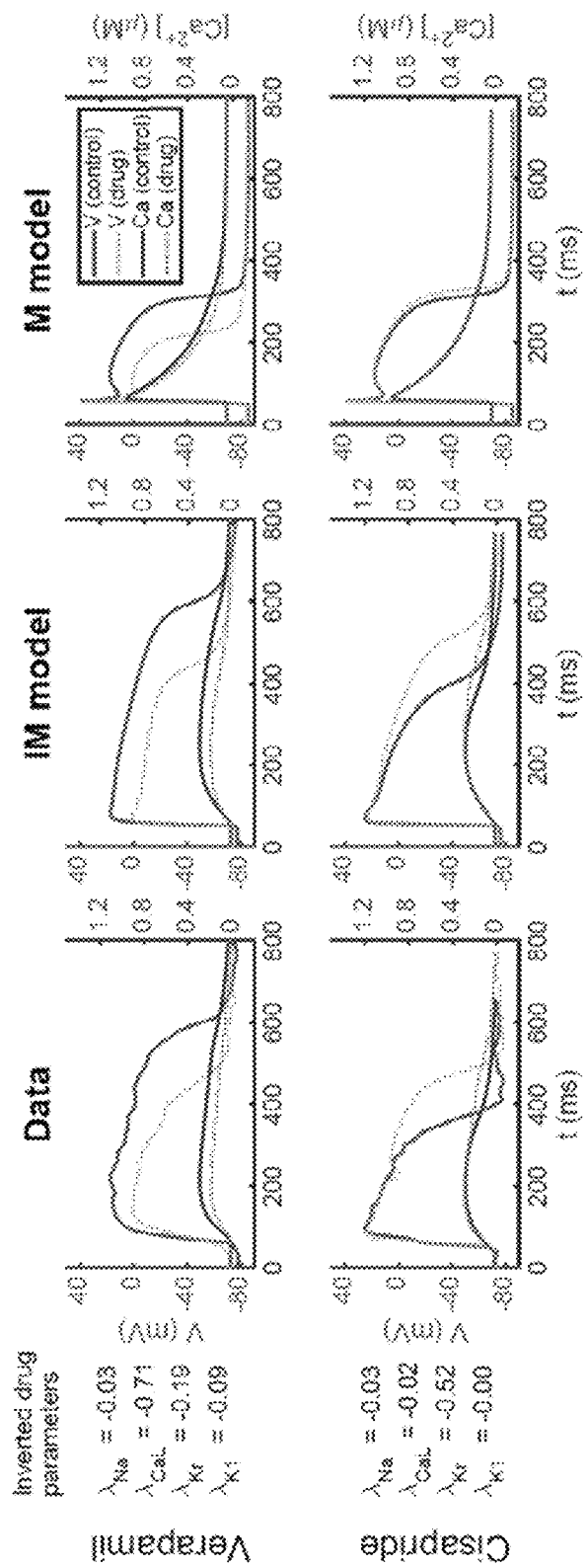
FIG. 5 shows results obtained by applying the inversion procedure to measured MPS data. First column: results of inversion by minimizing the cost function (8) in Example 1 (or (4) in Example 2) with ε=0.2. Second column: average voltage and calcium traces from MPS measurements. Third column: the AP model of the IM cells. Fourth column: the AP model of the M cells.

In Panel 1 (leftmost) of FIG. 5, we show the numeric results of inversion using measured data. The next three panels show action potentials and calcium transients for measured data (Panel 2), simulation of IM cells (Panel 3), and simulation of M cells (Panel 4). The simulations presented in Panel 3 are based on inversion of the MPS data giving the block values shown in Panel 1. The parameter vector (see the Methods section) representing the IM cells is multiplied by the maturation matrix in order to define the parameter vector representing the M cells. The figure illustrates how MPS measurements of IM cells can be used to estimate effect of an unknown compound for M cells.

Discussion

In this paper, we present a procedure to define the electrophysiological mechanisms of drug action in mature human cardiomyocytes based only on optical recordings of membrane potential and calcium in hiPSC-CMs. This procedure involves several important characteristics that overcome major existing challenges in hiPSC-CM-based screening. These are: (1) the inverse problem can be successfully applied to all-optical experimental data, thus allowing detailed pharmacologic characterization without the need for intracellular electrodes, (2) the mathematical approach to mapping between hiPSC-CM and adult myocyte electrophysiology is straightforward and generalizable, and (3) the MPS-based optical recordings are averaged over relatively large populations of hiPSC-CMs, thus reducing errors associated with the well-known phenotypic heterogeneity of hiPSC-CM preparations.

Inversion of Voltage and Calcium Traces Provide Action Potential Models

Modern cardiac AP models have been developed more or less continually since the celebrated sinoatrial node model of Noble [30]. As a result, a range of cardiac cellular models have evolved to represent the accumulated knowledge of nearly six decades of multidisciplinary research, and the models are, predictably, detailed and complex. Conventional approaches to developing these models have relied heavily upon voltage-clamp microelectrode data. These techniques provide exquisite resolution of single-channel [31, 32, 33, 34], through to whole-cell currents [35, 36, 37], and have thereby allowed the models to provide remarkably accurate reconstructions of all major cardiac cellular APs. However, these experimental methods are technically challenging, and thus intrinsically low-throughput. In modern clinical drug development pipelines, which leverage massive compound libraries, this presents a major shortcoming.

In the present report, we have developed an approach that attempts to use the decades of information stored in modern cardiac AP models to develop base models for hiPSC-CMs. However, it is important to note that the data obtained from an MPS are very different from the data traditionally used to develop AP models. Significantly, AP models are traditionally developed by inverting data from current measurements, but currents can presently not be measured in an MPS. In these systems, the transmembrane potential and the cytosolic calcium concentration can be measured. In addition, the extracellular potential can be measured and also the force the contraction of the IM cells exerts on elements of the micro tissue. But these data are fundamentally different from detailed measurements of single currents. Therefore, the problem of inversion must be addressed with other methods. The approach taken in this report is based on minimization of a cost function which seems to provide reasonable accuracy, but more accurate alternatives may become available. Clearly, independent of the problem of maturation, inversion of data from hiPSC-derived cells will be essential for understanding the electrophysiology of immature cells.

It was observed in FIG. 1 that the cost function $H_{V+Ca}$ is more sensitive than both $H_V$ and $H_{Ca}$ (see, (7)(8)). This indicates that both voltage and calcium traces must be measured in order to get optimal inversion of the measurements. However, this depends on the application. For instance, if the main purpose is to study side effects on the $I_{Kr}$ current, it may be sufficient to only consider voltage traces.

The Maturation Map

The idea of the maturation map is that the essential difference between an immature (IM) cell and a mature (M) cell is the number of proteins, the membrane area, and the volume of the cell and the intracellular storage structures. Based on these assumptions, we have argued that we can map any IM parameter vector, $p_{IM}$, to an associated M parameter vector, $p_M$, simply by multiplying by a diagonal matrix $Q: p_M = Q p_{IM}$. We have illustrated this mapping and noted that reasonable models of an IM AP are mapped over to a reasonable M AP. In addition, we have seen that measured IM data can be inverted to yield $p_{IM}$, and then the maturation mapping gives the adult AP parameterized by $p_M = Q p_{IM}$.

A more refined approach to maturation would be to take into account that proteins exist in various forms; for instance, the sodium channel has nine different forms with different associated possible channelopathies. These variants may proliferate at different rates and thus lead to significant changes in the properties of the M cells.

In the present report, we have simply addressed IM and M cells. Maturation is clearly a dynamic process with rapid changes, and it may therefore be of interest to model the time dependent behavior of the cells. Measurements of several time instances of IM cells may significantly improve the accuracy of the estimates.

hiPSC Data Sources

While our results show the promise of this methodology, considerable current limitations exist that need to be addressed. First, variability in hiPSC-CMs remains a challenge ([38, 39]). In the preparation of the data, we have dealt with variability by discarding voltage and calcium traces that are significantly different from the average behavior of the cells. This seems to give sufficient accuracy for inversion, and the effects of the drugs we have considered have shown significant cellular changes. However, even if the average results clearly respond to the doses of the drugs applied in this study, work on reducing the variability of generated hiPSC-CMs in MPSs is clearly needed.

In addition, improvements in data acquisition from the cell systems may also improve the methodology. In particular, it may increase the sensitivity of cost functions to currents that are presently less visible. For instance, the voltage waveform cannot currently be imaged at the time resolution needed to obtain accurate measurements of the upstroke, due to a combination of hardware and optical light collection limitations. In the same manner, the signal-to-noise ratio in this waveform, due to background dye absorption, prevents adequate resolution of the plateau phase and in particular of the notch in the action potential, preventing inversion of the $I_{to}$ current. Improvements in the methodology for collection of high resolution optical voltage data will therefore lead to substantial improvements in mapping resolution.

It should also be noted that it is possible to measure the extracellular field potential in the microphysiological systems using a multi-electrode array (MEA) system, see, e.g., [40, 1]. Such data can be incorporated in our method by using the EMI model (see, e.g., [41]) instead of the common AP models. In this case, the function H given by (8) would have to be extended to include the EFPs. This would be considerably more computationally demanding than the present method, but it may also increase the accuracy of the inversion.

Is there a Specie to Specie Mapping?

The basic idea underpinning the maturation mapping is that the proteins populating the cell membrane are the same for the IM cells and the M cells; the reason for the significant difference in AP between these cell types is the difference in densities of membrane proteins. Similarly, the proteins of the cell membranes are also quite similar from one specie to another, but again the densities of these proteins vary considerably. Therefore, the procedure for detecting side effects of drugs developed in this report may be generalized to be used between species. More specifically, it may be possible to measure the effect of drugs for mouse cells and deduce the effect for human cells following the steps detailed in the Method section below. This may be of significance because of the abundance of mouse data.

Methods

Our aim is to enable automatic characterization of the side effects of drugs for mature cardiomyocytes based on measurements of voltage and calcium traces of immature cells in an MPS. Here, we describe the methods applied above; we briefly describe how a model of the AP of a mature cardiomyocyte can be obtained from a model of an immature cardiomyocyte, how voltage and cytosolic calcium traces can be obtained from an MPS, and how these data are inverted in order to define a mathematical model of the AP of the immature cells. Furthermore, we describe how the effects of drugs on M cardiomyocytes can be estimated using measurements of the effect on IM cardiomyocytes.

Maturation is Multiplication

Our model of the maturation process relies on the assumption that the individual membrane proteins are functionally invariant under maturation, whereas the number of proteins, the membrane area and the cell volume change significantly (see, e.g., [42, 43, 44, 11]). Also, different membrane proteins proliferate at different rates leading to large differences in the expression levels between IM and M cells. This, in turn, leads to characteristic differences between the IM and M voltage and calcium traces. The maturation process is illustrated in FIG. 6.

A Drug Effects a Single Protein in the Same Manner for IM and M Cells

Since we assume that exactly the same proteins are present in the IM and the M cells, it follows that the effect of a given drug on a protein in the IM case is identical to the effect on the same protein type in an M cell. This observation is essential in order to understand side effects on M cells based on measurements of the IM cells.

The Membrane Potential for IM and M Cells in the Presence of a Single Current

In order to illustrate the modeling process going from IM to M, we consider the following simplest possible case where the transmembrane potential v (in mV) is governed by a single current $$Cv'(t) = -I, \quad (1)$$

with $I = go(v - v_0)$. Here, C is the membrane capacitance (in $\mu F/cm^2$), g is the maximum conductance (in $mS/cm^2$), o is the open probability of the channels (unitless), and $v_0$ is the resting potential of the channel (in mV). In this formulation, the current I is given in units of $\mu A/cm^2$. The maximum conductance can be written on the form $$g = \frac{Ng_0}{A}, \quad (2)$$

where $g_0$ is the conductance (in mS) of a single channel, N is the number of channels and A is the membrane area of the cell (in $cm^2$).

Let $N_{IM}$ and $A_{IM}$ denote the number of ion channels and the surface area of the IM cell, respectively. Then there are constants $q_N$ and $q_A$ such that the number of channels in the M cell is given by $N_M = q_N N_{IM}$, and the membrane area of the M cell is given by $A_M = q_A A_{IM}$. Therefore, the maximum conductance of the M cell can be expressed in terms of the maximum conductance of the IM cell as follows, $$g_M = \frac{N_m g_0}{A_M} = \frac{q_N N_{IM} g_0}{q_A A_{IM}} = \frac{q_N}{q_A} g_{IM} = q g_{IM} \quad (3)$$

with $q = \frac{q_N}{q_A}$.

Here, we have explained that the representation of a single current can be mapped from IM to M simply by multiplying the maximum conductance by a factor. This derivation relies heavily on the assumption that the dynamics of the single channel, represented by the open probability o in (2), remains the same during maturation (see, FIG. 6). As a consequence, the Markov model (see, e.g., [24]) representing the open probability of the single channel should be the same for the IM and the M version of the channel protein. Similar arguments can be presented for other membrane proteins such as exchangers and pumps. Furthermore, the intracellular calcium machinery can be treated in exactly the same manner, leaving the IM and M models of a single protein to be distinguished only by a factor. The factors for the individual components of an AP model can be gathered in a parameter vector p, and a diagonal matrix $Q$ can be used to store the maturation mapping from the IM parameter vector to the M parameter vector such that $p^M = Q p^{IM}$.

Figure 7:
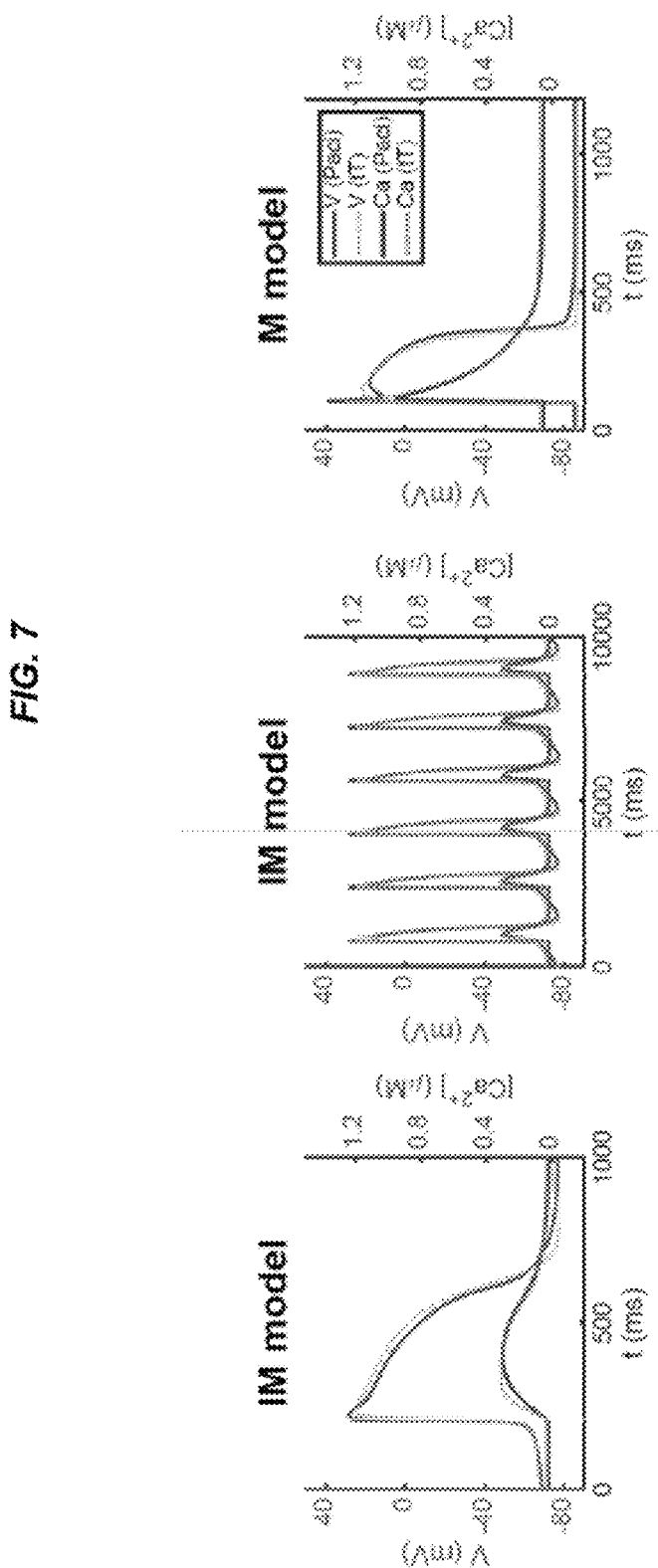
FIG. 7 shows immature and mature versions of the Paci et al. model [9] and the ten Tusscher et al. (tT) model [20]. The APs of the M cells are shorter and the upstroke velocity is faster than for the IM case, as can be seen by comparing the left and right panels. Also, the IM cells are pacemakers (middle panel), whereas the M cells reach a stable repolarized equilibrium after an AP (right panel).

In FIG. 7, we illustrate the use of the maturation mapping for well-established AP models of hiPSC-CMs using the Paci et al. model [9], and of the adult human cardiomyocyte using the ten Tusscher et al. model [20]. For the Paci et al. model, we define the maturation map $Q^P = \text{diag}(q_A/q_v, q_{Na}, q_{CaL}, q_{to}, q_{Ks}, q_{Kr}, q_{K1}, q_{NaCa}, q_{NaK}, q_{pCa}, q_f, q_{bNa}, q_{bCa}, q_{leak}, q_{up}, q_{rel}) = (1.7, 0.5, 2.5, 10, 1, 0.25, 3, 0.3, 0.7, 1, 0.1, 0.32, 0.85, 200, 0.95, 35)$. Since $p_{IM}$ is given by the paper [9], we can compute $p^M = Q p^{IM}$. Similarly, for the ten Tusscher et al. model we use $Q^T = \text{diag}(q_A/q_v, q_{Na}, q_{caL}, q_{to}, q_{Ks}, q_{Kr}, q_{K1}, q_{NaCa}, q_{NaK}, q_{pCa}, q_{pK}, q_{bNa}, q_{bCa}, q_{leak}, q_{up}, q_{rel}) = (1.7, 0.3, 2.5, 5, 10, 1.2, 50, 0.58, 0.7, 2, 0.5, 0.3, 0.85, 200, 0.6, 20)$, and since $p^M$ is given by the paper [20], we can compute the IM version by $p^{IM} = Q^{T-1} p^M$.

We observe that these AP models have the known characteristic differences between IM and M cells; the upstroke of the IM cells are considerably slower than for the M cells, the IM cells are pacemaker cells (middle panel of FIG. 7), and the M cell reaches a stable equilibrium (right panel of FIG. 7).

Estimating Side Effects of Drugs

The method for identifying side effects of drugs is summarized in Table 1. The method involves eight steps:

Step 1: Base model. Assume that there exists an AP base model, characterized by a parameter vector $p^{IM,B}$, representing a prototypical IM cell, and an associated base maturation map $Q^B$. The associated M cells are characterized by $p^M = Q^B p^{IM,B}$. The M model, parameterized by $p^M$, provides a normal mature AP. No drug is involved in parameterizing the base model. Note also that the base model is used for numerous (independent) measurements. The base model in our computations is a modified version of the model of hiPSC-CMs suggested by Paci et al. [9].

Step 2 and 3: MPS-measurements. For the IM cells, we measure the transmembrane potential and the cytosolic calcium concentration, stored as $(v^C, c^C)$, and make similar measurements for the case when a drug has been applied, stored as $(V^D c^D)$. Here C is for control (no drug) and D is for drug.

Step 4 and 5: Inversion. Generally, the notation $$(v, c) \xrightarrow{\text{inversion}(q)} p \quad (4)$$

means that the data (v, c) are inverted to yield a model parameterized by the vector p, using the model parameterized by the vector q as a starting point for the inversion. The control data (no drug) given by $(v^C, c^C)$ are inverted to yield the model parameterized by $p^{IM,C}$, using the parameter vector $p^{IM,B}$ as a starting point for the inversion. Likewise, the D-data are inverted to give the model $p^{IM,D}$, where the parameter vector $p^{IM,C}$ is used as a starting point.

Step 6: Update maturation map. The maturation map can now be updated to secure that if $Q$ is applied to the IM parameter vector, $p^{IM,C}$, the resulting parameter vector is the base model of the M cell parameterized by the vector $p^M$.

Step 7: Map from IM to M. The updated maturation map $Q$ is used to compute the parameterization of the M version of the drugged cells.

Step 8: Drug affected M cell. The effect of the drug on the M cells is analyzed by comparing the vectors $p^M$ and $p^{M,D}$. The components of $p^{M,D}$ that are significantly different from its $p^M$ counterpart, are those that have been significantly affected by the drug. The effect of the drug on the mature AP is estimated by comparing the result of simulations of the models characterized by $p^M$ and $p^{M,D}$.

TABLE 1

Summary of the method for computing possible side effects of drugs for mature cells based on measurements conducted on immature hiPSC-derived cells.

| | | |
|---|---|---|
| 1 | Base Model | $p^M = Q^B p^{IM,B}$ |
| 2 | Measure control (C), no drug | $(v^C, c^C)$ |
| 3 | Measure with drug (D) applied | $(v^D, c^D)$ |
| 4 | Invert C-data | $(v^C, c^C) \xrightarrow{\text{inversion}(p^{IM,B})} p^{IM,C}$ |
| 5 | Invert D-data | $(v^D, c^D) \xrightarrow{\text{inversion}(p^{IM,C})} p^{IM,D}$ |
| 6 | Update maturation map | $Q p^{IM,C} = p^M$ |
| 7 | Paramaterize M version of D cells | $p^{M,D} = Q p^{IM,D}$ |
| 8 | Compare M version of C and D cells | Simulate M cells with $p^{M,D}$ and $p^M$ |

Inversion of Voltage and Cytosolic Calcium Traces

In order to complete the description of the steps presented in Table 1, we need to explain how the inversion used in steps 4 and 5 is performed, and the key question is how to do the inversion of the form (4). In order to explain this, we assume that we have a base model of the form $$v_t = \Sigma_i q_i I_i(v, s), \quad (5)$$

where $I_i$ represents the dynamics of the individual membrane proteins and $q_i$ represents the maximum conductance of the ion channels (or the maximum rate of an exchanger or a pump). Furthermore, v is the transmembrane potential and s represents the remaining state variables of the model. In order to adjust this model to a set of measured data given by (v,c), we seek parameters $\lambda_i$ such that the solution of $$v_t = \Sigma (1 + \lambda_i) q_i I_i(v, s), \quad (6)$$

is as close as possible to the measured data, $(\bar{v}, \bar{c})$. The distance from the computed solution $(v,c)=(v(\lambda),c(\lambda))$ to the measured data $(\bar{v}, \bar{c})$ is given by a cost function $H=H(\lambda)$.

We consider the following cost functions $$H_V(\lambda) = \left(\sum_{j=1}^{4} H_j(\lambda) + \varepsilon \sum_i \lambda_i^2\right)^{1/2}, \quad (7)$$

$$H_{Ca}(\lambda) = \left(\sum_{j=5}^{8} H_j(\lambda) + \varepsilon \sum_i \lambda_i^2\right)^{1/2},$$

$$H_{V+Ca}(\lambda) = \left(\sum_{j=1}^{8} H_j(\lambda) + \varepsilon \sum_i \lambda_i^2\right)^{1/2}, \quad (8)$$

where $$H_1 = \frac{\left|\int_{t_0(\lambda)}^{t_1(\lambda)} v(\lambda) dt - \int_{t_0^*}^{t_1^*} v^* dt\right|}{\left|\int_{t_0^*}^{t_1^*} v^* dt\right|},$$

$$H_2 = \frac{|APD_{V,30}(\lambda) - APD_{V,30}^*|}{|APD_{V,30}^*|},$$

$$H_3 = \frac{|APD_{V,50}(\lambda) - APD_{V,50}^*|}{|APD_{V,50}^*|},$$

$$H_4 = \frac{|APD_{V,80}(\lambda) - APD_{V,80}^*|}{|APD_{V,80}^*|},$$

$$H_5 = \frac{\left|\left(\frac{dc}{dt}\right)_{max}(\lambda) - \left(\frac{dc}{dt}\right)_{max}^*\right|}{\left|\left(\frac{dc}{dt}\right)_{max}^*\right|},$$

$$H_6 = \frac{|APD_{Ca,30}(\lambda) - APD_{Ca,30}^*|}{|APD_{Ca,30}^*|},$$

$$H_7 = \frac{|APD_{Ca,50}(\lambda) - APD_{Ca,50}^*|}{|APD_{Ca,50}^*|},$$

$$H_8 = \frac{|APD_{Ca,80}(\lambda) - APD_{Ca,80}^*|}{|APD_{Ca,80}^*|}.$$

Here, the star is used to denote observed data, either generated by simulations or gathered from the MPS. Also, $(dc/dt)_{max}$ is the maximal upstroke velocity of the calcium concentration. Furthermore, $APD_{V,30}$ is defined as the length (in ms) of the time from the value of the transmembrane potential, in the upstroke, is 30% below its maximum value $(t_0)$ until it again is repolarized to 30% of its maximum value $(t_1)$. The values $APD_{V,50}$ and $APD_{V,80}$ are defined similarly. Likewise, the terms $APD_{Ca,30}$, $APD_{Ca,50}$ and $APD_{Ca,80}$ represent the corresponding transient durations for the calcium concentration. In $H_1$, we compute the integral of the transmembrane potential from $t=t_0$ to $t=t_1$. Note that $H_V$ only depends on characteristics of the voltage trace, whereas $H_{Ca}$ only depends on characteristics of the calcium trace; finally, $H_{V+Ca}$ includes the terms of both the two former cost functions and therefore depends on the characteristics of both the voltage trace and the calcium trace.

The Minimization Procedure

The inversion procedure aims to minimize the cost function measuring the difference between the target and model voltage and calcium waveforms. In every minimization, we have an existing parameter vector $\bar{p}$, and we seek an optimal perturbation of this vector where each component is given by $(1+\lambda_i)\bar{p}_i$. Here, i runs over the components of the parameter vector and $\lambda_i$ denotes the perturbation. The cost function introduced above is irregular and hard to minimize. Therefore, we introduce a brute force search algorithm that avoids any attempt to take the gradient into account. To start searching for suitable values of $\lambda=\{\lambda_i\}$, we first set up a bounding box of allowed values of $\lambda$. This is initially set up so that each $\lambda_i$ is in some interval, for instance [−0.5, 0.5]. Next, we draw N choices of $\lambda$ randomly from the bounding box and compute $H(\lambda)$ for each of these N choices. We then pick out the five choices of that give the smallest values of $H(\lambda)$ and set up a new bounding box of reduced size around each of these five choices of $\lambda$. More specifically, these bounding boxes are set up by centering the boxes around the chosen $\lambda$ and letting the length of the interval for each $\lambda_i$ be reduced to 90% of the length of the previous intervals. Note that this means that the new bounding boxes are not necessarily contained in the initial bounding box, but may extend beyond the initial intervals. We do, however, set up a restriction so that no bounding box is allowed to contain values of $\lambda$ smaller than or equal to −1. In addition, when searching for the effect of drugs, we assume that the drug is a channel blocker and therefore only consider $\lambda \in (-1,0]$.

After setting up the five new bounding boxes, we draw N/5 choices of $\lambda$ randomly from each box and compute $H(\lambda)$ for each of these N choices of $\lambda$. We then select the five choices of that give the smallest values of $H(\lambda)$ and repeat the steps above for a given number of iterations. For the applications of the minimization method reported in the Results section, we generally use 10 iterations and N=5000.

Measuring Voltage and Calcium Traces Using an MPS

Using previously developed techniques [3], cardiac MPS systems were loaded and matured prior to drug exposure. On the day upon which studies were performed, freshly measured drug was dissolved into DMSO (i.e., for cisapride) or media (i.e., for verapamil) and serially diluted. Each concentration of the drug to be tested was preheated for 15-20 minutes in a water bath at 37° C. and subsequently sequentially injected in the device. At each dose, after 10 minutes of exposure, the drug's response on the microtissue was recorded using a Nikon Eclipse TE300 microscope fitted with a QImaging camera. Fluorescent images were acquired at 100 frames per second using GCaMP and BeRST-1 across the entire chip for 6-8 seconds.

Fluorescence videos were analyzed using custom Python software utilizing the open source Bio-Formats tool to produce characteristic voltage and calcium waveforms for each chip and tested drug dose. Briefly, for each analysis, the fluorescent signal for the entire visual field was averaged, excluding pixels which did not change significantly in intensity over the acquisition. The signal was then smoothed using a 3 point median filter, and 5-7 individual action potentials or calcium transients were overlaid by aligning the maximum dF/dt and then averaged into a single transient.

REFERENCES

[1] Hiroyuki Ando, Takashi Yoshinaga, Wataru Yamamoto, Keiichi Asakura, Takaaki Uda, Tomohiko Taniguchi, Atsuko Ojima, Raku Shinkyo, Kiyomi Kikuchi, Tomoharu Osada, Seiji Hayashi, Chieko Kasai, Norimasa Miyamoto, Hiroyuki Tashibu, Daiju Yamazaki, Atsushi Sugiyama, Yasunari Kanda, Kohei Sawada, and Yuko Sekino. A new paradigm for drug-induced torsadogenic risk assessment using human ips cell-derived cardiomyocytes. *Journal of Pharmacological and Toxicological Methods*, 84(Supplement C):111-127, 2017.

[2] Luca Sala, Milena Bellin, and Christine L Mummery. Integrating cardiomyocytes from human pluripotent stem cells in safety pharmacology: has the time come? *British journal of pharmacology*, 2016.

[3] Anurag Mathur, Peter Loskill, Kaifeng Shao, Nathaniel Huebsch, SoonGweon Hong, Sivan G Marcus, Natalie Marks, Mohammad Mandegar, Bruce R Conklin, Luke P Lee, and Kevin E. Healy. Human ipsc-based cardiac microphysiological system for drug screening applications. *Scientific reports*, 5:8883, 2015.

[4] John P Wikswo. The relevance and potential roles of microphysiological systems in biology and medicine. *Experimental biology and medicine*, 239(9):1061-1072, 2014.

[5] Eric W Esch, Anthony Bahinski, and Dongeun Huh. Organs-on-chips at the frontiers of drug discovery. *Nature reviews. Drug discovery*, 14(4):248, 2015.

[6] Yosuke K Kurokawa and Steven C George. Tissue engineering the cardiac microenvironment: Multicellular microphysiological systems for drug screening. *Advanced drug delivery reviews*, 96:225-233, 2016.

[7] Renjun Zhu, Adriana Blazeski, Ellen Poon, Kevin D. Costa, Leslie Tung, and Kenneth R. Boheler. Physical developmental cues for the maturation of human pluripotent stem cell-derived cardiomyocytes. *Stem Cell Research & Therapy*, 5(5):117, October 2014.

[8] Junyi Ma, Liang Guo, Steve J Fiene, Blake D Anson, James A Thom-son, Timothy J Kamp, Kyle L Kolaja, Bradley J Swanson, and Craig T January. High purity human-induced pluripotent stem cell-derived cardiomyocytes: electrophysiological properties of action potentials and ionic currents. *American Journal of Physiology-Heart and Circulatory Physiology*, 301(5):H2006H2017, 2011.

[9] Michelangelo Paci, Jari Hyttinen, Katriina Aalto-Setala, and Stefano Severi. Computational models of ventricular- and atrial-like human induced pluripotent stem cell derived cardiomyocytes. *Annals of biomedical engineering*, 41(11):2334-2348, 2013.

[10] Jie Liu, Zachary Laksman, and Peter H Backx. The electrophysiological development of cardiomyocytes. *Advanced drug delivery reviews*, 96:253-273, 2016.

[11] Fikru B Bedada, Matthew Wheelwright, and Joseph M Metzger. Maturation status of sarcomere structure and function in human ipsc-derived cardiac myocytes. *Biochimica et Biophysica Acta (BBA)-Molecular Cell Research*, 1863 (7): 1829-1838, 2016.

[12] Jingqi Q. X. Gong and Eric A. Sobie. Population-based mechanistic modeling allows for quantitative predictions of drug responses across cell types. *bioRxiv*, 2017.

[13] Ping Liang, Feng Lan, Andrew S Lee, Tingyu Gong, Veronica Sanchez-Freire, Yongming Wang, Sebastian Diecke, Karim Sallam, Joshua W Knowles, Patricia K Nguyen, et al. Drug screening using a library of human induced pluripotent stem cell-derived cardiomyocytes reveals disease specific patterns of cardiotoxicity. *Circulation*, pages CIRCULATIONAHA-113, 2013.

[14] Anurag Mathur, Zhen Ma, Peter Loskill, Shaheen Jeeawoody, and Kevin E Healy. In vitro cardiac tissue models: Current status and future prospects. *Advanced drug delivery reviews*, 96:203-213, 2016.

[15] Yoram Rudy and Jonathan R Silva. Computational biology in the study of cardiac ion channels and cell electrophysiology. *Quarterly Reviews of Biophysics*, 39(01):57-116, 2006.

[16] Yoram Rudy. From genes and molecules to organs and organisms: Heart. *Comprehensive Biophysics*, pages 268-327, 2012.

[17] Zhilin Qu, Gang Hu, Alan Garfinkel, and James N Weiss. Nonlinear and stochastic dynamics in the heart. *Physics Reports*, 543(2), 2014.

[18] Thomas O'Hara, Laszl'o' Virag,' Andras' Varro,' and Yoram Rudy. Simulation of the undiseased human cardiac ventricular action potential: Model formulation and experimental validation. *PLoS Computational Biology*, 7(5):e1002061, 2011.

[19] Eleonora Grandi, Francesco S. Pasqualini, and Donald M. Bers. A novel computational model of the human ventricular action potential and Ca transient. *Journal of Molecular and Cellular Cardiology*, 48(1): 112-121, 2010.

[20] K H W J ten Tusscher, D Noble, P J Noble, and Alexander V Panfilov. A model for human ventricular tissue. *American Journal of Physiology-Heart and Circulatory Physiology*, 286(4):H1573H1589, 2004.

[21] K H W J Ten Tusscher and A V Panfilov. Cell model for efficient simulation of wave propagation in human ventricular tissue under nor-mal and pathological conditions. *Physics in medicine and biology*, 51(23):6141, 2006.

[22] Colleen E. Clancy, Zheng I. Zhu, and Yoram Rudy. Pharmacogenetics and anti-arrhythmic drug therapy: A theoretical investigation. *AJP: Heart and Circulatory Physiology*, 292(1):H66H75, 2007.

[23] Jonathan D Moreno and Colleen E Clancy. Using computational modeling to predict arrhythmogenesis and antiarrhythmic therapy. *Drug Discovery Today: Disease Models*, 6(3):71-84, 2009.

[24] Aslak Tveito and Glenn T Lines. *Computing Characterizations of Drugs for Ion Channels and Receptors Using Markov Models*. Springer-Verlag, Lecture Notes, vol. 111, 279 pages, 2016.

[25] Michelangelo Paci, Elisa Passini, Stefano Severi, Jari Hyttinen, and Blanca Rodriguez. Phenotypic variability in 1qt3 human induced pluripotent stem cell-derived cardiomyocytes and their response to anti-arrhythmic pharmacological therapy: an in silico approach. *Heart Rhythm*, 2017.

[26] Dongrui Ma, Heming Wei, Yongxing Zhao, Jun Lu, Guang Li, Norl-iza Binte Esmail Sahib, Teng Hong Tan, Keng Yean Wong, Winston Shim, Philip Wong, et al. Modeling type 3 long qt syndrome with cardiomyocytes derived from patient-specific induced pluripotent stem cells. *International journal of cardiology*, 168(6):5277-5286, 2013.

[27] Azra Fatima, Shao Kaifeng, Sven Dittmann, Guoxing Xu, Manoj K Gupta, Matthias Linke, Ulrich Zechner, Filomain Nguemo, Hendrik Milting, Martin Farr, et al. The disease-specific phenotype in cardiomyocytes derived from induced pluripotent stem cells of two long qt syndrome type 3 patients. *PloS one*, 8(12):e83005, 2013.

[28] Kirsi Kujala, Jere Paavola, Anna Lahti, Kim Larsson, Mari Pekkanen-Mattila, Matti Viitasalo, Annukka M Lahtinen, Lauri Toivonen, Kimmo Kontula, Heikki Swan, et al. Cell model of catecholaminergic polymorphic ventricular tachycardia reveals early and delayed afterdepolarizations. *PloS one*, 7(9):e44660, 2012.

[29] William J. Crumb, Jose Vicente, Lars Johannesen, and David G. Strauss. An evaluation of 30 clinical drugs against the comprehen-sive in vitro proarrhythmia assay (cipa) proposed ion channel panel. *Journal of Pharmacological and Toxicological Methods*, 81(Supple-ment C):251-262, 2016. Focused Issue on Safety Pharmacology.

[30] Denis Noble. A modification of the HodgkinHuxley equations applicable to Purkinje fibre action and pacemaker potentials. *The Journal of Physiology,* 160(2):317-352, 1962.

[31] Bert Sakmann and Erwin Neher, editors. *Single-Channel Recording.* Springer, 2nd edition, 1995.

[32] D. Colquhoun and A. G. Hawkes. On the stochastic properties of bursts of single ion channel openings and of clusters of bursts. *Philosophical Transactions of the Royal Society London B,* 300:1-59, 1982.

[33] Ivo Siekmann, James Sneyd, and Edmund J. Crampin. MCMC Can Detect Nonidentifiable Models. *Biophysical Journal,* 103(11):2275-2286, December 2012.

[34] Aslak Tveito, Glenn Lines, Andrew G Edwards, and Andrew D Mc-Culloch. Computing rates of markov models of voltage-gated ion channels by inverting partial differential equations governing the probability density functions of the conducting and non-conducting states. *Mathematical Biosciences,* doi. org/10.1016/j.mbs.2016.04.011, 2016.

[35] A L Hodgkin and A F Huxley. The components of membrane conductance in the giant axon of loligo. *The Journal of physiology,* 116(4):473-496, 1952.

[36] Meron Gurkiewicz and Alon Korngreen. A Numerical Approach to Ion Channel Modelling Using Whole-Cell Voltage-Clamp Recordings and a Genetic Algorithm. *PLoS Computational Biology,* 3 (8): 1633-1647, August 2007.

[37] Willemijn Groenendaal, Francis A Ortega, Armen R Kherlopian, Andrew C Zygmunt, Trine Krogh-Madsen, and David J Christini. Cell-specific cardiac electrophysiology models. *PLoS computational biology,* 11(4): e1004242, 2015.

[38] Renjun Zhu, Michal A Millrod, Elias T Zambidis, and Leslie Tung. Variability of action potentials within and among cardiac cell clusters derived from human embryonic stem cells. *Scientific reports,* 6, 2016.

[39] Daniel Ortmann and Ludovic Vallier. Variability of human pluripotent stem cell lines. *Current opinion in genetics & development,* 46:179-185, 2017.

[40] Keiichi Asakura, Seiji Hayashi, Atsuko Ojima, Tomohiko Taniguchi, Norimasa Miyamoto, Chiaki Nakamori, Chiho Nagasawa, Tetsuo Ki-tamura, Tomoharu Osada, Yayoi Honda, et al. Improvement of acquisition and analysis methods in multi-electrode array experiments with ips cell-derived cardiomyocytes. *Journal of pharmacological and toxicological methods,* 75:17-26, 2015.

[41] Aslak Tveito, Karoline Horgmo Jxger, Miroslav Kuchta, Kent-Andre Mardal, and Marie E. Rognes. A cell-based framework for numeri-cal modeling of electrical conduction in cardiac tissue. *Frontiers in Physics,* 5:48, 2017.

[42] Bertil Hille. *Ion channels of excitable membranes,* volume 507. Sinauer Sunderland, M A, 2001.

[43] H Sontheimer, B R Ransom, and S G Waxman. Different na+ currents in p0- and p7-derived hippocampal astrocytes in vitro: evidence for a switch in na+ channel expression in vivo. *Brain research,* 597(1):24-29, 1992.

[44] William J Moody and Martha M Bosma. Ion channel development, spontaneous activity, and activity-dependent development in nerve and muscle cells. *Physiological reviews,* 85(3):883-941, 2005.

Example 2

Inversion and Computational Maturation of Drug Response Using Human Stem Cell Derived Cardiomyocytes in Microphysiological Systems This example describes how, according to methods of the present invention, a mathematical framework is used to invert optical measurements of drug effects in human iPSC-derived cardiomyocytes (hiPSC-CMs) into predictions of ion channel block and electrophysiological dynamics in adult cardiomyocytes.

Abstract

While cardiomyocytes differentiated from human induced pluripotent stems cells (hiPSCs) hold great promise for drug screening, the electrophysiological properties of these cells can be variable and immature, producing results that are significantly different from their human adult counterparts. Here, we describe a computational framework to address this limitation, and show how in silico methods, applied to measurements on immature cardiomyocytes, can be used to both identify drug action and to predict its effect in mature cells. Our synthetic and experimental results indicate that optically obtained waveforms of voltage and calcium from microphysiological systems can be inverted into information on drug ion channel blockage, and then, through assuming functional invariance of proteins during maturation, this data can be used to predict drug induced changes in mature ventricular cells. Together, this pipeline of measurements and computational analysis significantly improves the ability of hiPSC derived cardiomycocytes to predict dangerous drug side effects.

Introduction

The discovery of human induced pluripotent stem cells (hiPSCs) has started a new era in biological science and medicine. These reprogrammed somatic cells can be differentiated into a wide variety of cell lineages, and allow in vitro examination of cellular properties at the level of the human individual. In particular, this technology has large implications in drug development, moving us away from well-studied but often unrepresentative animal models towards direct testing of compounds in specific human phenotypes and genotypes. This new access offers the potential for creating more cost effective, better, safer drug treatments; both from the ability to target precision, patient specific approaches, and to reveal possible side effects of drugs in the broader human population. However, despite its promise, the technology needed to fully utilize hiPSCs for drug testing is still under development and currently faces many difficulties limiting practical applicability.

In particular, the problem of maturation is a major challenge to the successful use of hiPSCs in drug discovery and development. Although hiPSCs can be used to create specialized human cells and tissues, these rapidly grown cells and tissues may have significant proteomic and structural differences to, and are often more fetal-like than, their adult in vivo counterparts. This is especially true in hiPSC derived cardiomyocytes (hiPSC-CMs), where the adult cells they are intended to represent have undergone decades of growth and development under cyclical physiological loading and stimulation. However, despite this limitation, hiPSC-CMs have already been successfully used to assess unwanted side effects of drugs (see, e.g., [1, 2]), and new technologies such as microphysiological systems (MPS) [3], are emerging to improve maturation and better capture drug effects. Still, the overall applicability of hiPSC-CMs to find unwanted side effects of drugs for adult cardiomyocytes remains limited by the fact that only relatively immature cells are available for analysis (see, e.g., [4, 5, 6, 7]). And, as pointed out in numerous papers (e.g., [8, 9, 10, 11, 12]), the electrophysiological characteristics of hiPSC-CMs and adult cardiomyocytes differ significantly and, for determining potential dangerous drug side-effects, these differences may lead to both false positives and false negatives (see, e.g., [13, 3]).

Meanwhile, in silico methods for investigating the properties of the action potential (AP) of excitable cells is a well developed field (see, e.g., [14, 15, 16]) and includes models of human cardiomyocytes (see, e.g., [17, 18, 19, 20]), and models where the effect of drugs are taken into account (see, e.g., [21, 22, 23]). Also, mathematical models of the action potential of hiPSC-CMs have been developed (see, e.g., [9, 24]) based on measurements reported in [8, 25, 26, 27]. This field has progressed to the point where computational models are now an active part of cardiotoxicity research [28], and are being integrated into guidelines for comprehensive drug arrhythmia analysis.

In this example, we discuss how computational models of immature (IM) and mature (M) cardiomyocytes contribute to the improvement of the applicability of exploiting hiPSCs in the drug development pipeline. Despite remarkable progress in handling hiPSC-CMs under lab conditions (see, e.g., [29]), the ability to create fully mature hiPSC-CMs for drug screening is likely to remain a significant challenge. Here, we therefore address how in silico computational modeling can be used to deduce properties of mature (adult) cardiomyocytes based on two real time measurements of their immature counterpart.

A key idea in our approach is that individual proteins are functionally invariant under maturation. Therefore, maturation is multiplication in the sense that, for every type of protein, the number of proteins multiply during maturation, but the function of every protein remains unaltered. In addition, the surface area of the cell and the cell volume also increase significantly during maturation, leading to large changes in current densities between the IM and M cells. The invariance of the functional properties of the IM and M versions of every protein suggests a proportionality between the associated individual currents of the IM and M cells which may explain the results obtained in [12]. We use the proportionality between the individual currents to define a maturation matrix that maps the parameterization of a model of the IM cell to a parameterization of a model of the M cell.

Figure 8:
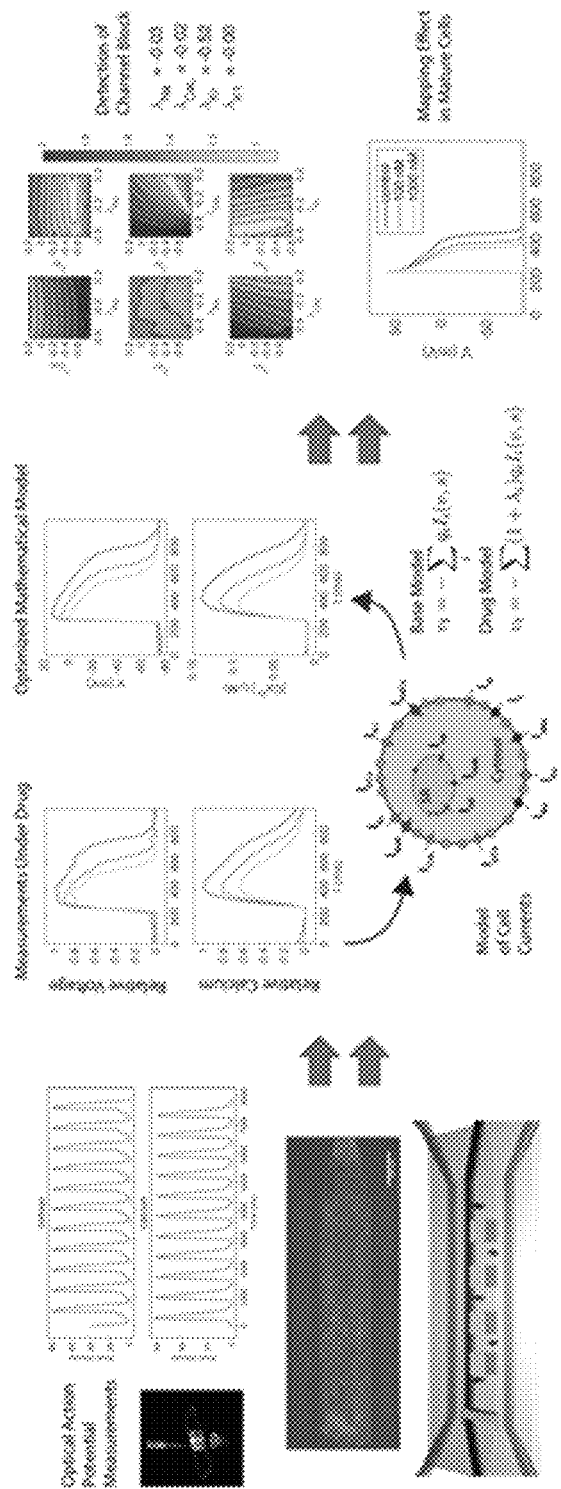
FIG. 8 shows a depiction of in silico modeling and analysis of an MPS system. Optical measurements of calcium and voltage are taken at baseline and in the presence of drug. These waveforms are inverted using a mathematical model of cell dynamics, into a set of parameters that define key ion channel conductances. Changes in this parameter set give information about specific changes in conductances under drug, and this parameter set can then be mapped to a model of mature cell behavior using the assumption of functional invariance of individual channels.

According to methods of the present invention, the effects of drugs on M cells is estimated based on measurements of IM cells, which can be summarized as follows and as shown in FIG. 8:

1. A MPS system is used to collect time averaged voltage and intracellular (cystolic) calcium waveforms, both under control conditions and in the presence of drug.
2. These voltage and calcium traces are inverted in order to define a mathematical model of the membrane and calcium dynamics of the tested IM cells. The effect of the drug is reflected in terms of changes in the maximum conductances of ion channels in the model.
3. The IM models are multiplied by a maturation matrix in order to obtain models for the M cells. The effect of the drug for adult cells is estimated by comparing the AP models of the M cells.

To demonstrate this process, we start by showing that a cost function, measuring the difference between data and model, is sensitive with respect to changes in the maximum conductance of major currents. Next, we show that this sensitivity is sufficient to invert simulated data and obtain a mathematical model of a drug effect. This model can be mapped from the IM case to the M case simply by multiplying a parameter vector by a diagonal maturation matrix. Finally, we apply the method of inversion to obtain an IM model based on experimental data obtained using voltage- and calcium-sensitive dyes in an MPS. Again, the IM model is mapped to an M model. The effects of drugs are identified by inverting MPS data (voltage and cytosolic calcium concentration) and then mapping the resulting model from IM to M giving a mathematical model of the mature cardiomyocytes under the influence of a drug.

Results
Model Inversion is Sensitive to Perturbations in Major Ion Channel Currents The inversion of data through the minimization of a cost function requires that this cost function is sensitive to changes in model parameters. In FIG. 1, we illustrate the sensitivity of three cost functions utilizing voltage, calcium, or both, to perturbations in the conductances of major cellular currents or fluxes. Here the base model (see Methods) is defined by a modified version of the Paci et al. model [9].

The results indicate that the cost function using voltage alone, $H_V$, is sensitive to only some of the currents and fluxes, and in particular, it is largely insensitive to changes in $I_{to}$ and $I_{Ks}$. Similar trends are seen in the calcium mismatch, $H_{Ca}$, and this cost function is, in general, less sensitive than the $H_V$ version. Finally, we consider the cost function combining both the voltage and calcium data, $H_{V+Ca}$, and observe that it is more sensitive to perturbations than both $H_V$ and $H_{Ca}$ alone, although some currents are still largely invisible.

Of note the maximum upstroke velocity of the action potential is not added as a part of the $H_V$ cost function. Adding this component would likely improve sensitivity, especially for the sodium current, but our measurements (see Methods) do not at present provide sufficient accuracy of the upstroke velocity. However, the upstroke velocity of the calcium transient can be accurately estimated from the MPS measurements and is therefore a part of the cost function describing the calcium mismatch.

Simulated Channel Block Identification

Although FIG. 1 shows the sensitivity of the computed cost functions with respect to individual currents, we need to establish that the cost functions are adequately sensitive when multiple currents are allowed to vary. In FIG. 2, we show the values of $H_{V+Ca}$ as a function of pairwise perturbations in the maximum conductances of four major channels. The traces are theoretically computed using known effects of two chosen drugs; verapamil which blocks $I_{caL}$ and $I_{Kr}$, and cisapride which blocks $I_{Kr}$ [28].

Our results indicate that the cost function using both voltage and calcium can theoretically identify the simulated channel block of the chosen drugs. The left panels show the value of $H_{V+Ca}$ as a function of the perturbation of the maximum conductances when the drug data are computed using the specified blocking due to the application of verapamil. Six different configurations of pairwise blocking perturbations were tested and a minimum is clearly obtained close to the correct blocking of $I_{caL}$ and $I_{Kr}$. Meanwhile, in the right panel, we show the values of $H_{V+Ca}$ when $I_{Kr}$ is blocked by 50%, simulating the effect of cisapride. The pairwise perturbations clearly identify that IKr is blocked by around 50%. These results indicate that an optimization algorithm of the cost function could find unique minima corresponding to specific channel blocks.

Simulated Drug Effect Identification Using the Inversion Procedure

Figure 9:
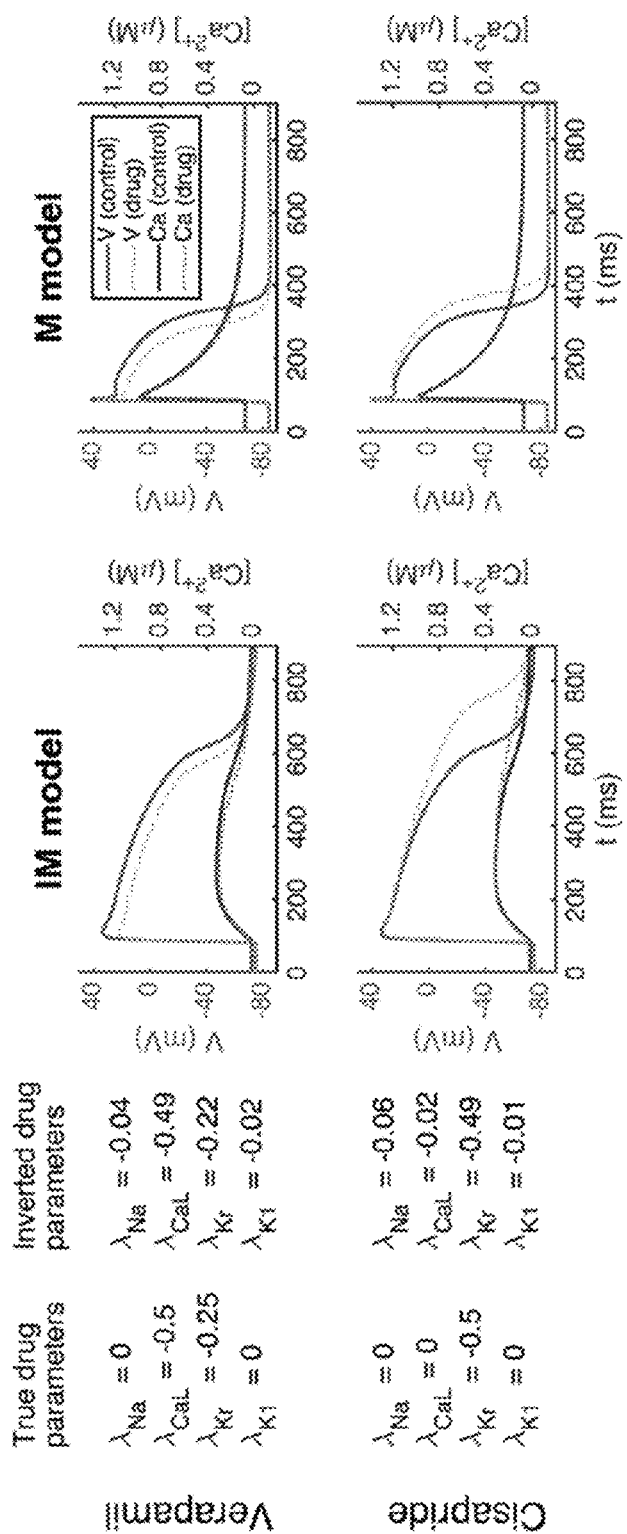
FIG. 9 shows identification of drug effects on M cells based on simulated data of IM cells. Left panel: Results of inversion by minimizing the cost function (4) in Example 2 with ε=0.2. Middle panel: Action potential and calcium transient before and after (dotted) the drug is applied. Right panel: Model results after application of the maturation matrix.

Our methodology for inversion and mapping from the IM to the M state is first illustrated in FIG. 9 using simulated data. This process is used to identify the theoretical effect of the two drugs of verapamil and cisapride on mature cells from waveforms that would be obtained from known channel blocking. From the left panel, we observe that the inversion algorithm is able to identify the specified effect of both verapamil and cisapride very accurately, reproducing chosen blocks nearly exactly. This is consistent with the results of FIG. 2. The figure also shows the IM (middle panel) and M (right panel) action potentials and calcium transients. The M models are computed using the maturation map introduced in the Methods section showing how these detected blocks would appear in mature cells.

Identification of Simulated Channel Block of Major and Mi-Nor Currents

Figure 10:
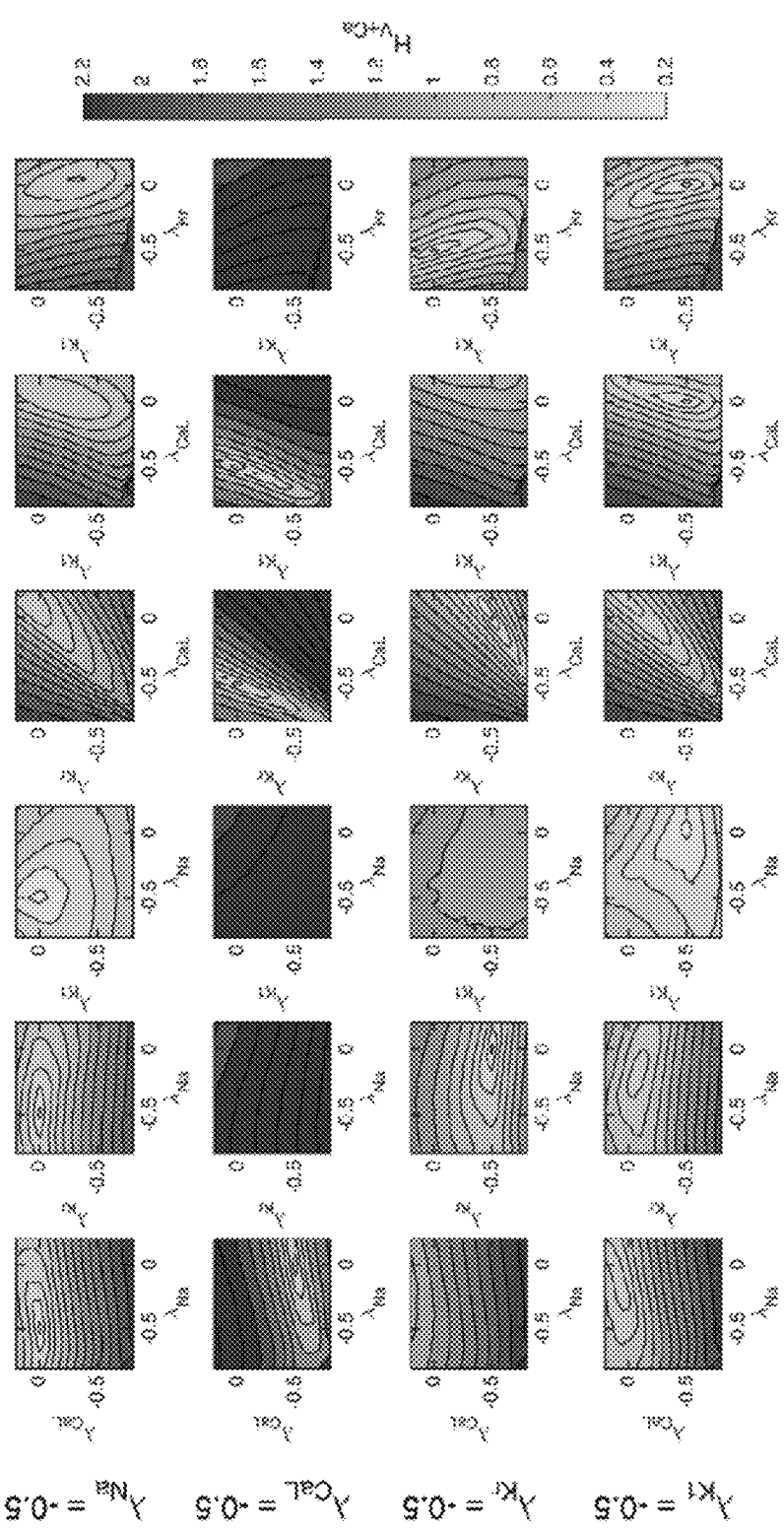
FIG. 10 shows The cost function (4) in Example 2 with ε=0.2 evaluated for pairwise perturbations of the maximum conductances of four major currents for simulated single-channel block of each of the currents. In the upper panel, $I_{Na}$ is blocked by 50%, and in the next panels, $I_{caL}$, $I_{Kr}$, and $I_{K1}$ are similarly blocked by 50%. Like in FIG. 2, clear minimums are observed at the correct blockages in all four cases.

FIG. 2 demonstrates using simulated data that the cost function $H_{V+Ca}$ is able to theoretically identify induced changes to the $I_{Kr}$ and $I_{caL}$ currents. In FIG. 10, we extend this analysis to consider 50% single channel block of each of the major currents $I_{Na}$, $I_{caL}$, $I_{Kr}$, and $I_{K1}$. Again, we show the values of $H_{V+Ca}$ for pairwise perturbations of the maximum conductance of these four currents.

FIG. 10 indicates that the cost function $H_{V+Ca}$ is theoretically able to identify each of the simulated single channel blocks. On the other hand, we expected that the cost function might fail to identify channel block of some of the minor, less sensitive membrane currents, for example $I_{to}$ and $I_{Ks}$, which both have low sensitivity values in FIG. 1. In Table 2, we rank the currents by their total inward and outward contributions to the action potential, and report how well the inversion algorithm was able to identify simulated 10%, 30%, 50%, and 70% single-channel block of these currents. We observed that the inversion algorithm was not able to correctly identify the block of the smaller contributing currents $I_{to}$ and $I_{Ks}$, but identified the block of $I_{K1}$, $I_{caL}$, $I_{Kr}$, and $I_{Na}$ quite accurately for the investigated channel blockings.

TABLE 2

Identification of simulated single-channel block of six currents and four levels of block.

| | ∫\|I\|dt (nC/μF) | $\lambda = -0.1$ | $\lambda = -0.3$ | $\lambda = -0.5$ | $\lambda = -0.7$ |
|---|---|---|---|---|---|
| $I_{K1}$ | 388.3 | −0.08 | −0.30 | −0.47 | −0.69 |
| $I_{CaL}$ | 225.1 | −0.13 | −0.32 | −0.58 | −0.71 |
| $I_{Kr}$ | 187.0 | −0.11 | −0.28 | −0.50 | −0.70 |
| $I_{Na}$ | 119.4 | −0.11 | −0.32 | −0.47 | −0.68 |
| $I_{to}$ | 12.6 | 0.00 | 0.00 | −0.15 | −0.27 |
| $I_{Ks}$ | 3.6 | 0.00 | 0.00 | −0.05 | −0.10 |

We used the cost function $H_{V+Ca}$ defined in (4) with ε=0.2. The second column of the table reports the integral of the absolute value of each of the currents in the unperturbed case, and the last four columns report the estimated channel blocks returned by the inversion algorithm for each single-channel block. In all cases, the conductance of all six currents was allowed to vary in the inversion procedure.

Channel Block Identification Using a Combined In Vitro/In Silico System

After demonstrating the theoretical sensitivity of inversion and drug effect prediction, we turn to the application of inverting actual cardiac MPS data. Average voltage and calcium traces (v, Ca)=(v(t), Ca(t)) from an MPS [3] were inverted to yield parameterized mathematical models of the IM cells. This was done first for control data, denoted by ($v^C$, $Ca^C$) to yield a control model. We then show the sensitivity of the cost function $H_{V-Ca}$ comparing this model with obtained voltage and calcium waveforms under the effect of actual doses of ver-apamil and cisparide, ($v^D$, $Ca^D$). In FIG. 4, we present pairwise perturbations of maximum conductances and we observed again that the cost function $H_{V+Ca}$ is sensitive to these perturbations. For verapamil, we saw that the cost function clearly indicates that $I_{caL}$ is blocked by around 50%. Furthermore, $I_{Kr}$ seems to be blocked significantly, but it is not clear from the figure the extent of the block. In the right panel, we also consider the effect of cisapride. Here, the cost function indicates that $I_{Kr}$ is blocked to a large extent.

The full inversion procedure (see the Methods section) is then applied, and it finds that $I_{caL}$ is blocked by 71% and $I_{Kr}$ is blocked by 19% (see FIG. 5) for verapamil, in rough agreement with known properties of verapamil at this dose. For cisapride, the inversion predicted that $I_{Kr}$ is blocked by 52%, and it predicted that the other currents are nearly unaffected by the drug.

Mature AP Change Prediction Using MPS Data

In Panel 1 (leftmost) of FIG. 5, we show the numeric results of inversion using measured data. The next three panels show action potentials and calcium transients for measured data (Panel 2), simulation of IM cells (Panel 3) and simulation of M cells (Panel 4). The simulations presented in Panel 3 are based on inversion of the MPS data giving the block values shown in Panel 1. The parameter vector (see the Methods section) representing the IM cells was multiplied by the maturation matrix in order to define the parameter vector representing the M cells. The figure illustrates how MPS measurements of IM cells are used to estimate the effect of an unknown compound for M cells.

Discussion

In this example, we present a mathematical analysis framework to define the electro-physiologic mechanisms of drug action in mature human cardiomyocytes using only optical recordings of membrane potential and calcium in hiPSC-CMs. This procedure overcame a number of major existing challenges in hiPSC-CM-based screening: (1) data inversion of measured drug effects can be successfully applied to all-optical experimental data, thus allowing detailed pharmacologic characterization without the need for intracellular electrodes, (2) the mathematical approach to mapping between hiPSC-CM and adult myocyte electro-physiology is straightforward and generalizable, and (3) the MPS-based optical recordings are averaged over relatively large populations of hiPSC-CMs, thus reducing errors associated with the well-known phenotypic heterogeneity of hiPSC-CM preparations.

Inversion of Voltage and Calcium Traces into Action Potential Models

Modern cardiac AP models have been developed more or less continually since the celebrated sinoatrial node model of Noble [30]. As a result, a range of cardiac cellular models have evolved to represent the accumulated knowledge of nearly six decades of multidisciplinary research, and the models are detailed and complex. Conventional approaches to developing these models have relied heavily upon voltage-clamp microelectrode data. These techniques provide exquisite resolution of single-channel [31, 32, 33, 34], through to whole-cell currents [35, 36, 37], and have thereby allowed the models to provide remarkably accurate reconstructions of cardiac cellular APs and calcium dynamics. However, while generalized cell models built using such data are widely used, especially to mechanistically understand how drug compounds alter electrophysiology, the experimental methods used to build them are technically challenging, have intrinsically low throughput and cannot be used on tissue models like MPS.

In this example, we have developed an alternative approach that attempts to exploit the decades of information stored in modern cardiac AP models to rapidly parameterize base models for hiPSC-CMs. Rather than the data traditionally used to develop AP models, we used metrics that can readily be measured in an MPS, namely the optically assessed transmembrane potential and cytosolic calcium concentration. However, these data are fundamentally different from the detailed measurements of single currents traditionally used to invert measurements into biophysical models, and new methodology is needed. The approach taken in this example is based on minimization of a cost function comparing the predicted and measured waveforms, which provides reasonable accuracy in analysis, but it is clear that some currents are still largely invisible even theoretically, and alternative approaches may lead to broader or more focused results.

For example, it was observed in FIG. 1 that the cost function $H_{V+Ca}$ is more sensitive than both $H_V$ and $H_{Ca}$ (see (3)(4)). This indicates that both voltage and calcium traces must be measured in order to get optimal inversion of the measurements. However, this depends on the application. For instance, if the main purpose is to study side effects on the $I_{Kr}$ current, it may be sufficient to only consider voltage traces. In addition, cost functions which take into account measured extracellular potential or contractile force generated by the IM cells may also be used to better invert specific drug induced changes.

Uniqueness of Conductance Defined Action Potential Models

One significant question is the uniqueness of the parameters obtained in inversion of the optical waveforms, as mathematical models of excitable tissue often exhibit non unique behavior. For example, in models of neurons it is well known that different cell models can provide similar neuronal activity, see, e.g., [38, 39, 40]. Similar observations have been made for a variety of models of cardiac cells, in [41] using the ten Tusscher et al. model [42], and in [43] using the O'Hara et al. model [17]. The implication of these observations is that it is generally very challenging to uniquely determine conductances from AP observations, and indeed, it has clearly been demonstrated that single action potential waveforms can have multiple conductance parameterizations that a give low fit error when many parameters are allowed to vary [37]. Several methods have been tried to solve this problem; see, e.g., [44, 45], and promising approaches have been suggested by a number of groups. For example, in [41] it was shown that using several physical properties of the dynamics improves the invertibility of the conductances. More recently, optimized voltage-clamping protocols [37] have been introduced to give better resolution of smaller currents and more uniquely determine conductances. We see in our results the same lack of uniqueness, especially when we try to invert smaller currents such $I_{to}$ and $I_{Ks}$. However, we are able to observe that four major currents appear largely visible and invertible with a combined measure of voltage and calcium from a single paced waveform and a CPU-intensive method that avoids the differentiation of a rough cost-function.

Using Correlations for Parametrization and Mapping

Others have also approached the question of how to map changes in cardiac dynamics between populations using model results. In a series of papers (see [46, 41, 47, 48, 12]) by Sobie and co-authors, a comprehensive theory has been developed for using correlations between simulation results to parameterize models and for mapping between species, and between immature and mature cells. Starting in [46], it is observed that input parameters such as maximum conductances of ion currents are correlated with output parameters such as the APD and the net amplitude of the calcium transient. Such correlations are useful because they can be used to understand how natural variability of input parameters affects output characteristics in populations of cell models. The correlations can also, in principle, be used for parameterization by measuring output characteristics and use the inverse correlation matrix to parameterize input parameters.

In [12], the correlation is taken one step further by observing that output parameters from simulations of one species are correlated to the output parameters of simulations based on a model of another species. Similarly, the authors observe that simulation outputs from a model of immature cells are correlated with output results of simulations based on a model of mature cells. Therefore, it is, in principle, possible to perform measurements of immature data and map the results to the mature case.

The correlation approach to mapping between species and between immature and mature cells is highly promising. However, the theory is based on observed correlations between simulated data and provide no mechanistic insight into the relations. In our approach, it follows directly from the assumptions that the proteins are the same for immature and mature cells, that there must be a mapping between models of immature and mature cells.

The Maturation Map

While the inversion of data from hiPSC-derived cells is essential for understanding the electrophysiology of immature cells, understanding how such electrophysiolgical changes translate into mature cells provides powerful means to screen drugs for side effects. We introduced the idea of a maturation map, which assumes that the essential difference between an immature (IM) cell and a mature (M) cell can be described by the number of proteins, the membrane area and the volume of the cell and the intracellular storage structures. Based on these assumptions, we have argued that we can map any IM parameter vector, $p_{IM}$, to an associated M parameter vector, $p_M$, simply by multiplying by a diagonal matrix Q: $p_M = Qp_{IM}$. We have illustrated this mapping and noted that reasonable models of an IM AP are mapped over to a reasonable M AP. In addition, we have seen that measured IM data can be inverted to yield $p_{IM}$, and then the maturation mapping gives the adult AP parameterized by $p_M = Qp_{IM}$.

In this example, we have simply addressed the mapping directly from an IM state to the M cells. However, maturation is clearly a dynamic process with rapid changes, and it may therefore be of interest to use this mapping to investigate the time-dependent behavior of the cells. Measurements of several time instances of IM cells gives insight into the developmental trajectories of hiPSC-CMs and how different maturation protocols alter the electrophysiological properties of generated test cells. Such studies are useful for both choosing maturation protocols to optimize data inversion sensitivity, and for quality control measures of batch to batch cells.

In addition, taking into account more aspects of cellular electrophysiology can be used to refine our approach. For example, one can take into account that proteins exist in various forms; for instance, the sodium channel has nine different forms with different associated possible channelopathies. These variants may proliferate at different rates and thus potentially lead to significant changes in the properties of the M cells.

hiPSC Data Sources

While our results show the promise of this methodology, considerable current limitations exist that need to be addressed. First, variability in hiPSC-CMs remains a challenge ([49, 50]). In the preparation of the data, we have dealt with variability by discarding individual voltage and calcium traces that are significantly different from the average behaviour of the cells. This gives sufficient accuracy for inversion, and the effects of the drugs we have considered have shown significant cellular changes. However, even if the average results clearly respond to the doses of the drugs applied in this study, work on reducing the variability of generated hiPSC-CMs in MPSs is beneficial for batch to batch consistency.

In addition, improvements in data acquisition from the cell systems may also improve the methodology, in particular it may increase the sensitivity of cost functions to currents that are presently less visible. For instance, the voltage waveform cannot currently be imaged at the time resolution needed to obtain accurate measurements of the upstroke, due to a combination of hardware and optical light collection limitations. In the same manner, the signal-to-noise ratio in this waveform, due to background dye absorption, prevents adequate resolution of the plateau phase and in particular of the notch in the action potential, preventing inversion of the $I_{to}$ current. Improvements in the methodology for collection of high resolution optical voltage data will therefore lead to substantial improvements in mapping resolution.

It should also be noted that it is possible to measure the extracellular field potential in the microphysiological systems using a multi-electrode array (MEA) system, see, e.g., [51, 1]. Such data can be incorporated in our method by using the EMI model (see, e.g., [52]) instead of the common AP models. In this case, the function H given by (4) would have to be extended to include the EFPs. This would be considerably more computationally demanding than the present method, but it may also increase the accuracy of the inversion.

Extension to Species—Species Mapping

The basic idea underpinning the maturation mapping is that the proteins populating the cell membrane are the same for the IM cells and the M cells; the reason for the significant difference in AP between these cell types is the difference in densities of membrane proteins. Similarly, the proteins of the cell membranes are also quite similar from one species to another, but again the densities of these proteins vary considerably. Therefore, the procedure for detecting side effects of drugs developed in this example may be generalized to be used between species. More specifically; it is possible to measure the effect of drugs for mouse cells and deduce the effect for human cells following the steps detailed in the Method section below. This is useful because of the abundance of mouse data.

Methods

Our aim was to enable automatic characterization of side effects of drugs for mature cardiomyocytes based on measurements of voltage and calcium traces of immature cells in an MPS. Here, we describe the methods applied above; we briefly explain how appropriate optical measurements of voltage and calcium are obtained, how a model of the AP of a mature cardiomyocyte can be obtained from a model of an immature cardiomyocyte, and how data is inverted to define a mathematical model of the AP of immature cells. Furthermore, we describe how the effects of drugs on M cardiomyocytes can be estimated using measurements of the effect on IM cardiomyocytes.

Measuring Voltage and Calcium Traces Using an MPS

Using previously developed techniques [3], cardiac MPS systems were loaded and matured prior to drug exposure. On the day upon which studies were performed, freshly measured drug was dissolved into DMSO (cisapride) or media (verapamil) and serially diluted. Each concentration of the drug to be tested was preheated for 15-20 min in a water bath at 37° C. and subsequently sequentially injected in the device. At each dose, after 5 min of exposure, the drug's response on the microtissue was recorded using a Nikon Eclipse TE300 microscope fitted with a QImaging camera. Fluorescent images were acquired at 100 frames per second using filters to capture GCaMP and BeRST-1 fluorescence as previously described. Images were obtained across the entire chip for 6-8 seconds, with cell excitation paced at 1 Hz, to capture multiple beats for processing.

Fluorescence videos were analyzed using custom Python software utilizing the open source Bio-Formats tool to produce characteristic voltage and calcium waveforms for each chip and tested drug dose. Briefly, for each analysis, the fluorescent signal for the entire visual field was averaged, excluding pixels which did not change significantly in intensity over the acquisition. The signal was then smoothed using a 3 point median filter, and 5-7 individual action potentials or calcium transients overlayed by aligning the maximum dF/dt and then averaged into a single transient.

Inversion of Voltage and Cytosolic Calcium Traces

In order to complete the description of the steps presented in Table 1 (see, Example 1 above), we need to explain how the inversion used in steps 4 and 5 is performed, and the key question is how to do the inversion. To this end, we assume that we have a base model of the form $$v_t = -\Sigma_i q_i I_i(v,s) \quad (1),$$

where $I_i$ represents the dynamics of the individual membrane proteins and $q_i$ represents the maximum conductance of the ion channels (or the maximum rate of an exchanger or a pump). Furthermore, v is the transmembrane potential and s represents the remaining state variables of the model. In order to adjust this model to a set of measured data given by $(v^*, c^*)$, we seek parameters $\lambda_i$ such the solution of $$v_t = \Sigma(1+\lambda_i) q_i I_i(v,s) \quad (2)$$

is as close as possible to the measured data, $(v^*, c^*)$. The distance from the computed solution $(v, c) = (v(\lambda X), c(\lambda))$ to the measured data $(v^*, c^*)$ is given by a cost function $H = H(\lambda)$.

We consider the following cost functions $$H_V(\lambda) = \left( \sum_{j=1}^{4} H_j(\lambda) + \varepsilon \sum_i \lambda_i^2 \right)^{1/2}, \quad (3)$$

$$H_{Ca}(\lambda) = \left( \sum_{j=5}^{8} H_j(\lambda) + \varepsilon \sum_i \lambda_i^2 \right)^{1/2} \text{ and}$$

-continued $$H_{V+Ca}(\lambda) = \left(\sum_{j=1}^{8} H_j(\lambda) + \varepsilon \sum_i \lambda_i^2\right)^{1/2}. \quad (4)$$

where $$H_1 = \frac{\left|\int_{t_0(\lambda)}^{t_1(\lambda)} v(\lambda)dt - \int_{t_0^*}^{t_1^*} v^* dt\right|}{\left|\int_{t_0^*}^{t_1^*} v^* dt\right|},$$

$$H_2 = \frac{|APD_{V,30}(\lambda) - APD_{V,30}^*|}{|APD_{V,30}^*|},$$

$$H_3 = \frac{|APD_{V,50}(\lambda) - APD_{V,50}^*|}{|APD_{V,50}^*|},$$

$$H_4 = \frac{|APD_{V,80}(\lambda) - APD_{V,80}^*|}{|APD_{V,80}^*|},$$

$$H_5 = \frac{\left|\left(\frac{dc}{dt}\right)_{max}(\lambda) - \left(\frac{dc}{dt}\right)_{max}^*\right|}{\left|\left(\frac{dc}{dt}\right)_{max}^*\right|},$$

$$H_6 = \frac{|APD_{Ca,30}(\lambda) - APD_{Ca,30}^*|}{|APD_{Ca,30}^*|},$$

$$H_7 = \frac{|APD_{Ca,50}(\lambda) - APD_{Ca,50}^*|}{|APD_{Ca,50}^*|},$$

$$H_8 = \frac{|APD_{Ca,80}(\lambda) - APD_{Ca,80}^*|}{|APD_{Ca,80}^*|}.$$

Here, the star * is used to denote observed data, either generated by simulations or gathered from the MPS. Also, $(dc/dt)_{max}$ is the maximal upstroke velocity of the calcium concentration. Furthermore, $APD_{V,30}$ is defined as the length (in ms) of the time from the value of the transmembrane potential, in the upstroke, is 30% below its maximum value ($t_0$) until it again is repolarized to 30% of its maximum value (t1). The values $APD_{V,50}$ and $APD_{V,80}$ are defined similarly. Likewise, the terms $APD_{Ca,30}$, $APD_{Ca,50}$ and $APD_{Ca,80}$ represent the corresponding transient durations for the calcium concentration. In $H_1$, we compute the integral of the transmembrane potential from $t=t_0$ to $t=t_1$. Note that $H_V$ only depends on characteristics of the voltage trace, whereas $H_{Ca}$ only depends on characteristics of the calcium trace; finally, $H_{V+Ca}$ includes the terms of both the two former cost functions and therefore depends on the characteristics of both the voltage trace and the calcium trace.

The Minimization Procedure

The inversion procedure aims to minimize the cost function measuring the difference between the target and model voltage and calcium waveforms. In every minimization, we have an existing parameter vector $\bar{p}$, and we seek an optimal perturbation of this vector where each component is given by $(1+\lambda_i)\bar{p}_i$. Here, i runs over the components of the parameter vector and $\lambda_i$ denotes the perturbation.

The cost function introduced above is irregular and hard to minimize. Therefore, we introduce a brute force search algorithm that avoids any attempt to take the gradient into account. To start searching for suitable values of $\lambda=\{\lambda_i\}$, we first set up a bounding box of allowed values of $\lambda$. This is initially set up so that each $\lambda_i$ is in some interval, for instance [−0.5, 0.5]. Next, we draw N choices of $\lambda$ randomly from the bounding box and compute $H(\lambda)$ for each of these N choices. We then pick out the five choices of $\lambda$ that give the smallest values of $_H(\lambda)$ and set up a new bounding box of reduced size around each of these five choices of $\lambda$. More specifically, these bounding boxes are set up by centering the boxes around the chosen $\lambda$ and letting the length of the interval for each k, be reduced to 90% of the length of the previous intervals. Note that this means that the new bounding boxes are not necessarily contained in the initial bounding box, but may extend beyond the initial intervals. We do, however, set up a restriction so that no bounding box is allowed to contain values of $\lambda$ smaller than or equal to −1. In addition, when searching for the effect of drugs, we assume that the drug is a channel blocker and therefore only consider $\lambda \in (-1, 0]$.

After setting up the five new bounding boxes, we draw N/5 choices of $\lambda$ randomly from each box and compute $H(\lambda)$ for each of these N choices of $\lambda$. We then select the five choices of $\lambda$ that give the smallest values of $H(\lambda)$ and repeat the steps above for a given number of iterations. For the applications of the minimization method reported in the Results section, we generally use 10 iterations and N=5000.

Maturation through Multiplication

Our model of the maturation process relies on the assumption that the individual membrane proteins are functionally invariant under maturation, whereas the number of proteins, the membrane area and the cell volume change significantly (see, e.g., [53, 54, 55, 11]). Also, different membrane proteins proliferate at different rates leading to large differences in the expression levels between IM and M cells. This, in turn, leads to characteristic differences between the IM and M voltage and calcium traces. The maturation process is illustrated in FIG. 6.

A Drug Effects a Single Protein in the Same Manner for IM and M Cells

Since we assume that exactly the same proteins are present in the IM and M cells, it follows that the effect of a given drug on a protein in the IM case is identical to the effect on the same protein type in a M cell. This observation is essential in order to understand side effects on M cells based on measurements of the IM cells.

The Membrane Potential for IM and M Cells in the Presence of a Single Current

In order to illustrate the modeling process going from IM to M, we consider the following simplest possible case where the transmembrane potential v (in mV) is governed by a single current $$Cv'(t) = -I \quad (5),$$

with $I=g_o(v-v_0)$. Here, C is the membrane capacitance (in $\mu F/cm^2$), g is the maximum conductance of the channels (in $mS/cm^2$), o is the open probability of the channels (unitless), and $v_0$ is the resting potential of the channels (in mV). In this formulation, the current I is given in units of $\mu A/cm^2$. The maximum conductance can be written on the form $$g = \frac{Ng_0}{A}, \quad (6)$$

where $g_0$ is the conductance (in mS) of a single channel, N is the number of channels and A is the membrane area of the cell (in $cm^2$).

Let $N_{IM}$ and $A_{IM}$ denote the number of ion channels and the surface area of the IM cell, respectively. Then there are constants $q_N$ and $q_A$ such that the number of channels in the M cell is given by $N_M=q_N N_{IM}$, and the membrane area of the M cell is given by $A_M=q_A A_{IM}$. Therefore, the maximum conductance of the M cell can be expressed in terms of the maximum conductance of the IM cell as follows, $$g_M = \frac{N_m g_0}{A_M} = \frac{q_N N_{IM} g_0}{q_A A_{IM}} = \frac{q_N}{q_A} g_{IM} = q g_{IM} \quad (7)$$

$$\text{with } q = \frac{q_N}{q_A}.$$

Here, we have explained that the representation of a single current can be mapped from IM to M simply by multiplying the maximum conductance by a factor. This derivation relies heavily on the assumption that the dynamics of the single channel, represented by the open probability o in (6), remains the same during maturation (see, FIG. 6). As a consequence, the Markov model (see, e.g., [23]) representing the open probability of the single channel should be the same for the IM and the M version of the channel protein. Similar arguments can be presented for other membrane proteins such as exchangers and pumps. Furthermore, the intracellular calcium machinery can be treated in exactly the same manner, leaving the IM and M models of a single protein to be distinguished only by a factor.

The factors for the individual components of an AP model can be gathered in a parameter vector p, and a diagonal matrix $Q$ can be used to store the maturation mapping from the IM parameter vector to the M parameter vector such that $p_M = Q p_{IM}$.

Figure 11:
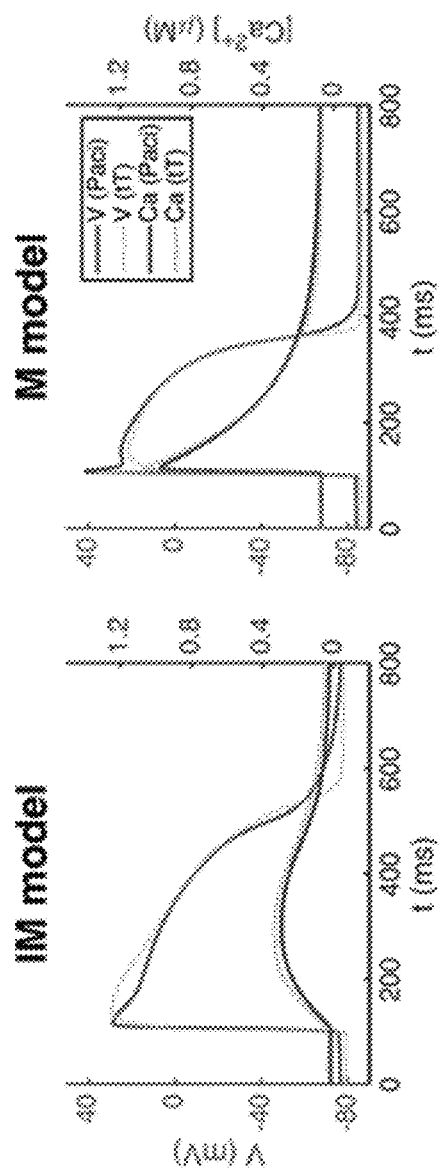
FIG. 11 shows immature and mature versions of the Paci et al. model (reference [9] in Example 2) and the ten Tusscher et al. (tT) model (reference [19] in Example 2). The APs of the M cells are shorter and the upstroke velocity of the calcium transient is faster than for the IM case; compare left and right panels.

In FIG. 11, we illustrate the use of the maturation mapping for well-established AP models of hiPSC-CMs using the Paci et al. model [9], and of the adult human cardiomyocyte using the ten Tusscher et al. model [19]. For the Paci et al. model, we define the maturation map $Q_P = \text{diag}(q_A/q_v, q_{Na}, q_{CaL}, q_{to}, q_{Ks}, q_{Kr}, g_{K1}, q_{NaCa}, q_{NaK}, q_{pCa}, q_f, q_{bNa}, q_{bCa}, q_{leak}, q_{up}, q_{rel}) = (1.7, 0.4, 3, 5, 20, 0.7, 1.3, 0.05, 0.3, 0.6, 0.1, 0.5, 0.4, 200, 1, 36)$. Since $p_{IM}$ is given by the paper [9], we can compute $p_M = !_p p_{IM}$. Similarly, for the ten Tusscher et al. model we use $Q_T = \text{diag}(q_A/q_v, q_{Na}, q_{CaL}, q_{to}, q_{Ks}, q_{Kr}, q_{K1}, q_{NaCa}, q_{NaK}, q_{pCa}, q_f, q_{pK}, q_{bNa}, q_{bCa}, q_{leak}, q_{up}, q_{rel}) = (1.7, 4, 4.2, 17, 40, 1, 2.2, 0.4, 0.7, 1.7, 0.05, 19, 0.1, 0.6, 500, 1.3, 34)$, and since $p_M$ is given by the paper [19], we can compute the IM version by $p_{IM} = Q_T^{-1} p_M$. The maturation maps are set up using an extended version of the standard inversion procedure described above with characteristics of the currents $I_{Na}$, $I_{caL}$, $I_{Kr}$, and $I_{K1}$ included in the cost function.

We observe that these AP models display characteristic differences between IM and M cells; the upstroke of calcium transient of the IM cells is considerably slower than for the M cells, and the action potential duration is longer for the IM cells than for the M cells.

Estimating Side Effects Drugs

The method for identifying side effects of drugs is summarized in Table 2. The method involves eight steps:

Step 1: Base model Assume that there exists an AP base model, characterized by a parameter vector $p^{IM,B}$, representing a prototypical IM cell, and an associated base maturation map $Q^B$. The associated M cells are characterized by $p^M = Q^B p^{IM,B}$. The M model, parameterized by $p^M$, provides a normal mature AP. No drug is involved in parameterizing the base model. Note also that the base model is used for numerous (independent) measurements. The base model in our computations is a modified version of the model of hiPSC-CMs suggested by Paci et al. [9].

Steps 2 and 3: MPS-measurements For the IM cells, we measure the transmembrane potential and the cytosolic calcium concentration, stored as $(v^C, c^C)$, and make similar measurements for the case when a drug has been applied, stored as $(v^D, c^D)$. Here C is for control (no drug) and D is for drug.

Steps 4 and 5: Inversion Generally, the notation $$(v, c) \xrightarrow{\text{inversion}(q)} p \quad (8)$$

means that the data (v, c) are inverted to yield a model parameterized by the vector p, using the model parameterized by the vector q as a starting point for the inversion. The control data (no drug) given by $(v^C, c^C)$ are inverted to yield the model parameterized by $p^{IM,C}$, using the parameter vector $p^{IM,B}$ as a starting point for the inversion. Likewise, the D-data are inverted to give the model $p^{IM,D}$, where the parameter vector $p^{IM,C}$ is used as starting point.

Step 6: Update maturation map The maturation map can now be updated to secure that if $Q$ is applied to the IM parameter vector, $p^{IM,C}$, the resulting parameter vector is the base model of the M cell parameterized by the vector $p^M$.

Step 7: Map from IM to M The updated maturation map $Q$ is used to compute the parameterization of the M version of the drugged cells.

Step 8: Drug affected M cell The effect of the drug on the M cells is analyzed by comparing the vectors $p^M$ and $p^{M,D}$. The components of $p^{M,D}$ that are significantly different from its $p^M$ counterpart, has been significantly affected by the drug. The effect of the drug on the mature AP is estimated by comparing the result of simulations of the models characterized by $p^M$ and $p^{M,D}$.

REFERENCES

[1] Hiroyuki Ando, Takashi Yoshinaga, Wataru Yamamoto, Keiichi Asakura, Takaaki Uda, Tomohiko Taniguchi, Atsuko Ojima, Raku Shinkyo, Kiyomi Kikuchi, Tomoharu Osada, Seiji Hayashi, Chieko Kasai, Norimasa Miyamoto, Hiroyuki Tashibu, Daiju Yamazaki, Atsushi Sugiyama, Yasunari Kanda, Kohei Sawada, and Yuko Sekino. A new paradigm for drug-induced torsadogenic risk assessment using human ips cell-derived cardiomyocytes. *Journal of Pharmacological and Toxicological Methods*, 84(Supplement C):111-127, 2017.

[2] Luca Sala, Milena Bellin, and Christine L Mummery. Integrating cardiomyocytes from human pluripotent stem cells in safety pharmacology: has the time come? *British journal of pharmacology*, 2016.

[3] Anurag Mathur, Peter Loskill, Kaifeng Shao, Nathaniel Huebsch, SoonGweon Hong, Sivan G Marcus, Natalie Marks, Mohammad Mandegar, Bruce R Conklin, Luke P Lee, and Kevin E. Healy. Human ipsc-based cardiac microphysiological system for drug screening applications. *Scientific reports*, 5:8883, 2015.

[4] John P Wikswo. The relevance and potential roles of microphysiological systems in biology and medicine. *Experimental biology and medicine*, 239(9):1061-1072, 2014.

[5] Eric W Esch, Anthony Bahinski, and Dongeun Huh. Organs-on-chips at the frontiers of drug discovery. *Nature reviews. Drug discovery*, 14(4):248, 2015.

[6] Yosuke K Kurokawa and Steven C George. Tissue engineering the cardiac microenvironment: Multicellular microphysiological systems for drug screening. *Advanced drug delivery reviews*, 96:225-233, 2016.

[7] Renjun Zhu, Adriana Blazeski, Ellen Poon, Kevin D. Costa, Leslie Tung, and Kenneth R. Boheler. Physical developmental cues for the maturation of human pluripotent stem cell-derived cardiomyocytes. *Stem Cell Research & Therapy*, 5(5):117, October 2014.

[8] Junyi Ma, Liang Guo, Steve J Fiene, Blake D Anson, James A Thomson, Timothy J Kamp, Kyle L Kolaja, Bradley J Swanson, and Craig T January. High purity human-induced pluripotent stem cell-derived cardiomyocytes: electrophysiological properties of action potentials and ionic currents. *American Journal of Physiology-Heart and Circulatory Physiology*, 301(5):H2006-H2017, 2011.

[9] Michelangelo Paci, Jari Hyttinen, Katriina Aalto-Setala and Stefano Severi. Computational models of ventricular- and atrial-like human induced pluripotent stem cell derived cardiomyocytes. *Annals of biomedical engineering*, 41(11): 2334-2348, 2013.

[10] Jie Liu, Zachary Laksman, and Peter H Backx. The electrophysiological development of cardiomyocytes. *Advanced drug delivery reviews*, 96:253-273, 2016.

[11] Fikru B Bedada, Matthew Wheelwright, and Joseph M Metzger. Maturation status of sarcomere structure and function in human ipsc-derived cardiac myocytes. *Biochimica et Biophysica Acta (BBA)-Molecular Cell Research*, 1863 (7): 1829-1838, 2016.

[12] Jingqi Q X Gong and Eric A Sobie. Population-based mechanistic modeling allows for quantitative predictions of drug responses across cell types. *NPJ systems biology and applications*, 4(1):11, 2018.

[13] Ping Liang, Feng Lan, Andrew S Lee, Tingyu Gong, Veronica Sanchez-Freire, Yongming Wang, Sebastian Diecke, Karim Sallam, Joshua W Knowles, Patricia K Nguyen, et al. Drug screening using a library of human induced pluripotent stem cell-derived cardiomyocytes reveals disease spe-cific patterns of cardiotoxicity. *Circulation*, pages CIRCULATIONAHA—113, 2013.

[14] Yoram Rudy and Jonathan R Silva. Computational biology in the study of cardiac ion channels and cell electrophysiology. *Quarterly Reviews of Biophysics*, 39(01):57-116, 2006.

[15] Yoram Rudy. From genes and molecules to organs and organisms: Heart. *Comprehensive Biophysics*, pages 268-327, 2012.

[16] Zhilin Qu, Gang Hu, Alan Garfinkel, and James N Weiss. Nonlinear and stochastic dynamics in the heart. *Physics Reports*, 543(2), 2014.

[17] Thomas O'Hara, La'szlo' Vira'g, Andra's Varro', and Yoram Rudy. Simulation of the undiseased human cardiac ventricular action potential: Model formulation and experimental validation. *PLoS Computational Biology*, 7(5):e1002061, 2011.

[18] Eleonora Grandi, Francesco S. Pasqualini, and Donald M. Bers. A novel computational model of the human ventricular action potential and Ca transient. *Journal of Molecular and Cellular Cardiology*, 48(1): 112-121, 2010.

[19] K H W J tenTusscher, D Noble, P J Noble, and Alexander V Panfilov. A model for human ventricular tissue. *American Journal of Physiology-Heart and Circulatory Physiology*, 286(4):H1573H1589, 2004.

[20] K H W J Ten Tusscher and A V Panfilov. Cell model for efficient simulation of wave propagation in human ventricular tissue under normal and pathological conditions. *Physics in medicine and biology*, 51(23):6141, 2006.

[21] Colleen E. Clancy, Zheng I. Zhu, and Yoram Rudy. Pharmacogenetics and anti-arrhythmic drug therapy: A theoretical investigation. *AJP: Heart and Circulatory Physiology*, 292(1):H66-H75, 2007.

[22] Jonathan D Moreno and Colleen E Clancy. Using computational modeling to predict arrhythmogenesis and antiarrhythmic therapy. *Drug Discovery Today: Disease Models*, 6(3):71-84, 2009.

[23] Aslak Tveito and Glenn T Lines. *Computing Characterizations of Drugs for Ion Channels and Receptors Using Markov Models*. Springer-Verlag, Lecture Notes, vol. 111, 279 pages, 2016.

[24] Michelangelo Paci, Elisa Passini, Stefano Severi, Jari Hyttinen, and Blanca Rodriguez. Phenotypic variability in 1qt3 human induced pluripotent stem cell-derived cardiomyocytes and their response to anti-arrhythmic pharmacological therapy: an in silico approach. *Heart Rhythm*, 2017.

[25] Dongrui Ma, Heming Wei, Yongxing Zhao, Jun Lu, Guang Li, Norliza Binte Esmail Sahib, Teng Hong Tan, Keng Yean Wong, Winston Shim, Philip Wong, et al. Modeling type 3 long qt syndrome with cardiomyocytes derived from patient-specific induced pluripotent stem cells. *International journal of cardiology*, 168(6): 5277-5286, 2013.

[26] Azra Fatima, Shao Kaifeng, Sven Dittmann, Guoxing Xu, Manoj K Gupta, Matthias Linke, Ulrich Zechner, Filomain Nguemo, Hendrik Milting, Martin Farr, et al. The disease-specific phenotype in cardiomyocytes derived from induced pluripotent stem cells of two long qt syndrome type 3 patients. *PloS one*, 8(12):e83005, 2013.

[27] Kirsi Kujala, Jere Paavola, Anna Lahti, Kim Larsson, Mari Pekkanen-Mattila, Matti Viitasalo, Annukka M Lahtinen, Lauri Toivonen, Kimmo Kontula, Heikki Swan, et al. Cell model of catecholaminergic polymorphic ventricular tachycardia reveals early and delayed afterdepolarizations. *PloS one*, 7(9):e44660, 2012.

[28] William J. Crumb, Jose Vicente, Lars Johannesen, and David G. Strauss. An evaluation of 30 clinical drugs against the comprehensive in vitro proarrhythmia assay (cipa) proposed ion channel panel. *Journal of Pharmacological and Toxicological Methods*, 81(Supplement C):251-262, 2016. Focused Issue on Safety Pharmacology.

[29] Anurag Mathur, Zhen Ma, Peter Loskill, Shaheen Jeeawoody, and Kevin E Healy. In vitro cardiac tissue models: Current status and future prospects. *Advanced drug delivery reviews*, 96:203-213, 2016.

[30] Denis Noble. A modification of the Hodgkin-Huxley equations applicable to Purkinje fibre action and pacemaker potentials. *The Journal of Physiology*, 160(2):317-352, 1962.

[31] Bert Sakmann and Erwin Neher, editors. *Single-Channel Recording*. Springer, 2nd edition, 1995.

[32] D. Colquhoun and A. G. Hawkes. On the stochastic properties of bursts of single ion channel openings and of clusters of bursts. *Philosophical Trans-actions of the Royal Society London B*, 300:1-59, 1982.

[33] Ivo Siekmann, James Sneyd, and Edmund J. Crampin. MCMC Can Detect Nonidentifiable Models. *Biophysical Journal*, 103(11):2275-2286, December 2012.

[34] Aslak Tveito, Glenn Lines, Andrew G Edwards, and Andrew D McCulloch. Computing rates of Markov models of voltage-gated ion channels by inverting partial differential equations governing the probability density functions of the conducting and non-conducting states. *Mathematical Biosciences*, doi. org/10.1016/j.mbs.2016.04.011, 2016.

[35] A L Hodgkin and A F Huxley. The components of membrane conductance in the giant axon of loligo. *The Journal of physiology*, 116(4):473-496, 1952.

[36] Meron Gurkiewicz and Alon Korngreen. A Numerical Approach to Ion Channel Modelling Using Whole-Cell Voltage-Clamp Recordings and a Genetic Algorithm. *PLoS Computational Biology*, 3(8):1633-1647, August 2007.

[37] Willemijn Groenendaal, Francis A Ortega, Armen R Kherlopian, Andrew C Zygmunt, Trine Krogh-Madsen, and David J Christini. Cell-specific cardiac electrophysiology models. *PLoS computational biology*, 11(4): e1004242, 2015.

[38] Astrid A Prinz, Dirk Bucher, and Eve Marder. Similar network activity from disparate circuit parameters. *Nature neuroscience*, 7(12):1345, 2004.

[39] Pablo Achard and Erik De Schutter. Complex parameter landscape for a complex neuron model. *PLoS computational biology*, 2(7):e94, 2006.

[40] Eve Marder and Adam L Taylor. Multiple models to capture the variability in biological neurons and networks. *Nature neuroscience*, 14(2):133, 2011.

[41] Amrita X Sarkar and Eric A Sobie. Regression analysis for constraining free parameters in electrophysiological models of cardiac cells. *PLoS computational biology*, 6(9):e1000914, 2010.

[42] K H W J ten Tusscher, Denis Noble, Peter-John Noble, and Alexander V Panfilov. A model for human ventricular tissue. *American Journal of Physiology-Heart and Circulatory Physiology*, 286(4):H1573H1589, 2004.

[43] Stefan A Mann, Mohammad Imtiaz, Annika Winbo, Annika Rydberg, Matthew D Perry, Jean-Philippe Couderc, Bronislava Polonsky, Scott McNitt, Wojciech Zareba, Adam P Hill, et al. Convergence of models of human ventricular myocyte electrophysiology after global optimization to recapitulate clinical long qt phenotypes. *Journal of molecular and cellular cardiology*, 100:25-34, 2016.

[44] Socrates Dokos and Nigel H Lovell. Parameter estimation in cardiac ionic models. *Progress in biophysics and molecular biology*, 85(2-3):407-431, 2004.

[45] Jaspreet Kaur, Anders Nygren, and Edward J Vigmond. Fitting membrane resistance along with action potential shape in cardiac myocytes improves convergence: application of a multi-objective parallel genetic algorithm. *PLoS One*, 9(9):e107984, 2014.

[46] Eric A Sobie. Parameter sensitivity analysis in electrophysiological models using multivariable regression. *Biophysical journal*, 96(4):1264-1274, 2009.

[47] Amrita X Sarkar and Eric A Sobie. Quantification of repolarization reserve to understand interpatient variability in the response to proarrhythmic drugs: a computational analysis. *Heart Rhythm*, 8(11):1749-1755, 2011.

[48] Amrita X Sarkar, David J Christini, and Eric A Sobie. Exploiting mathematical models to illuminate electrophysiological variability between individuals. *The Journal of physiology*, 590(11):2555-2567, 2012.

[49] Renjun Zhu, Michal A Millrod, Elias T Zambidis, and Leslie Tung. Variability of action potentials within and among cardiac cell clusters derived from human embryonic stem cells. *Scientific reports*, 6, 2016.

[50] Daniel Ortmann and Ludovic Vallier. Variability of human pluripotent stem cell lines. *Current opinion in genetics & development*, 46:179-185, 2017.

[51] Keiichi Asakura, Seiji Hayashi, Atsuko Ojima, Tomohiko Taniguchi, Norimasa Miyamoto, Chiaki Nakamori, Chiho Nagasawa, Tetsuo Kitamura, Tomoharu Osada, Yayoi Honda, et al. Improvement of acquisition and analysis methods in multi-electrode array experiments with ips cell-derived cardiomyocytes. *Journal of pharmacological and toxicological methods*, 75:17-26, 2015.

[52] Aslak Tveito, Karoline Horgmo Jxger, Miroslav Kuchta, Kent-Andre Mardal, and Marie E. Rognes. A cell-based framework for numerical modeling of electrical conduction in cardiac tissue. *Frontiers in Physics*, 5:48, 2017.

[53] Bertil Hille. *Ion channels of excitable membranes*, volume 507. Sinauer Sunderland, MA, 2001.

[54] H Sontheimer, B R Ransom, and S G Waxman. Different $Na^+$ currents in p0- and p7-derived hippocampal astrocytes in vitro: evidence for a switch in $Na^+$ channel expression in vivo. *Brain research*, 597(1):24-29, 1992.

[55] William J Moody and Martha M Bosma. Ion channel development, spontaneous activity, and activity-dependent development in nerve and muscle cells. *Physiological reviews*, 85(3):883-941, 2005.

Supplementary Information

Modification of the Action Potential Model

Figure 16:
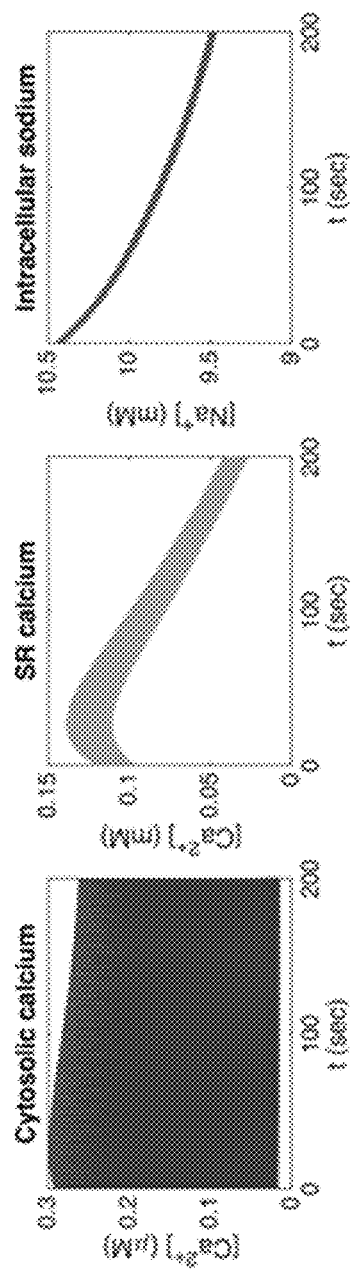
FIG. 16 shows an example of drift of ionic concentrations in the Paci et al. model ([1] in Example 2 Supplementary Information) with no stimulus current applied. First, the steady state solution of the original Paci et al. model was computed. Then, the IKr current was reduced by 50% and a simulation of this adjusted model was run for 200 seconds (corresponding to approximately 120 AP cycles). The plots show how the cytosolic calcium concentration (left panel), the SR calcium concentration (center panel), and the intracellular sodium concentration (right panel) changed with time during this long simulation.
Figure 17:
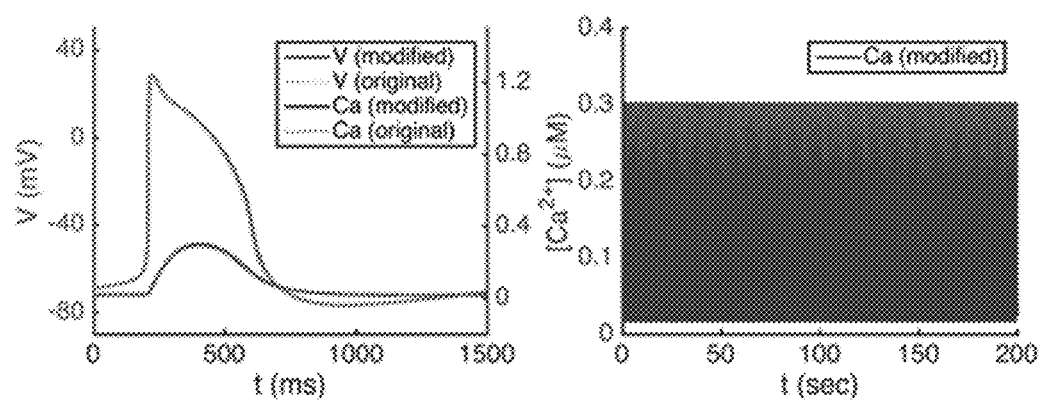
FIG. 17 shows the effect of freezing the intracellular sodium concentration and the SR calcium concentration in the Paci et al. model ([1] in Example 2 Supplementary Information). Left panel: comparison of the transmembrane potential and the cytosolic calcium concentration in the original Paci et al. model and the modified model with constant intracellular sodium and SR calcium concentrations. Right panel: long-term effect on the cytosolic calcium concentration of reducing the IKr current by 50%. The corresponding effect in the original Paci et al. model is given in the left panel of FIG. 16.
Figure 18:
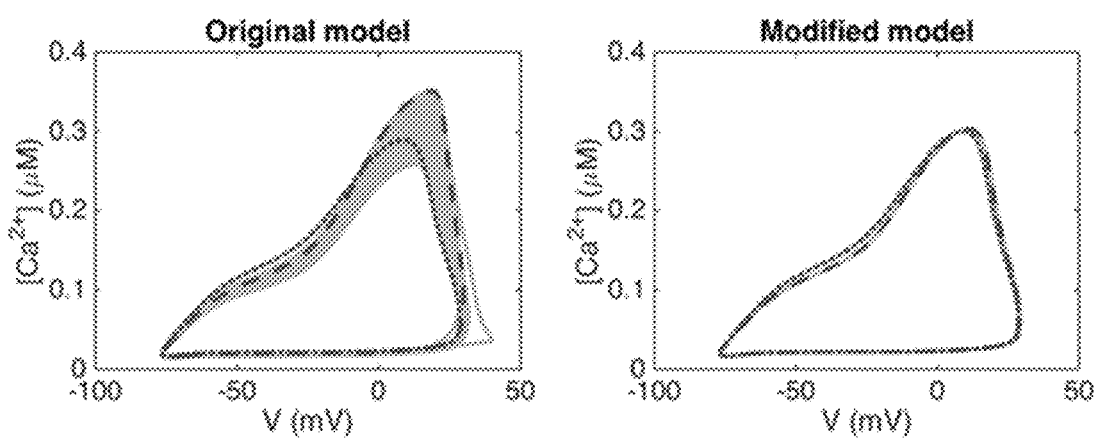
FIG. 18 shows convergence to steady state after scaling the IKr current down by 50%. A single cycle of the original Paci et al. model was first run, before running a simulation of the model with a reduced $I_{Kr}$ for 5,000 seconds (corresponding to approximately 3,000 AP cycles). The cytosolic calcium concentration is plotted against the transmembrane potential of each cycle. The dotted line shows the cycle with the parameter values of the original Paci et al. model and the dashed line shows the new steady state solution obtained for a reduced $I_{Kr}$. Left panel: for the original Paci et al. model ([1] in Example 2 Supplementary Information), a new steady state solution was not reached until after approximately 1,000 AP cycles. Right panel: in the modified model with constant intracellular sodium and SR calcium concentrations, the solution did not change much after the first cycle with a reduced $I_{Kr}$ current.

In the process of adjusting the Paci et al. [1] model to the data obtained from an MPS (microphysiological system, [2]), we had to run the model many thousand times with varying choices of parameters. One difficulty encountered in this process was drift of ion concentrations. This is a well-known problem of mathematical models of electrophysiology; see, e.g., [3, 4, 5]. In FIG. 16, we illustrate this problem for the original Paci et al. model. One approach to solve this problem is to decompose stimulus currents into ion concentrations and thereby retain conservation of the ion concentrations, see, e.g., [3]. A problem with this approach is that drift is observed also when no stimulus is applied (see, FIG. 16). Another approach relies on the fact that some ion concentrations vary little and can therefore be kept constant. Here, we followed this latter approach and froze the intracellular sodium concentration and the SR calcium concentration at their initial values. In FIG. 17, we show the properties of this approximation. In the right panel, we note that the cytosolic calcium concentration no longer drifted even for very long simulations. In the left panel, we show that the effect of this approximation on the transmembrane potential and the cytosolic calcium concentration was very small. With this approximation, convergence towards the steady state solution (a steady periodic solution) was rapid and the solutions appeared to be stable. This is demonstrated in FIG. 18 where convergence to steady state is illustrated. First, we computed the steady state solution of the modified model using the original parameters of the Paci et al. model. Then, we reduced $I_{Kr}$ by 50% and noted that the solution rapidly reached equilibrium.

The Maturation Map of the Calcium Dynamics

We consider how the Ca-dynamics change under maturation. As for the membrane ion channel case, we do this by illustrating the maturation process for a very simple model.

Figure 19:
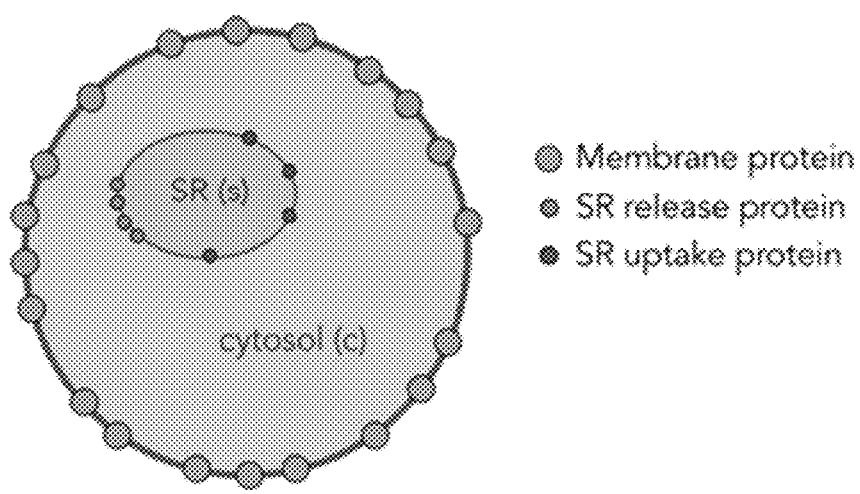
FIG. 19 shows an illustration of the intracellular volume consisting of the cytosolic space (c) and the SR (s). The SR is equipped with specialized proteins for uptake and release of calcium.

We consider an intracellular volume consisting of the cytosol (c) surrounding the sarcoplasmic reticulum (SR (s)); see, FIG. 19.

We let $N_c$ denote the number of $Ca^{2+}$ ions in the cytosol and $N_s$ denote the number of $Ca^{2+}$ ions in the sarcoplasmic reticulum; both given in mmol. The associated volumes are given by $V_c$ and $V_s$, both given in L. Let $J_{c,s}$ and $J_{s,c}$ denote the flux (in mmol/ms) of $C^{2+}$ ions from the cytosol to the SR, and from the SR to the cytosol, respectively. Conservation of $Ca^{2+}$ ions yields the model $$(dN_c/dt) = J_{s,c} - J_{c,s} \tag{1}$$

$$(dN_s/dt) = J_{c,s} - J_{s,c} \tag{2}$$

The fluxes are models of proteins carrying ions from one volume to the other. Let $g^0_{c,s}$ (in mmol/ms) be the flux representing one single protein transporting $Ca^{2+}$ ions from the cytosol to the SR. Similarly, $g^0_{s,c}$ (in mmol/ms) is the flux representing one single protein releasing $Ca^{2+}$ ions from the SR to the cytosol. The number of such proteins are given by $N_{c,s}$ and $N_{s,c}$. Then, the system (1) and (2) takes the form $$(dN_c/dt) = N_{s,c} g^0_{s,c} - N_{c,s} g^0_{c,s} \quad (3),$$

$$(dN_s/dt) = N_{c,s} g^0_{c,s} - N_{s,c} g^0_{s,c} \quad (4).$$

By defining the fluxes (in mM/ms)

$$j_{c,s} = \frac{N_{c,s} g^0_{c,s}}{V_c}, \quad j_{s,c} = \frac{N_{s,c} g^0_{s,c}}{V_c} \quad (5)$$

the system takes the form $$\frac{dC_c}{dt} = J_{S,C} - J_{C,S}, \quad (6)$$

$$\frac{dC_S}{dt} = \frac{V_c}{V_s}(j_{c,s} - j_{s,c}), \quad (7)$$

where $C_c$ and $C_s$ are the concentrations (in mM) of $Ca^{2+}$ ions in the cytosol and SR, respectively;

$$C_c = \frac{N_c}{V_c}, \quad C_s = \frac{N_s}{V_s}. \quad (8)$$

For maturation, we can now follow the same steps as for the membrane proteins. During maturation, the properties of the single proteins will remain constant, but the number of proteins and the volumes will increase. Therefore, we introduce constants $qV_c$, $qV_s$, $qN_{c,s}$ and $qN_{s,c}$ such that $$V_c^M = qv_c V_c^{IM}, V_s^M = qv_s V_s^{IM} \quad (9),$$

$$N_{c,s}^M = qN_{c,s} N_{c,s}^{IM}, N_{c,s}^M = qN_{s,c} N_{s,c}^{IM} \quad (10).$$

With $$j_{c,s}^{IM} = \frac{N_{c,s}^{IM} g^0_{c,s}}{V_c^{IM}}, \quad j_{s,c}^{IM} = \frac{N_{s,c}^{IM} g^0_{s,c}}{V_c^{IM}} \quad (11)$$

we get $$j_{c,s}^M = \frac{N_{c,s}^M g^0_{c,s}}{V_c^M} = \frac{qN_{c,s} N_{c,s}^{IM} g^0_{c,s}}{qv_c V_c^{IM}} = \frac{qN_{c,s}}{qV_c} j_{c,s}^{IM}, \quad (12)$$

$$j_{s,c}^M = \frac{N_{s,c}^M g^0_{s,c}}{V_c^M} = \frac{qN_{c,s} N_{s,c}^{IM} g^0_{s,c}}{qv_c V_c^{IM}} = \frac{qN_{s,c}}{qV_c} j_{s,c}^{IM}. \quad (13)$$

Consequently, we have the IM model $$\frac{dC_C}{dt} = j_{S,C}^{IM} - j_{C,S}^{IM}, \quad (14)$$

$$\frac{dC_S}{dt} = \frac{V_C^{IM}}{V_S^{IM}}(j_{C,S}^{IM} - j_{S,C}^{IM}), \quad (15)$$

and the associated M model $$\frac{dC_C}{dt} = \frac{qN_{S,C}}{qV_C} j_{S,C}^{IM} - \frac{qN_{C,S}}{qV_C} j_{C,S}^{IM}, \quad (16)$$

$$\frac{dC_S}{dt} = \frac{qV_C V_C^{IM}}{qV_S V_S^{IM}} \left( \frac{qN_{C,S}}{qV_C} j_{C,S}^{IM} - \frac{qN_{S,C}}{qV_C} j_{S,C}^{IM} \right). \quad (17)$$

Again, we observe that the M model is obtained simply by multiplication by a set of maturation factors.

Technical Specifications of the Model Formulation and Inversion Procedure

In this section, technical specifications regarding the model formulation used in the simulations and the inversion procedure are provided.

Intracellular Concentrations

In almost all of our computations, we used the modified version of the Paci et al. model described above with fixed intracellular sodium and SR calcium concentrations. The only exception is that we also ran some simulations of ten Tusscher et al. model [6] in FIG. 11. In these simulations, the intracellular potassium, sodium, and SR calcium concentrations were also fixed at constant values. The intracellular concentrations used in the IM and M formulations of the modified Paci et al. model and the similarly modified ten Tusscher et al. model are given in Table 3.

Numerical Stimulation Protocol

In all simulations, the cells were stimulated every 1,000 ms by a 5 ms long stimulus current of 8 µA/µF. The simulations were run for five AP cycles before recording the action potential and calcium transient for each new parameter combination.

TABLE 3

Intracellular concentrations used in the IM and M versions of the modified Paci et al. [1] and ten Tusscher et al. [6] models with fixed intracellular sodium, intracellular potassium, and SR calcium concentrations.

|  | $[Na^+]_i$ (mM) | $[K^+]_i$ (mM) | $[Ca^{2+}]_{SR}$ (mM) |
| --- | --- | --- | --- |
| Paci IM | 10.45 | 150.00 | 0.12 |
| Paci M | 10.45 | 150.00 | 0.55 |
| ten Tusscher IM | 11.37 | 138.20 | 0.12 |
| ten Tusscher M | 11.37 | 138.20 | 0.53 |

Technical Specifications for the Drug Inversions

When the inversion procedure is used to fit simulated or measured drug and control data, we only considered adjustments of the $q_{Na}$, $q_{caL}$, $q_{Kr}$, and $q_{K1}$ factors, unless otherwise specified. Note, however, that for the inversion of the verapamil data in FIGS. 9 and 10, the $I_{Na}$ current was reduced by 50%, the $I_{NaK}$ current was reduced by 60%, the $I_{caL}$ current was increased by 60%, and the $I_{up}$ and $I_{rel}$ fluxes were increased by 30% before running the inversion of the $q_{Na}$, $q_{caL}$, $q_{Kr}$, and $q_{K1}$ factors, in order to make the base model used in the inversion more similar to the control data.

Technical Specifications for the Construction of the Maturation Map

In the construction of the maturation maps demonstrated in FIG. 11 we use the inversion procedure to fit an immature model (Paci et al. [1]) to a mature model (ten Tusscher et al. [6]) and to fit the mature model to the immature model. In these inversions, we consider adjustments of the $q_{Na}$, $q_{caL}$, $q_{to}$, $q_{Ks}$, $q_{Kr}$, $q_{K1}$, $q_{NaCa}$, $q_{NaK}$, $q_{pCa}$, $q_f$, $q_{bNa}$, $q_{bCa}$, $q_{leak}$, $q_{up}$, and $q_{rel}$ factors (in addition to the $q_{pK}$ factor for the ten Tusscher et al. model). Note that the $I_r$ current is added to the ten Tusscher et al. model in these simulations using the same formulation as in the default Paci et al. model, but with a conductance reduced by a factor of 10 for the mature ten Tusscher model, i.e., $g_r$=0.003 mS/µF.

Because of the large number of free parameters, we conducted a more detailed inversion procedure in this case with twelve iterations and 15,000 randomly chosen adjustment factors in each iteration. In addition, we included some additional terms in the cost function containing information that is not available from the optical measurements, but may be obtained from the mathematical models. More specifically, we used a cost function of the form $$H(\lambda) = \left(\sum_{j=1}^{20} H_j(\lambda)\right)^{1/2}, \quad (18)$$

where $H_1$-$H_8$ are the same as in the remaining applications of the inversion procedure, that is $$H_1 = \frac{\left|\int_{t_0(\lambda)}^{t_1(\lambda)} v(\lambda)dt - \int_{t_0^*}^{t_1^*} v^* dt\right|}{\left|\int_{t_0^*}^{t_1^*} v^* dt\right|}, \quad H_2 = \frac{|APD_{V,30}(\lambda) - APD_{V,30}^*|}{|APD_{V,30}^*|},$$

$$H_3 = \frac{|APD_{V,50}(\lambda) - APD_{V,50}^*|}{|APD_{V,50}^*|}, \quad H_4 = \frac{|APD_{V,80}(\lambda) - APD_{V,80}^*|}{|APD_{V,80}^*|},$$

$$H_5 = \frac{\left|\left(\frac{dc}{dt}\right)_{max}(\lambda) - \left(\frac{dc}{dt}\right)_{max}^*\right|}{\left|\left(\frac{dc}{dt}\right)_{max}^*\right|}, \quad H_6 = \frac{|APD_{Ca,30}(\lambda) - APD_{Ca,30}^*|}{|APD_{Ca,30}^*|},$$

$$H_7 = \frac{|APD_{Ca,50}(\lambda) - APD_{Ca,50}^*|}{|APD_{Ca,50}^*|}, \quad H_8 = \frac{|APD_{Ca,80}(\lambda) - APD_{Ca,80}^*|}{|APD_{Ca,80}^*|},$$

where the star * is used to denote the simulated data to which we are trying to adjust the model. Furthermore, $APD_{V,30}$ is defined as the length (in ms) of the time from the value of the membrane potential, in the upstroke, is 30% below its maximum value ($t_0$) until it again is repolarized to 30% of its maximum value ($t_1$). In $H_1$, we compute the integral of the membrane potential with respect to time t from $t=t_0$ to $t=t_1$. The values $APD_{V,50}$ and $APD_{V,80}$ are defined similarly to $APD_{V,30}$, and the terms $APD_{Ca,30}$, $APD_{Ca,50}$ and $APD_{Ca,80}$ represent the corresponding transient durations for the calcium concentration. Moreover, in $H_5$, $(dc/dt)_{max}$ is the maximal upstroke velocity of the calcium concentration.

The additional terms for the construction of the maturation map are given by $$H_9 = \frac{|v(\lambda)_{max} - v_{max}^*|}{|v_{max}^*|}, \quad H_{10} = \frac{|v(\lambda)_{rest} - v_{rest}^*|}{|v_{rest}^*|},$$

$$H_{11} = \frac{|c(\lambda)_{max} - c_{max}^*|}{|c_{max}^*|}, \quad H_{12} = \frac{|c(\lambda)_{rest} - c_{rest}^*|}{|c_{rest}^*|},$$

$$H_{13} = \frac{\|I_{Na}(\lambda) - I_{Na}^*\|_2}{\|I_{Na}^*\|_2}, \quad H_{14} = \frac{\|I_{Na}(\lambda) - I_{Na}^*\|_\infty}{\|I_{Na}^*\|_\infty},$$

-continued $$H_{15} = \frac{\|I_{CaL}(\lambda) - I_{CaL}^*\|_2}{\|I_{CaL}^*\|_2}, \quad H_{16} = \frac{\|I_{CaL}(\lambda) - I_{CaL}^*\|_\infty}{\|I_{CaL}^*\|_\infty},$$

$$H_{17} = \frac{\|I_{Kr}(\lambda) - I_{Kr}^*\|_2}{\|I_{Kr}^*\|_2}, \quad H_{18} = \frac{\|I_{Kr}(\lambda) - I_{Kr}^*\|_\infty}{\|I_{Kr}^*\|_\infty}, \ldots$$

Here, $v_{max}$ and $c_{max}$ denote the maximum value of the membrane potential and the calcium concentration, respectively. Similarly, $v_{rest}$ and $c_{rest}$ denote the resting membrane potential and calcium concentration, respectively, defined as the values obtained 10 ms before stimulation. Moreover, $\|I\|_2$ and $\|I\|_\infty$ are defined as $$\|I\|_2 = \sqrt{\sum_n I(t_n)^2},$$

$$\|I\|_\infty = \max_n |I(t_n)|,$$

where n runs over all the time steps of an action potential. The currents $I_{Na}$, $I_{CaL}$, $I_{Kr}$, and $I_{K1}$ are chosen to be included in the cost function because we are especially interested in obtaining realistic behaviors for these currents since these are the currents considered in the drug inversions.

Identification of Simulated Single-Channel Block Using $H_V$ and $H_{Ca}$

Figure 20:
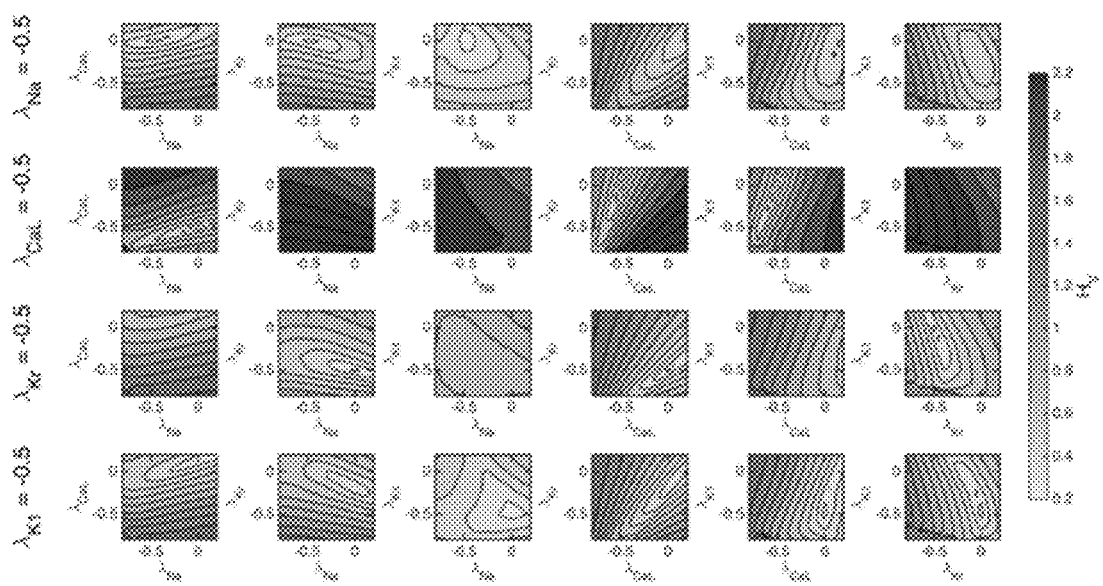
FIG. 20 shows the cost function Hv with ε=0.2 evaluated for pairwise perturbations of the maximum conductances of four major currents for simulated single-channel block of each of the currents. In the upper panel, $I_{Na}$ is blocked by 50%, and in the next panels, $I_{caL}$, $I_{Kr}$, and $I_{K1}$ are similarly blocked by 50%.
Figure 21:
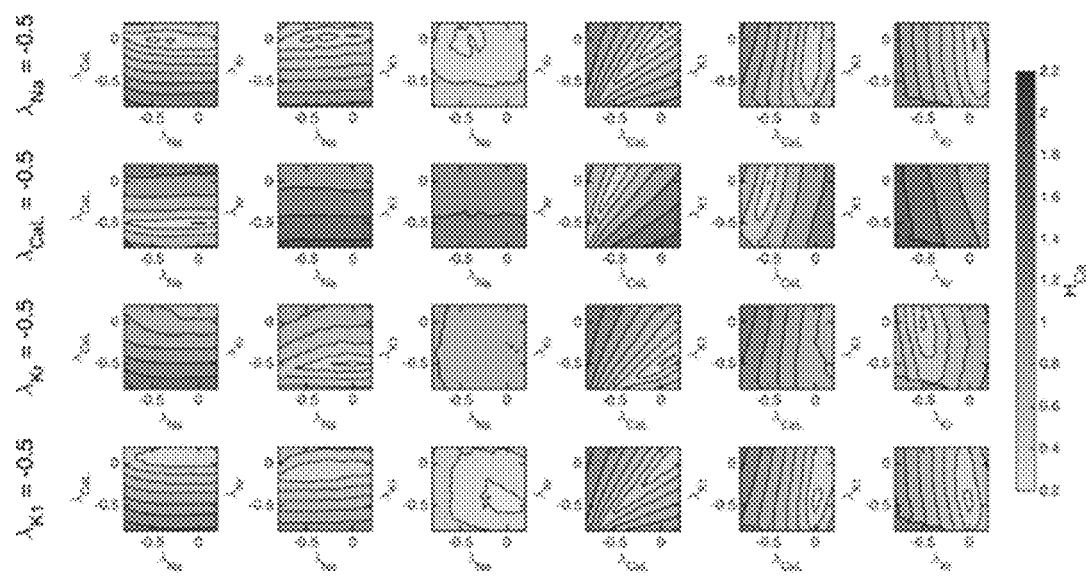
FIG. 21 shows the cost function $H_{Ca}$ with ε=0.2 evaluated for pairwise perturbations of the maximum conductances of four major currents for simulated single-channel block of each of the currents. In the upper panel, $I_{Na}$ is blocked by 50%, and in the next panels, $I_{caL}$, $I_{Kr}$, and $I_{K1}$ are similarly blocked by 50%.

In FIG. 10 we showed the value of $H_{V+Ca}$ for pairwise perturbations of the maximum conductance of four major currents for simulated single-channel block of each of the currents. FIGS. 20 and 21 show corresponding plots for the cost functions $H_V$ and $H_{Ca}$, respectively. In these figures, we observe that the terms of $H_V$ seem to contain the main part of $H_{V+Ca}$ observed in FIG. 10.

REFERENCES FOR SUPPLEMENTARY INFORMATION

[1] Michelangelo Paci, Jari Hyttinen, Katriina Aalto-Seta'la', and Stefano Severi. Computational models of ventricular- and atrial-like human induced pluripotent stem cell derived cardiomyocytes. *Annals of biomedical engineering*, 41(11):2334-2348, 2013.

[2] Anurag Mathur, Peter Loskill, Kaifeng Shao, Nathaniel Huebsch, SoonGweon Hong, Sivan G. Marcus, Natalie Marks, Mohammad Mandegar, Bruce R. Conklin, Luke P. Lee, and Kevin E. Healy. Human ipsc-based cardiac microphysiological system for drug screening applications. *Scientific reports*, 5:8883, 2015.

[3] Thomas J. Hund, Jan P. Kucera, Niels F. Otani, and Yoram Rudy. Ionic charge conservation and long-term steady state in the Luo-Rudy dynamic cell model. *Biophys J*, 81(6):3324-3331, December 2001.

[4] Ronald Wilders. Computer modelling of the sinoatrial node. *Medical and Biological Engineering and Computing*, 45(2):189-207, February 2007.

[5] Victor A. Maltsev, Yael Yaniv, Anna V. Maltsev, Michael D. Stern, and Edward G. Lakatta. Modern perspectives on numerical modeling of cardiac pacemaker cell. *Journal of Pharmacological Sciences*, 125(1): 6-38, 2014.

[6] Kirsten H. W. J. ten Tusscher, Denis Noble, Penelope J. Noble, and Alexander V. Panfilov. A model for human ventricular tissue. *American Journal of Physiology-Heart and Circulatory Physiology*, 286(4):H1573H1589, 2004.

Example 3

Singular Value Decomposition

Excitable cells are present in the brain, in the heart, in every muscle, and in all critical organs of the body. The dynamics of such cells are surprisingly complex, and are commonly studied using detailed mathematical models based on experimental measurements of underlying biophysical processes. However, such models are becoming increasingly complex as more experimental data become available, and it becomes a challenge to understand their well-posedness. In this example, we investigate this problem in models describing cardiac cell dynamics. In particular, we ask: Can different model parameters give identical output? Answers to this question turn out to be highly important when we want to evaluate the effect of drugs in the cardiac system, or if we want to characterize the effect of genetic mutations on system dynamics. Here, we use the Singular Value Decomposition (SVD) to investigate if it is possible to change model parameters, in our case the maximum conductances of the major ion currents that drive the function of the cell, without seeing any discernible effects on the action potential. We find that commonly used models of the action potential of human cardiac cells have this property; such that significant changes in the parameters can be introduced without any resulting change in commonly measured system outputs.

Abstract

Mathematical models describing the dynamics of the cardiac action potential are of great value for understanding how changes to the system can disrupt the normal electrical activity of cells and tissue in the heart. However, in order to represent specific data, these models must be parameterized, and adjustment of the maximum conductances of the individual contributing ionic cellular currents is a commonly used method. Here we present a method for investigating the uniqueness of such resulting parameterizations. Our key question is this: Can the maximum conductances of a model be changed without giving any appreciable changes in the action potential? If so, the model parameters are not unique and this poses a major problem in using the models to identify changes in the parameters from data, for instance, to evaluate a potential drug effect. We propose a method for evaluating this uniqueness, founded on the singular value decomposition of a matrix consisting of the contribution from all the individual ion currents over the time course of an action potential. Small singular values of this matrix signify lack of parameter uniqueness and we show that the conclusion from linear analysis of the matrix of currents carries over to provide insight in the uniqueness of the parameters in the non-linear case.

Introduction

In a conversation with Enrico Fermi, John von Neumann famously said, with four parameters I can fit an elephant, and with five I can make him wiggle his trunk [1]. Clearly, both Fermi and von Neumann were cautious in introducing new parameters in mathematical models of physics, because they feared that with large degrees of freedom, the equations could basically be tweaked to fit any observation. Although mathematical models in biology historically have roots in physics, the frugality of classical models in physics has not translated well over to biology. This is particularly the case in recent mathematical models describing the dynamics of electrically active cardiac cells, where it is difficult even to count the number of adjustable parameters, let alone estimate all their values.

Since the seminal papers of Hodgkin and Huxley [2], and Noble [3], mathematical models have been used extensively and successfully to understand the action potential (AP) of excitable cells. Recent years have witnessed a very strong growth in the number of models describing a wide variety of cells and behaviors; see, e.g., [4] for a comprehensive collection of models. Introduction to mathematical models of the AP is provided in e.g., [5, 6, 7, 8] and review of recent developments of AP models for cardiac cells is presented in e.g., [9, 10, 11, 12, 13]. Early models of cardiac cells were rather compact, in the sense that they were formulated in terms of relatively few ordinary differential equations, but recent models tend to be quite large. For small models, it is possible to understand the dynamics described by the model equations, but for large and complex models, it is increasingly hard to understand the dynamics represented by all the terms entering the model, and useful information concerning the output of the model must be based on numerical computations.

It has consequently become increasingly difficult to analyze the mapping between the model parameters and the solution, leading to significant challenges in parameterizing the models to reflect a given data set. Such parametrization is commonly approached using a variety of techniques, from detailed analysis of individual contributing currents, to inheritance from previous work done in completely non relevant experiments [14]. Here, we examine this problem assuming that the action potential of a paced cell can be accurately measured and that the problem of parametrization is to adjust a given model to the acquired waveform. This is particularly relevant for techniques where the transmembrane potential is measured optically using voltage sensitive fluorescence; see, e.g., [15, 16]. Such voltage sensitive reporting is now routinely used to analyze many cells including human induced pluripotent stem cells (hiPSCs); see, e.g., [17]. We have recently developed methods for inverting data representing the transmembrane potential and intracellular calcium concentration of hiPSC-derived cardiomyocytes; see, [18]. In that project, it turned out to be essential to be able to automatically invert measured data to obtain the maximum conductances of an AP model. Furthermore, it became clear that some currents could be identified using calcium and voltage data, whereas other membrane currents were practically invisible using this data.

The purpose of the present work described here was to present a method for investigating the identifiability of conductances based on observations of the transmembrane potential. The method is based on the Singular Value Decomposition (SVD; see, e.g., [19, 20]) of a matrix representing the individual transmembrane ion currents, $I_i$. These ion currents contribute to the total transmembrane current $$I_T = \sum_{i=1}^{N} I_i \quad (1)$$

given in A/F. This total transmembrane current governs the dynamics of the cellular transmembrane potential $v = v(t)$ (v is in mV, time t is in ms) by $$\frac{dv(t)}{dt} = -I_T \quad (2).$$

We were interested in estimating the effect of replacing an ion current $I_i$ by a perturbed current given by $(1+\lambda_i)I_i$. If the effect of such a perturbation is small, it will be very difficult to parameterize the current by simply observing changes in the total membrane current $I_T$ given by (1). In order to investigate how changes in the membrane currents, $I_i$, affect the total current, $I_T$, we performed an AP simulation using the model (2). At given time steps in the simulation (e.g., every ms) we stored the values of every ion current in a matrix A; each row in the matrix represents tede individual ion currents at a given time step. Then, we computed the singular values and singular vectors of that matrix. If a singular value of the was zero, it meant that if we changed the vector of conductances along the corresponding non-zero singular vector, the total current would not change and therefore no changes could be observed in the transmembrane potential.

However, linear analysis of the matrix containing the ion currents cannot directly be used to predict the effect of perturbations on the transmembrane potential. In fact, the original model reads $$\frac{dv(t)}{dt} = -\sum_{i=1}^{N} I_i(v, s), \qquad (3)$$

and the perturbed model reads $$\frac{dv^\lambda(t)}{dt} = -\sum_{i=1}^{N} (1 + \lambda_i) I_i(v^\lambda, s^\lambda). \qquad (4)$$

Here, s is a vector containing other state variables of the model. Therefore, the $(1+\lambda_i)$ perturbation introduces a non-linear perturbation and we describe below how the linear results translate into non-linear effects.

The common way of investigating the sensitivity of non-linear AP models of the form (1) is to compare the solutions of the model with and without perturbed conductances. When every individual conductance is analyzed, a rough indication of the parameter sensitivity is obtained; see, e.g., [21, 22, 23, 18]. This method is well established and clearly provides valuable insight. However, the method can only detect sensitivities for single currents and not combinations of currents. Suppose, for instance, that two currents are very sensitive when they are perturbed individually, but if both are increased, the changes cancel each other out and no discernible changes can be observed in the total membrane current. Such subtle cancellation effects turn out to be surprisingly common and almost (or perhaps entirely) impossible to see if only individual currents are perturbed. It is also very hard to search for such insensitivities by randomly combining various currents because the search space is so large and each simulation is time consuming. Therefore, the SVD method turns out to be useful and we will demonstrate how it works for well-known models of human ventricular APs.

Methods

Our aim was to develop a method for investigating the uniqueness of the maximum conductances in AP models. The question we wanted to address was this: For a given AP model, can the maximum conductances be changed significantly without appreciable changes in the resulting transmembrane potential?

We assume that the transmembrane potential is governed by a model of the form $$\frac{dv(t)}{dt} = -\sum_{i=1}^{N} I_i(v, s), \qquad (5)$$

$$\frac{ds(t)}{dt} = F(v, s). \qquad (6)$$

Here, as above, v denotes the transmembrane potential, s denotes the other variables of the AP model (concentrations and gating variables), $\{I_i\}_{i=1}^{N}$ denotes the collection of ion currents and F represents the dynamics of the gating variables and the ion concentrations. Here, we assume that each ion current can, for example, be written on the form $$I_i = g_i o_i (v - v_i^0) \qquad (7),$$

where $g_i$ denotes the maximum conductance, $o_i$ is the open probability, and $v_i^0$ denotes the resting potential of the i-th ion channel.

In addition to the model (5), we also consider the following perturbed model, $$\frac{dv^\lambda(t)}{dt} = -\sum_{i=1}^{N} (1 + \lambda_i) I_i(v^\lambda, s^\lambda), \qquad (8)$$

$$\frac{ds^\lambda(t)}{dt} = F(v^\lambda, s^\lambda; \lambda), \qquad (9)$$

which is similar to the original model except that every ion current is perturbed by a term of the form $(1+\lambda_i)$. Clearly $v = v^\lambda$ for $\lambda = 0$, but can we find a vector where $\lambda$ does not equal 0 such that $v \approx v^\lambda$? If such a vector $\lambda$ exists, then clearly knowing the values of the transmembrane potential for all points in time is not enough to infer the maximum conductances, because different maximum conductances can give the same transmembrane potential.

Recording Currents During an AP Simulation

During a simulation based on the model (5),(6), we store the total membrane current and the individual ion currents at certain time steps. More precisely, we store the total membrane current $I_T^k$ and the individual currents $I_j^k$ for $j = 1, \ldots, N$ at time $t_k = k\Delta t$ for $k = 1, \ldots, M$. Here, N denotes the number of ion currents, and M denotes the number of time steps at which the currents are stored. We were interested in the effect of perturbing individual currents and for that purpose we introduce the vector $\mu \in \mathbb{R}^{N,1}$. With $\mu = (1, 1, \ldots, 1)^T$, we can write the total membrane current as a matrix-vector product, $$I_T = A\mu \qquad (10),$$

where we have gathered all individual ion currents in the matrix A defined by $$A = \begin{pmatrix} I_1^1 & \cdots & I_N^1 \\ \vdots & & \vdots \\ I_1^M & \cdots & I_N^M \end{pmatrix}, \qquad (11)$$

and the total current is given by $$I_T = \begin{pmatrix} I_T^1 \\ I_T^2 \\ \vdots \\ I_T^M \end{pmatrix}.$$

Note that $I_T \in \mathbb{R}^{M,1}, A \in \mathbb{R}^{M,N},$ and $\mu \in \mathbb{R}^{N,1}.$ The Singular Value Decomposition (SVD) of the Current Matrix The SVD exists for any matrix A and takes the form $$A = USV^T \quad (12),$$

see, e.g., [19, 20]. Here, $U \in \mathbb{R}^{M,M}$, $V \in \mathbb{R}^{N,N}$, and $S \in \mathbb{R}^{M,N}$. Note that U and V are unitary matrices, i.e. $UU^T = I$, $U^T U = I$, $VV^T = I$, and $V^T V = I$, where I is the identity matrix. The matrix S is a diagonal matrix with positive singular values $\sigma_i$ satisfying $\sigma_1 \geq \sigma_2 \geq \ldots \geq \sigma_r > 0$, where r is the rank of the matrix A. The singular values and singular vectors satisfy the following relations, $$Av_i = \sigma_i u_i, i = 1, \ldots, r \quad (13),$$

$$Av_i = 0, i = r+1, \ldots, N \quad (14),$$

$$A^T u_i = \sigma_i v_i, i = 1, \ldots, r \quad (15),$$

$$A^T u_i = 0, i = r+1, \ldots, M. \quad (16)$$

Furthermore, the singular vectors define orthonormal bases as follows, $\{u_1, \ldots, u_r\}$ is an orthonormal basis for $N(A^T)^\perp$ (17), $\{u_{r+1}, \ldots, u_M\}$ is an orthonormal basis for $N(A^T)$ (18), $\{v_1, \ldots, v_r\}$ is an orthonormal basis for $N(A)^\perp$ (19), $\{v_{r+1}, \ldots, v_N\}$ is an orthonormal basis for $N(A)$ (20).

Here, $N(A)$ and $N(A^T)$ are the null spaces of A and $A^T$, respectively, and $N(A^T)^\perp$ and $N(A)^\perp$ are the column and row spaces of A, respectively.

The Effect of Perturbing the Parameter Vector $\mu$; the Maximum Conductances

We will use the SVD to analyze the effect of perturbing the parameter vector $\mu$. For that purpose, recall that $$I_T = A\mu,$$

and consider also the total membrane current for a perturbed vector, $\bar{\mu}$, $$\bar{I}_T = A\bar{\mu}.$$

Perturbation Along a Singular Vector

Let us first consider the special case of $$\bar{\mu} = \mu + \varepsilon v_i,$$

where $v_i$ is a singular vector of A (see, (13)), and $\varepsilon$ is a parameter indicating the strength of the perturbation (the Euclidian norm of $v_i$ is one).

Note that $$I_T - \bar{I}_T = A\mu - A\bar{\mu} = -\varepsilon Av_i = -\varepsilon \sigma_i u_i,$$

and therefore, in the Euclidian norm $\|\cdot\|$ and the associated inner product $(\cdot, \cdot)$, we have $$\|I_T - \bar{I}_T\|^2 = (I_T - \bar{I}_T, I_T - \bar{I}_T) = \varepsilon^2 \sigma_i^2 (u_i, u_i) = \varepsilon^2 \sigma_i^2,$$

so $$\|I_T - \bar{I}_T\| = \varepsilon \sigma_i \quad (21).$$

This means that the effect of a perturbation along a singular vector is proportional to the associated singular value. Therefore, perturbations of the maximum conductances along singular vectors associated with large singular values will be readily observed by significant changes in the total membrane current. Conversely, a perturbation of the maximum conductances along a singular vector for which the associated singular value is zero, or very small, will not result in appreciable changes in the total membrane current and is therefore expected to be impossible to identify by only observing the transmembrane potential.

A General Perturbation

Since the collection of singular vectors constitutes an orthonormal collection of vectors, any perturbed vector $\bar{\mu}$ can be written on the form $$\bar{\mu} = \mu + \Sigma_{i=1}^N \varepsilon_i v_i,$$

for appropriate choices of the constants $\{\varepsilon_i\}$. By using this representation, we find that $$I_T - \bar{I}_T = A\mu - A\bar{\mu} = -\Sigma_{i=1}^N \varepsilon_i \sigma_i u_i,$$

so $$\|I_T - \bar{I}_T\|^2 = \Sigma_{i=1}^N \varepsilon_i^2 \sigma_i^2 = \Sigma_{i=1}^r \varepsilon_i^2 \sigma_i^2.$$

In other words, if $\bar{\mu} - \mu$ can be expressed using only the singular vectors $\{v_i\}_{i=r+1}^N$, then $\|I_T - \bar{I}_T\|^2 = 0$, and therefore, such a perturbation will not lead to changes in the total membrane current. On the other hand, if $\bar{\mu} - \mu$ can be expressed using the singular vectors $\{v_i\}_{i=1}^r$, then $\|I_T - \bar{I}_T\|^2$ is not equal to 0, and such a perturbation will lead to changes in the total membrane current.

The Identifiability Index

We have seen that, according to the SVD analysis, perturbations along vectors that can be spanned by vectors in the space $N(A) = \text{span}\{v_{r+1}, \ldots, v_N\}$ cannot be identified by observing changes in the total membrane current and, conversely, that perturbations along vectors in the space $N(A)^\perp = \text{span}\{v_1, \ldots, v_r\}$ can be identified. We would like to translate this result to estimate the identifiability of the unit vectors, that is, the conductances of the currents defining the AP model. In other words, we would like to characterize the identifiability of the maximum conductance of the Na-channels, the Kr-channels, and so on. Clearly, if the perturbation of the conductance vector is completely in the space $N(A)$ or in the space $N(A)^\perp$, the question is simple, but we need to define the identifiability of unit vectors that are partly in both spaces. We will do this by considering the projection of the perturbation to the $N(A)$ space.

Since $\{v_1, \ldots, v_N\}$ is an orthonormal basis, we can expand any perturbation e using this basis $$e = \Sigma_{i=1}^N (e_i, v_i) v_i \quad (22).$$

Furthermore, the projection of this vector onto the space $N(A) = \text{span}\{v_{r+1}, \ldots, v_N\}$ is simply given by $$P_N e = \Sigma_{i=r+1}^N (e_i, v_i) v_i \quad (23).$$

Now, e is the complete vector, $P_{Ne}$ is the part of the vector that cannot be identified, and $e - P_{Ne}$ is the part of the vector that is in the space of identifiable vectors, $N(A)^\perp$. We now define the identifiability index of a vector to be given by $$k(e) = \|e - P_{Ne}\| \quad (24).$$

Here it is useful to note that if $e \in N(A)$, then $e = P_{Ne}$ and $k(e) = 0$. Similarly, if $e \in N(A)^\perp$, then $P_{Ne} = 0$ and $k(e) = 1$. Hence, a completely unidentifiable vector has an identifiability index equal to zero, and a completely identifiable vector has an identifiability index equal to one.

Singular Values Close to Zero

The index above distinguishes between singular values that are positive and those that are identically equal to zero. There is nothing wrong in defining the identifiability index in this way, but in actual computations, the main challenge is posed by singular values that are close to zero. From (21), we see that if the singular value is very small, a perturbation in the direction of the associated singular vector changes the total membrane current very little. Therefore, we would also like to include singular vectors associated with small singular values in the space of non-identifiable vectors. In the numerical experiments below, we specify how we defined which singular values should belong to the identifiable and unidentifiable spaces.

Non-Linear Effects

The basic idea presented above is to consider the transmembrane potential generated by a sum of currents, and then ask the question: What happens if the currents are perturbed? By considering the SVD of the matrix of stored currents, we can give precise answers depending on what kind of perturbations are applied. However, as illustrated in the perturbed model (4), this is a nonlinear process and perturbation of a current will lead the solution into another path and possibly change the currents more fundamentally than just multiplying them by a factor. Only numerical experiments can show how accurate the method is and that will be a major topic of the next section.

Results

In this section we illustrate a few examples of the SVD analysis outlined above. We consider three AP models for human ventricular cardiomyoctes; the ten Tusscher et al. model [24], the Grandi et al. model [25], and the O'Hara et al. model [26]. We investigate the relationship between the size of the singular values and the effect of perturbing the currents by the corresponding singular vectors for these three models. In addition, we compute the identifiability index for the currents of the models.

Note that the method developed here can be used for any model that can be written on the form (5), (6), and the choice of models considered here is therefore somewhat arbitrary.

Figure 12:
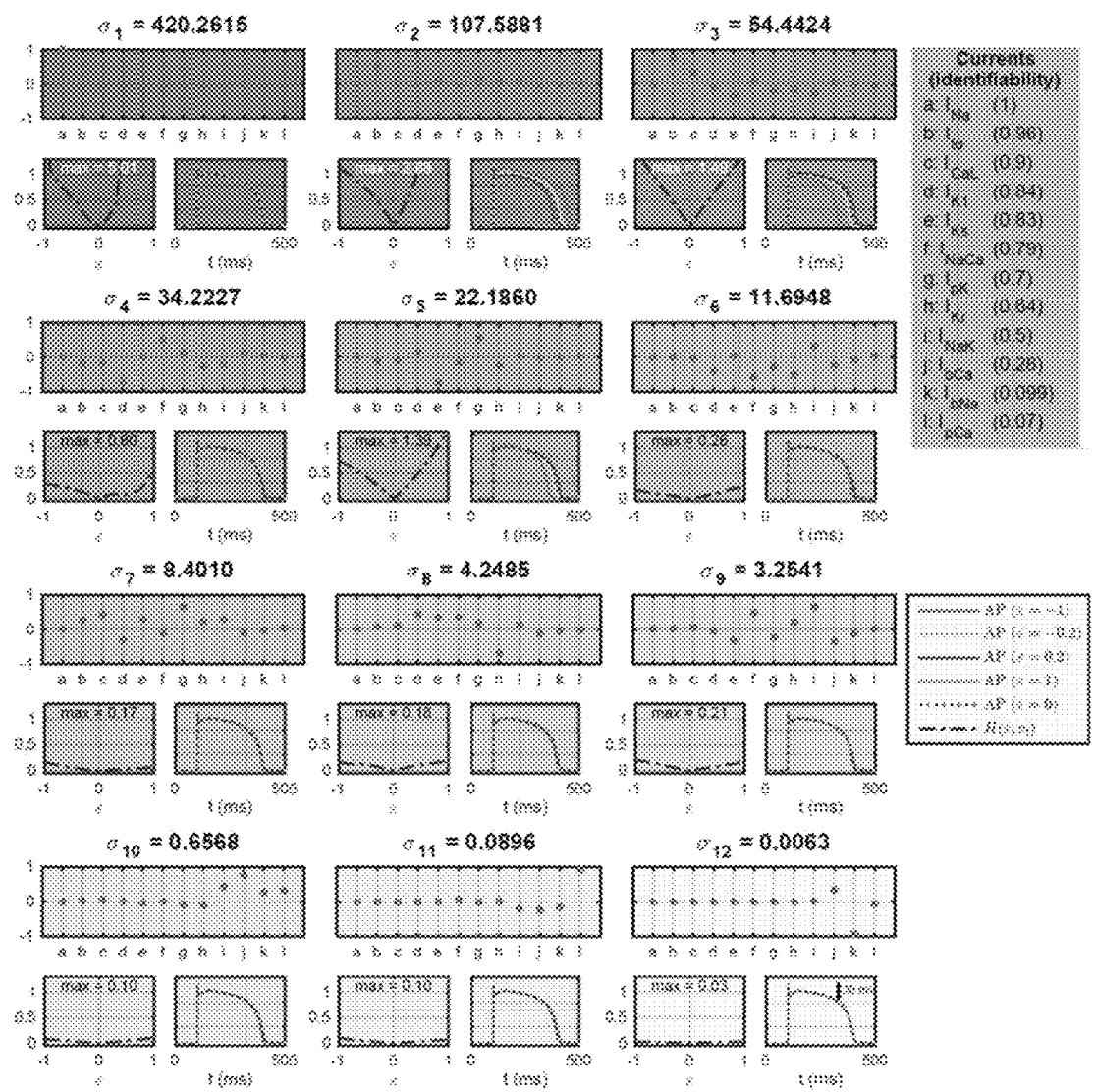
FIG. 12 shows SVD analysis of the currents of the ten Tusscher et al. model [24]. The values σ1, . . . , σ12 are the singular values of the current matrix A defined in (11) in Example 3. The plots directly below the singular values are the singular vectors corresponding to each of the singular values. Each letter corresponds to a single current specified in the panel on the far right. The below plots show how a perturbation of the currents corresponding to the singular vector affects the computed AP of the model. The left plots show the measure $H(ε,v_i)$, defined by (25) in Example 3. The right plots show the computed action potentials for a selection of perturbations. The numbers given after each current in the far right panel indicate the sensitivity index ((24) in Example 3) computed for each of the currents. The null space N(A) is defined by the singular vectors corresponding to the indices defined in (26) in Example 3 with δ=0.25.
Figure 13:
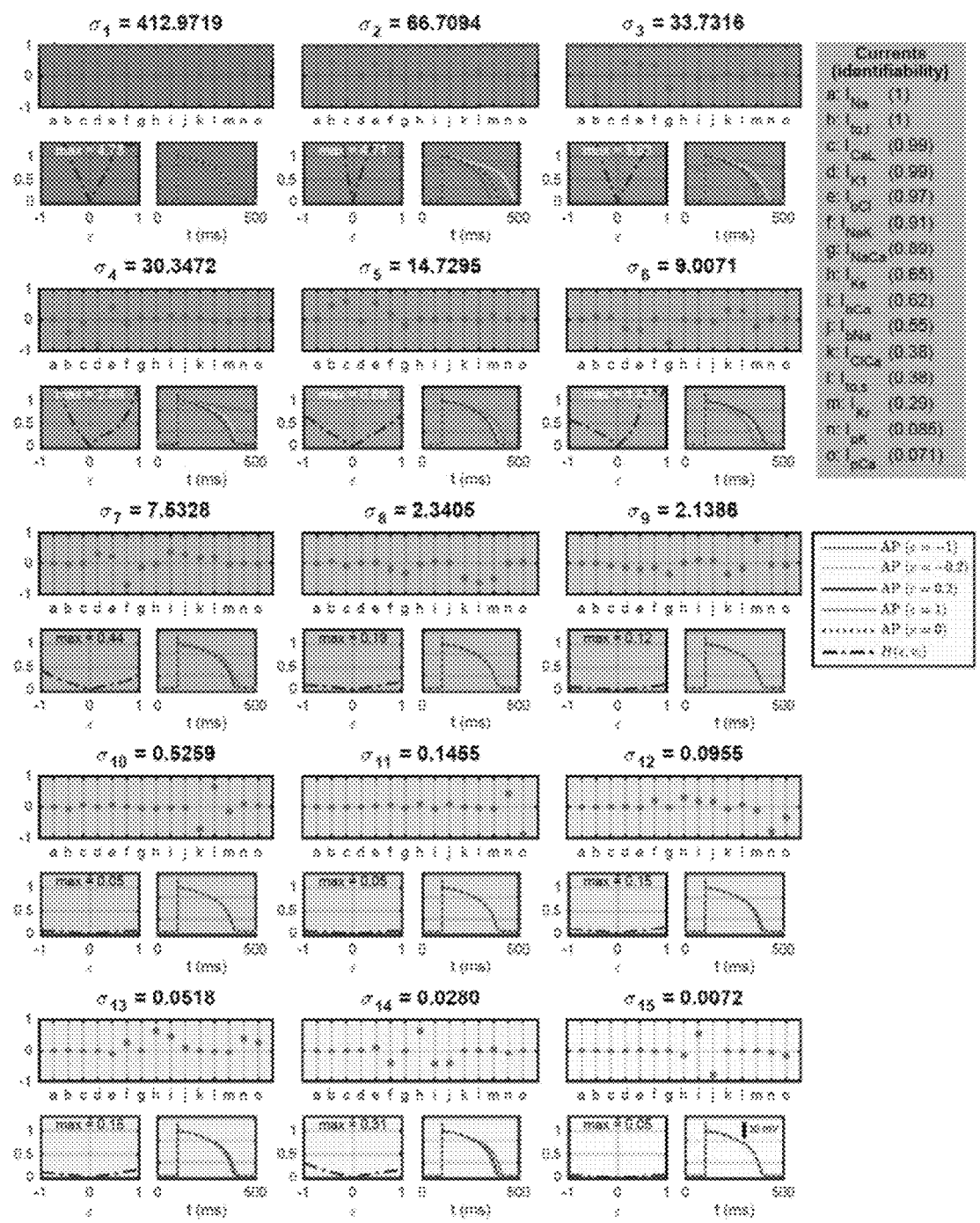
FIG. 13 shows SVD analysis of the currents of the Grandi et al. model [25], following the same structure as FIG. 12.
Figure 14:
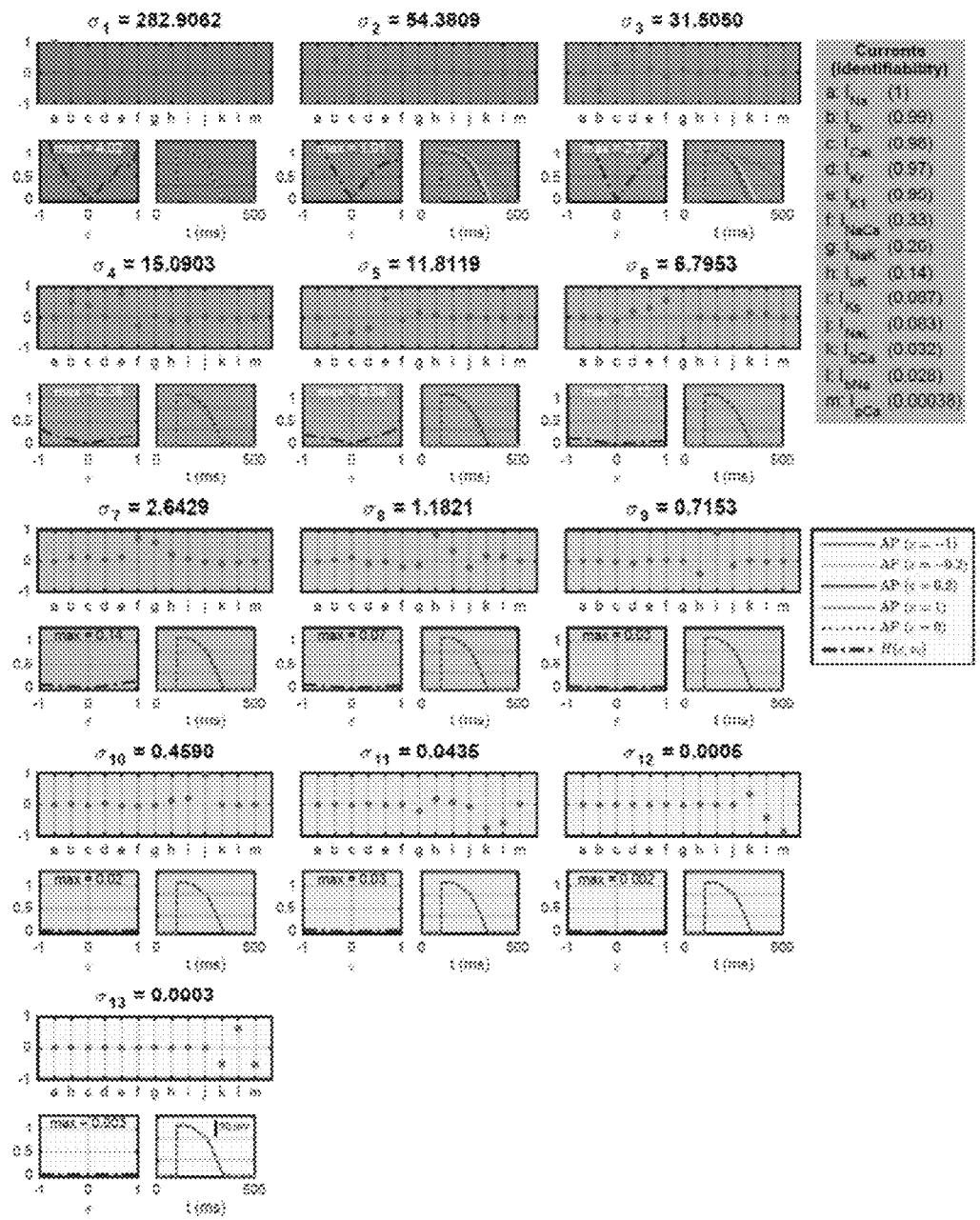
FIG. 14 shows SVD analysis of the currents of the O'Hara et al. model [26], following the same structure as FIG. 12.

Singular Value Decomposition of the Currents in the Ten Tusscher, Grandi, and O'Hara AP Models FIGS. 12, 13, and 14 show the SVD analysis of the currents in the ten Tusscher et al. model [24], the Grandi et al. model [25], and the O'Hara et al. model [26], respectively. We consider the epicardial version of all the AP models. In the construction of the current matrix A (see, (11)), each of the currents of the models are saved for every time step of size $\Delta t = 0.1$ ms between $t=0$ ms and $t=500$ ms.

In the Grandi model, a number of currents ($I_{Na}$, $I_{bNa}$, $I_{NaK}$, $I_{Ks}$, $I_{pK}$, $I_{ClCa}$, $I_{CaL}$, $I_{NaCa}$, $I_{pCa}$, and $I_{bCa}$) are divided into two components, one directed into the junctional cleft and one directed into the subsarcolemmal space. In the analysis in FIG. 13, the currents of each type represent the sum of these two components. Furthermore, both in the Grandi model and in the O'Hara model, the L-type calcium current is divided into three ionic components, a calcium component, a sodium component and a potassium component. In the analysis of FIGS. 13 and 14, the current $I_{CaL}$ is defined as the sum of these three components.

Singular Values and Vectors

FIG. 12 shows the twelve singular values $\sigma_1, \ldots, \sigma_{12}$, of the SVD of the twelve currents in the ten Tusscher model, ordered from the largest value, $\sigma_1=420.26$, to the smallest value, $\sigma_{12}=0.0063$. The plots located directly below each singular value illustrate the corresponding singular vectors. Each letter between "a" and "l" here corresponds to a specific current in the ten Tusscher model, specified in the panel on the far right-hand side.

We observe that the largest singular value, $\sigma_1$, corresponds to a singular vector that is almost equal to the unit vector $e_{Na}$ for the fast sodium current. In addition, the smallest singular value, $\sigma_{12}$, corresponds to a singular vector quite close to the unit vector $e_{bNa}$ for the background sodium current, but also with a small contribution from the background calcium current, $I_{bCa}$.

The Grandi model and the O'Hara model consist of fifteen and thirteen membrane currents, respectively, and FIGS. 13 and 14 similarly show the singular values and corresponding singular vectors for these two models. We observe that for all three models, the largest singular value corresponds to a singular vector almost exclusively associated with the fast sodium current, $I_{Na}$. In addition, we observe that the size of the singular values vary between small values in the range 0.0001-0.01 to large values of about 300-400 for each of the three considered AP models.

Connection Between the Singular Values and the Effect of Perturbations

According to the SVD analysis outlined above, perturbations of the model currents corresponding to large singular values are expected to result in large effects on the total membrane current, $I_T$, and thereby, expectedly, to large effects on the resulting action potential. Conversely, perturbations corresponding to small singular values are expected to result in small effects on the total membrane current and the resulting action potential. This theoretical result relies on simplifying assumptions, and, consequently, it might not hold in actual AP model computations. We therefore wished to investigate whether the expected results about the connection between the size of the singular values and the effect of the perturbation held for the three AP models considered in FIGS. 12-14.

To investigate this, we ran simulations in which each of the model currents were perturbed by the computed singular vectors. More specifically, for each singular vector $v_i$, each of the currents $I_j$ of the model was multiplied by the factor $(1+\varepsilon \cdot v_{i,j})$, where $v_{i,j}$ denotes the j-th element of the singular vector $v_i$, and $\varepsilon$ was varied between $-1$ and $1$. For example, in the case of the first singular value, $\sigma_1$, of the ten Tusscher model (see, FIG. 12), the fast sodium current, $I_{Na}$, was multiplied by a factor close to $(1+\varepsilon)$, while the other currents were almost unperturbed. For the second singular value, $\sigma_2$, $I_{to}$ was multiplied by a factor of approximately $(1+0.5 \cdot 0 \cdot \varepsilon)$, $I_{CaL}$ was multiplied by approximately $(1-0.8 \cdot \varepsilon)$, and the remaining currents were only perturbed by very small factors.

In each of FIGS. 12-14, the left plots below the singular vector plots show a measure, H, of the difference between the computed AP in the default version of the models and the perturbed models for each of the singular values. This H was set up to detect differences in a selection of action potential characteristics and was defined as $$H(\varepsilon, v_i) = \sum_{q=1}^{5} H_q(\varepsilon, v_i), \qquad (25)$$

where $$H_1(\varepsilon, v_i) = \frac{|APD_{20}(v^*) - APD_{20}(\overline{v}(\varepsilon \cdot v_i))|}{|APD_{20}(v^*)|},$$

$$H_2(\varepsilon, v_i) = \frac{|APD_{50}(v^*) - APD_{50}(\overline{v}(\varepsilon \cdot v_i))|}{|APD_{50}(v^*)|},$$

$$H_3(\varepsilon, v_i) = \frac{|APD_{80}(v^*) - APD_{80}(\overline{v}(\varepsilon \cdot v_i))|}{|APD_{80}(v^*)|},$$

$$H_4(\varepsilon, v_i) = \frac{\left|\left(\frac{dv^*}{dt}\right)_{max} - \left(\frac{d\overline{v}(\varepsilon \cdot v_i)}{dt}\right)_{max}\right|}{\left|\left(\frac{dv^*}{dt}\right)_{max}\right|},$$

-continued $$H_5(\varepsilon, v_i) = \frac{\|v^* - \bar{v}(\varepsilon \cdot v_i)\|}{\|v^*\|}.$$

Here, $v^*$ is the transmembrane potential of the default model ($\varepsilon=0$), and $\bar{v}(\varepsilon \cdot v_i)$ is the transmembrane potential of the models for which the currents are perturbed by $\varepsilon \cdot v_i$, where $v_i$ is a singular vector. Furthermore $APD_{20}$, $APD_{50}$, and $APD_{80}$ are the action potential durations (in ms) for 20%, 50%, and 80% repolarization, respectively, $(dv/dt)_{max}$ is the maximal upstroke velocity (in mV/ms), and $\|\cdot\|$ is the Euclidian norm.

A stimulus current was applied in every second of the simulation, and the solutions are recorded in the 20th computed AP after the model change was applied. The text in the upper part of the plots indicates the maximum value of $H(\varepsilon, v_i)$ computed for the considered values of $\varepsilon$, ignoring cases where any of the action potential features of $H_1$–$H_5$ were not possible to compute. Furthermore, the right plots illustrate the computed action potentials for a small selection of $\varepsilon$-values ($\varepsilon = -1, -0.2, 0, 0.2, 1$).

In the plots we observe that, in general, the expected observation that perturbations corresponding to large singular values result in large changes in the AP and that perturbations corresponding to small singular values result in small changes in the AP seems to have held well for each of the three considered AP models. We observe that the effect of a perturbation corresponding to a given singular value was not necessary larger than the effect of a perturbation corresponding to a smaller singular value in all cases, but the largest perturbation effects were observed for the largest singular values, and the small singular values resulted in quite small perturbation effects in most cases.

For the ten Tusscher model, we observe that perturbations corresponding to the singular values $\sigma_7, \ldots, \sigma_{12}$ all resulted in relatively small changes in the computed AP, with values of H below 0.25. Similarly, for the O'Hara model, perturbations corresponding to the singular values $\sigma_6, \ldots, \sigma_{13}$ all resulted in nearly indistinguishable changes in the computed AP. For the Grandi model, perturbations corresponding to $\sigma_8, \ldots, \sigma_{13}$, and $\sigma_{15}$, resulted in very small changes of the computed AP. However, perturbations corresponding to $\sigma_{14}$ gave rise to slightly larger effects, demonstrating that the size of the singular values did not correspond directly to the significance of the computed AP changes. Nevertheless, also in this case, the largest effects on the computed AP were observed for the perturbations corresponding to the largest singular values.

Sensitivity Index for Individual Currents

As observed in FIGS. 12-14, perturbations corresponding to large singular values resulted in large effects of the computed AP, whereas perturbations corresponding to small singular values resulted in relatively small effects on the computed AP. As indicated in the Methods section, we wish to use this knowledge to construct an identifiability index that describes the identifiability of a single current.

In order to compute the identifiability index specified in (24), we need to define which singular vectors are identifiable and which are unidentifiable. In principle, singular vectors associated with strictly positive singular values are identifiable, but this definition is not very useful since none of the computed singular values in the SVD analysis are identically equal to zero and since also very small singular values give rise to very small changes. Therefore, we let the identifiability of a singular vector be determined by the observed changes in the APs resulting from perturbations along that singular vector. In other words, we let the null space N(A) be spanned by the vectors $v_i$ for $i \in S$, where S is defined as $$S = \left\{ i : \max_{-1 \leq \varepsilon \leq 1} H(\varepsilon, v_i) < \delta \right\}, \quad (26)$$

for some threshold value $\delta$.

The identifiability index computed for each of the currents in FIGS. 12-14 for $\delta = 0.25$ are shown in the panel on the far right-hand side of the figures. For the ten Tusscher model, the index indicated that the $I_{Na}$, $I_{to}$, and $I_{caL}$ currents are highly identifiable, but that the currents $I_{bCa}$, $I_{bNa}$, and $I_{pCa}$ are largely unidentifiable. For the Grandi model, the identifiability index indicateded that $I_{Na}$, $I_{to,f}$, $I_{caL}$, $I_{K1}$, $I_{bCl}$, $I_{NaK}$, and $I_{NaCa}$ are highly identifiable and that $I_{ClCa}$, $I_{to,s}$, $I_{Kr}$, $I_{pK}$, and $I_{pCa}$ are largely unidentifiable. Similarly, the index indicated that the $I_{Na}$, $I_{to}$, $I_{CaL}$, $I_{Kr}$, and $I_{K1}$ currents are highly identifiable in the O'Hara model, but that the remaining currents to a large extent are unidentifiable.

Discussion

It is important to understand the uncertainty of the parameters in AP models. An overview of related problems involved in AP models of cardiac cells is given by Johnstone et al. [27]. One of the problems highlighted in the paper is that there are unidentifiable parameters in the AP model—multiple parameter sets fit the data equally well and the individual conductances cannot be identified. Here, we have developed a method for investigating the identifiability of the maximum conductances of ion channels in a model, when the model is parameterized to fit a single action potential waveform. Simulations of the AP model give the total membrane currents and the individual ion currents. Then, by storing the currents in a matrix, the SVD method can be used to analyze what combinations of currents will be largely invisible in the overall waveform. We have developed an identifiability index that uses this information to quantify how identifiable the individual currents are. Although the method is based on linear analysis of a highly nonlinear problem, the method gives valuable insight that is difficult to obtain by other methods.

Perturbation Effects

In FIGS. 12-14, we observed that large singular values were associated with large perturbation effects along their corresponding singular vectors, while small singular values were to a large degree associated with small perturbation effects, as predicted by the linear theoretical considerations outlined in the Methods section. The nonlinear perturbation effects were considered by the use of a measure H defined in (25) (lower left plots) to detect differences in the perturbed AP waveform, and in many cases, the trends of H could be readily seen by simply visually inspecting the APs resulting from the perturbations (lower right plots).

Figure 15:
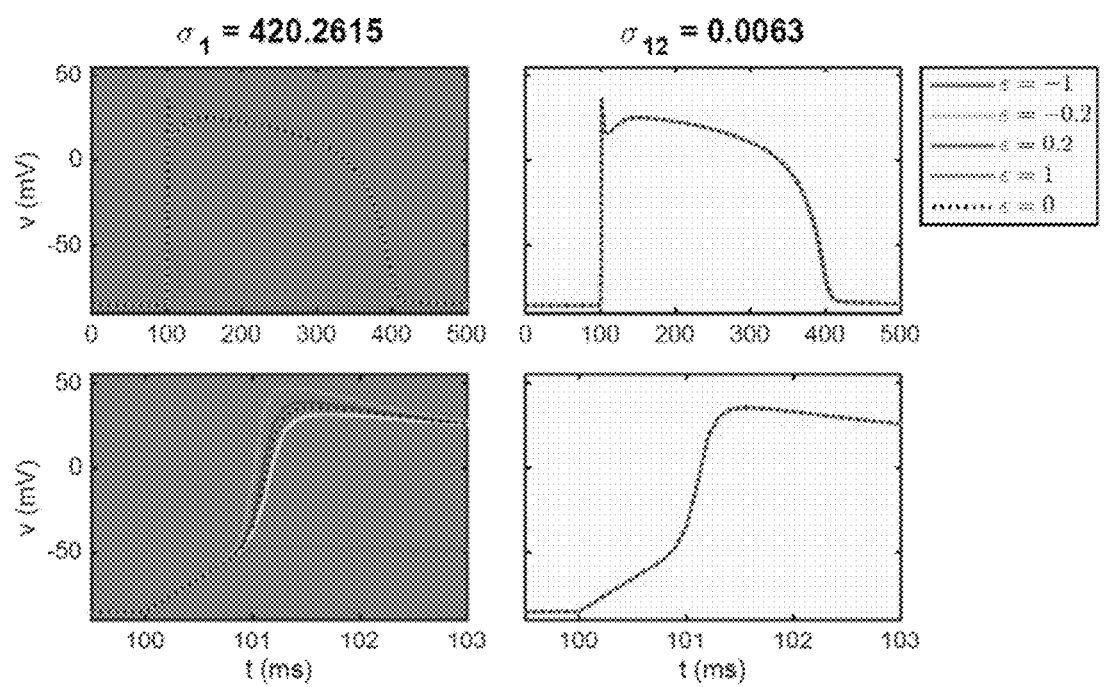
FIG. 15 shows the effect on the transmembrane potential of perturbing the currents corresponding to the largest singular value, σ1, and the smallest singular value, σ12, of the SVD analysis of the ten Tusscher et al. model (see FIG. 12). The upper panel shows the full action potential, and the lower panel focuses only on the upstroke.

In some cases, however, the perturbations produced large values of H even though the perturbed APs seemed to be visually identical. The reason why in these cases H measured large differences was that H includes a term that measures the effect on the maximal upstroke velocity. This effect is hard to observe in the plots of the AP due to the time scale, but the effect is illustrated for two examples from the ten Tusscher model in the lower panel of FIG. 15. Here, we show the upstroke of the AP for perturbations along the singular vectors corresponding to the largest singular value (left) and the smallest singular value (right) of the SVD analysis. For the large singular value, $\sigma_1$, we observed large changes in the upstroke dynamics, which corresponded to the large values of H observed in FIG. 12. For the smallest singular value, $\sigma_{12}$, on the other hand, the effects of the perturbations on the upstroke were completely indistinguishable, corresponding to the small values of H observed in FIG. 12.

Uniqueness of Model Parameters

A key question in deriving and applying AP models is the uniqueness of the parameters. For Markov Models used to represent the open probability of ion channels, this problem was carefully studied by Fink and Noble [28] who found parameter unidentifiability in 9 out of 13 models. Lack of uniqueness has also been observed for models of the AP of neurons; see, e.g., [29, 30, 31] and for AP models of cardiomyocytes; see, e.g., [32, 33, 34, 35]. The most common way of investigating the sensitivity of AP models is to perturb individual currents and look for the effect. This method is useful in the sense that it indicates how well blocking of individual currents can be identified using the model. Suppose, for instance, that the AP model is very sensitive to changes in the sodium current. Then, if a sodium blocker is applied, such changes will be observed and thus the effect of a sodium blocker can be identified. But this approach will not uncover the identifiability of more subtle effects where a blocker affects many currents simultaneously. The numerical examples presented above show that very few ion currents can be completely identified by observing the total membrane currents. According to the identifiability index, less than 50% of the perturbations can be observed for 3 out of 12 ion currents in the ten Tusscher et al. model, 5 out of 15 ion currents in the model of Grandi et al., and 8 out of 13 ion currents in the O'Hara et al. model. This indicates a considerable degree of redundancy in the models in their ability to produce a single paced action potential.

Model Reduction

Several authors have used redundancy of AP models to derive reduced models. For instance, in both [36] and [37], the authors used redundancy of the AP models to systematically reduce complex models to obtain simpler models. Other authors have developed parsimonious models by only including major currents; see, e.g., [38, 39, 40, 41]. A comprehensive overview of models of the cardiac AP is given in [9], where models ranging from 2 to 67 variables are presented.

Linear Sensitivity Analysis

Over the past decade, a series of papers by Sobie and co-authors (see, [42, 43, 44, 45]) have developed a theory describing a strong correlation between model parameters like the maximum conductances of the ion channels and output variables like the APD. These relations are surprising given the strong nonlinearities involved in the AP models, but the relations are also very useful, in particular in order to understand the behavior of populations of models. We have used the fact that linear models seem to pick up important features of nonlinear AP models to devise a method for analyzing how the total transmembrane current changes under perturbations of the individual ion currents using the SVD algorithm.

CONCLUSION

We have presented a method for investigating the uniqueness of parameters of commonly used mathematical models of action potentials. The method is simple to implement and the results are interpreted in a straightforward manner. For three well-known models of human cardiac cells, the method revealed that significant changes in the maximum conductances can be introduced without any appreciable change in the resulting action potential. The method uses the singular value decomposition to find perturbations that give minimal changes in the solution. Such perturbations are impossible to find by simply changing the individual conductances, and the search space is very large if one were to search for combinations of changed conductances that give little effect on the action potential. The method is applicable for any model written on the standard form for action potential models; see, equations (5) and (6).

REFERENCES

[1] Freeman Dyson. A meeting with Enrico Fermi. Nature, 427(6972):297, 2004.

[2] A L Hodgkin and A F Huxley. The components of membrane conductance in the giant axon of loligo. The Journal of physiology, 116(4):473-496, 1952.

[3] Denis Noble. A modification of the HodgkinHuxley equations applicable to Purkinje fibre action and pacemaker potentials. The Journal of Physiology, 160(2):317-352, 1962.

[4] CellML Model Repository. www.cellml.org/models/.

[5] G. Bard Ermentrout and David H. Terman. Mathematical Foundations of Neuroscience, volume 35. Springer-Verlag, New York, 2010.

[6] David Sterratt, Bruce Graham, Andrew Gillies, and David Willshaw. Principles of Computational Modelling in Neuroscience. Cambridge University Press, 2011.

[7] Robert Plonsey and Roger C. Barr. Bioelectricity, A Quantitative Approach. Springer, 2007.

[8] James P. Keener and James Sneyd. Mathematical Physiology. Springer, 2009.

[9] F. H Fenton and E. M. Cherry. Models of cardiac cell. Scholarpedia, 3(8):1868, 2008. revision #91508.

[10] Zhilin Qu, Gang Hu, Alan Garfinkel, and James N Weiss. Nonlinear and stochastic dynamics in the heart. Physics Reports, 543(2), 2014.

[11] Yoram Rudy and Jonathan R Silva. Computational biology in the study of cardiac ion channels and cell electrophysiology. Quarterly Reviews of Biophysics, 39(01):57-116, 2006.

[12] Yoram Rudy. From genes and molecules to organs and organisms: Heart. Comprehensive Biophysics, pages 268-327, 2012.

[13] Andrew G Edwards and William E Louch. Species-dependent mechanisms of cardiac arrhythmia: a cellular focus. Clinical Medicine Insights: Cardiology, 11:1179546816686061, 2017.

[14] S. A. Niederer, M. Fink, D. Noble, and N. P. Smith. A meta-analysis of cardiac electrophysiology computational models. Experimental Physiology, 94(5):486-495, 5 2009.

[15] Steven D Girouard, Kenneth R. Laurita, and David S Rosenbaum. Unique properties of cardiac action potentials recorded with voltage-sensitive dyes. Journal of cardiovascular electrophysiology, 7(11): 1024-1038, 1996.

[16] Marco Canepari, Dej an Zecevic, Olivier Bernus, et al. Membrane Potential Imaging in the Nervous System and Heart. Springer, 2015.

[17] Ksenia Blinova, Jayna Stohlman, Jose Vicente, Dulciana Chan, Lars Jo-hannesen, Maria P. Hortigon-Vinagre, Victor Zamora, Godfrey Smith, William J. Crumb, Li Pang, Beverly Lyn-Cook, James Ross, Mathew Brock, Stacie Chvatal, Daniel Millard, Loriano Galeotti, Norman Stock-bridge, and David G. Strauss. Comprehensive translational assessment of human-induced pluripotent stem cell derived cardiomyocytes for evaluating drug-induced arrhythmias. Toxicological Sciences, 155(1):234-247, 2017.

[18] Aslak Tveito, Karoline Horgmo Jæger, Nathaniel Huebsch, Berenice Charrez, Andrew G Edwards, Samuel Wall, and Kevin E Healy. Inversion and computational maturation of drug response using human stem cell derived cardiomyocytes in microphysiological systems. Scientific reports, 8(1):17626, 2018.

[19] J'org Liesen and Volker Mehrmann. Linear Algebra in Every Day Life. Springer, 2015.

[20] Tom Lyche. Numerical Linear Algebra and Matrix Factorizations. University of Oslo, lecture notes, 201t.

[21] Michelangelo Paci, Jari Hyttinen, Blanca Rodriguez, and Stefano Severi. Human induced pluripotent stem cell-derived versus adult cardiomyocytes: an in silico electrophysiological study on effects of ionic current block. British journal of pharmacology, 172(21):5147-5160, 2015.

[22] Michelangelo Paci, Elisa Passini, Stefano Severi, Jari Hyttinen, and Blanca Rodriguez. Phenotypic variability in LQT3 human induced pluripotent stem cell-derived cardiomyocytes and their response to anti-arrhythmic pharmacological therapy: an in silico approach. Heart Rhythm, 2017.

[23] Beatriz Carbonell-Pascual, Eduardo Godoy, Ana Ferrer, Lucia Romero, and Jose M Ferrero. Comparison between Hodgkin-Huxley and Markov formulations of cardiac ion channels. Journal of theoretical biology, 399:92-102, 2016.

[24] Kirsten H W J Ten Tusscher and Alexander V Panfilov. Alternans and spiral breakup in a human ventricular tissue model. American Journal of Physiology-Heart and Circulatory Physiology, 291(3):H1088H1100, 2006.

[25] Eleonora Grandi, Francesco S. Pasqualini, and Donald M. Bers. A novel computational model of the human ventricular action potential and Ca transient. Journal of Molecular and Cellular Cardiology, 48(1):112-121, 2010.

[26] Thomas O'Hara, L'aszlo Vir'ag, Andr'as Varr'o, and Yoram Rudy. Simulation of the undiseased human cardiac ventricular action potential: Model formulation and experimental validation. PLoS Computational Biology, 7(5):e1002061, 2011.

[27] Ross H Johnstone, Eugene T Y Chang, R'emi Bardenet, Teun P De Boer, David J Gavaghan, Pras Pathmanathan, Richard H Clayton, and Gary R Mirams. Uncertainty and variability in models of the cardiac action poten-tial: Can we build trustworthy models? Journal of molecular and cellular cardiology, 96:49-62, 2016.

[28] Martin Fink and Denis Noble. Markov models for ion channels: Versatility versus identifiability and speed. Philosophical Transactions of the Royal Society A: Mathematical, Physical and Engineering Sciences, 367(1896): 2161-2179, 2009.

[29] Eve Marder and Adam L Taylor. Multiple models to capture the variability in biological neurons and networks. Nature neuroscience, 14(2):133, 2011.

[30] Astrid A Prinz, Dirk Bucher, and Eve Marder. Similar network activity from disparate circuit parameters. Nature neuroscience, 7(12):1345, 2004.

[31] Pablo Achard and Erik De Schutter. Complex parameter landscape for a complex neuron model. PLoS computational biology, 2(7):e94, 2006.

[32] Amrita X Sarkar and Eric A Sobie. Regression analysis for constraining free parameters in electrophysiological models of cardiac cells. PLoS computational biology, 6(9):e1000914, 2010.

[33] Stefan A Mann, Mohammad Imtiaz, Annika Winbo, Annika Rydberg, Matthew D Perry, Jean-Philippe Couderc, Bronislava Polonsky, Scott Mc-Nitt, Wojciech Zareba, Adam P Hill, et al. Convergence of models of human ventricular myocyte electrophysiology after global optimization to recapitulate clinical long QT phenotypes. Journal of molecular and cellular cardiology, 100:25-34, 2016.

[34] Socrates Dokos and Nigel H Lovell. Parameter estimation in cardiac ionic models. Progress in biophysics and molecular biology, 85(2-3):407-431, 2004.

[35] Jaspreet Kaur, Anders Nygren, and Edward J Vigmond. Fitting membrane resistance along with action potential shape in cardiac myocytes improves convergence: application of a multi-objective parallel genetic algorithm. PLoS One, 9(9):e107984, 2014.

[36] Marco Arieli Herrera-Valdez and Joceline Lega. Reduced models for the pacemaker dynamics of cardiac cells. Journal of Theoretical Biology, 270(1):164-176, February 2011.

[37] Daniel M Lombardo and Wouter-Jan Rappel. Systematic reduction of a detailed atrial myocyte model. Chaos: An Interdisciplinary Journal of Nonlinear Science, 27(9): 093914, 2017.

[38] Rubin R Aliev and Alexander V Panfilov. A simple two-variable model of cardiac excitation. Chaos, Solitons & Fractals, 7(3):293-301, 1996.

[39] Flavio Fenton and Alain Karma. Vortex dynamics in three-dimensional continuous myocardium with fiber rotation: Filament instability and fibrillation. Chaos: An Interdisciplinary Journal of Nonlinear Science, 8(1):20-47, 1998.

[40] Suran K Galappaththige, Richard A Gray, and Bradley J Roth. Cardiac strength-interval curves calculated using a bidomain tissue with a parsimonious ionic current. PloS one, 12(2):e0171144, 2017.

[41] Richard A Gray and Pras Pathmanathan. A parsimonious model of the rabbit action potential elucidates the minimal physiological requirements for alternans and spiral wave breakup. PLoS computational biology, 12(10):e1005087, 2016.

[42] Eric A Sobie. Parameter sensitivity analysis in electrophysiological models using multivariable regression. Biophysical journal, 96(4):1264-1274, 2009.

[43] Amrita X Sarkar and Eric A Sobie. Quantification of repolarization reserve to understand interpatient variability in the response to proarrhythmic drugs: a computational analysis. Heart Rhythm, 8(11):1749-1755, 2011.

[44] Amrita X Sarkar, David J Christini, and Eric A Sobie. Exploiting mathematical models to illuminate electrophysiological variability between individuals. The Journal of physiology, 590(11):2555-2567, 2012.

[45] Jingqi Q X Gong and Eric A Sobie. Population-based mechanistic modeling allows for quantitative predictions of drug responses across cell types. NPJ systems biology and applications, 4(1):11, 2018.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for administering a drug to a patient after measuring an effect of the drug on immature CM, the method comprising:
(a) obtaining one or more first measurements of transmembrane voltage (Vm) and/or one or more first measurements of intracellular calcium concentration (Cai) in a control immature CM;
(b) storing, in memory of a computer system, data representing said one or more first measurements of Vm in vector vC and/or storing data representing said one or more first measurements of Cai in vector cC;
(c) contacting the immature CM with a composition comprising a sufficient amount of the drug to produce a drug-treated immature CM;
(d) obtaining one or more second measurements of Vm and/or one or more second measurements of Cai in the drug-treated immature CM;
(e) storing, in the memory of the computer system, data representing said one or more second measurements of Vm in vector vD and/or storing data representing said one or more second measurements of Cai in vector cD;
(f) inverting the data stored in vC and/or cC to update one or more parameters in an immature base CM model, stored in vector pIM,B, to yield vector pIM,C that parameterizes an immature control CM model;
(g) inverting the data stored in vD and/or cD to update one or more parameters stored in vector pIM,C to yield vector pIM,D that parameterizes an immature drug-treated CM model;
(h) updating one or more values in a diagonal maturation matrix Q such that the equality QpIM,C=pM is satisfied, wherein pM is a vector that parameterizes a mature base CM model and wherein before Q is updated, Q satisfies the equality pM=QpIM,B;
(i) multiplying pIM,D by Q to generate vector pM,D, wherein pM,D parameterizes a mature drug-treated CM model;
storing, in the memory of the computer system, the mature base CM model and the mature drug-treated CM model;
(j) using, by the computer system, the mature base CM model and the mature drug-treated CM model to generate a simulated mature control action potential (AP) and a simulated mature drug-treated AP, respectively;
(k) comparing one or more morphological properties of the simulated mature control AP and the simulated mature drug-treated AP in order to calculate a difference, thereby determining the effect of the drug, wherein the effect of the drug is anti-arrhythmic; and
(l) administering the drug to the patient based on the determined effect of the drug, wherein the drug is an anti-arrhythmic drug.

2. The method of claim 1, wherein the one or more parameters represent the number of one or more proteins in the immature base CM model, dynamics of one or more proteins in the immature base CM model, cell volume in the immature base CM model, cell surface area in the immature base CM model, cell membrane capacitance in the immature base CM model, or a combination thereof.

3. The method of claim 2, wherein the one or more proteins are selected from the group consisting of an ion channel, an ion exchanger, an ion pump, and a combination thereof.

4. The method of claim 1, wherein the one or more parameters represent the maximum conductance of an ion channel or the maximum rate of an ion exchanger or ion pump.

5. The method of claim 1, wherein inverting the data comprises minimizing a cost function.

6. The method of claim 5, wherein minimizing the cost function comprises minimizing differences between a characteristic determined in an experimentally-observed AP or calcium transient and the corresponding characteristic in an AP or calcium transient generated by the immature base CM model or the immature control CM model;
wherein the characteristic is selected from the group consisting of Vm, APDV,n, APDCa,n, maximum upstroke velocity of the intracellular calcium concentration (Cai), and a combination thereof; and
wherein APDV,n and APDCa,n, are a duration of the transmembrane voltage (Vm) and calcium transients, respectively, wherein each value of n is independently selected and represents a percentage of the maximum Vm value.

7. The method of claim 5, wherein the cost function is iteratively minimized.

8. The method of claim 1, wherein when vD or cD are inverted, the effect of the drug is that of reducing the maximum conductance of an ion channel or the maximum rate of an ion pump or ion exchanger.

9. The method of claim 1, wherein multiplying a vector p by Q changes the number of one or more proteins, a cell volume, and/or a cell surface area in the mature base CM model that is parameterized by p.

10. The method of claim 1, wherein a fluorescent indicator or dye is used to measure Vm and/or Cai.

11. The method of claim 1, wherein the one or more morphological properties are selected from the group consisting of APDV,n, APDCa,n, maximum Vm upstroke velocity ((dv/dt)max), resting membrane potential, maximum Cai upstroke velocity ((dc/dt)max), peak Cai, and a combination thereof;
wherein APDV,n and APDCa,n, are a duration of the Vm action potential and calcium transients, respectively; and wherein each value of n is independently selected and represents a percentage of the maximum Vm value.

12. A method for administering a drug to a patient, wherein the drug does not have a proarrhythmic effect on a mature cardiomyocyte (CM), the method comprising:
(a) obtaining one or more first measurements of transmembrane voltage (Vm) and/or one or more first measurements of intracellular calcium concentration (Cai) in a control immature CM;
(b) storing, in memory of a computer system, data representing said one or more first measurements of Vm in vector vC and/or storing data representing said one or more first measurements of Cai in vector cC;
(c) contacting the immature CM with a composition comprising a sufficient amount of the drug to produce a drug-treated immature CM;
(d) obtaining one or more second measurements of Vm and/or one or more second measurements of Cai in the drug-treated immature CM;
(e) storing, in the memory of the computer system, data representing said one or more second measurements of Vm in vector vD and/or storing data representing said one or more second measurements of Cai in vector cD;
inverting the data stored in vC and/or cC to update one or more parameters in an immature base CM model, stored in vector pIM,B, to yield vector pIM,C that parameterizes an immature control CM model;

(g) inverting the data stored in vD and/or cD to update one or more parameters stored in vector pIM,C to yield vector pIM,D that parameterizes an immature drug-treated CM model;

(h) updating one or more values in a diagonal maturation matrix Q such that the equality QpIM,C=pM is satisfied, wherein pM is a vector that parameterizes a mature base CM model and wherein before Q is updated, Q satisfies the equality pM=QpIM,B;

(i) multiplying pIM,D by Q to generate vector pM,D, wherein pM,D parameterizes a mature drug-treated CM model;

storing, in the memory of the computer system, the mature base CM model and the mature drug-treated CM model;

(j) using, by the computer system, the mature base CM model and the mature drug-treated CM model to generate a simulated mature control action potential (AP) and a simulated mature drug-treated AP, respectively;

(k) comparing a morphological property of the simulated mature control AP to the morphological property of the simulated mature drug-treated AP in order to calculate a difference; and (l) based upon the difference in the morphological property between the simulated mature control and drug-treated APs, determining that the drug does not have the proarrhythmic effect and selecting the drug; and (m) administering the drug to the patient, wherein the drug is an anti-arrhythmic drug.

13. The method of claim 12, wherein the immature CM is derived from a cell obtained from the subject patient.

14. The method of claim 12, wherein the immature CM is an induced pluripotent stem cell-derived cardiomyocyte (iPSC-CM).

15. The method of claim 12, wherein the morphological property is selected from the group consisting of $APDV,n$, $APDCa,n$, maximum Vm upstroke velocity ($(dv/dt)max$), resting membrane potential, maximum Cai upstroke velocity ($(dc/dt)max$), peak Cai, and a combination thereof;

wherein $APDV,n$ and $APDCa,n$, are a duration of the Vm action potential and calcium transients, respectively; and wherein each value of n is independently selected and represents a percentage of the maximum Vm value.

16. The method of claim 12, wherein the drug is selected when the morphological property in the simulated mature control AP is less than about 3-fold lower or higher compared to the morphological property in the simulated mature drug-treated AP.

17. The method of claim 12, wherein the one or more parameters represent the number of one or more proteins in the immature base CM model, dynamics of one or more proteins in the immature base CM model, cell volume in the immature base CM model, cell surface area in the immature base CM model, cell membrane capacitance in the immature base CM model, or a combination thereof.

18. The method of claim 17, wherein the one or more proteins are selected from the group consisting of an ion channel, an ion exchanger, an ion pump, and a combination thereof.

19. The method of claim 12, wherein the one or more parameters represent the maximum conductance of an ion channel or the maximum rate of an ion exchanger or ion pump.

20. The method of claim 12, wherein inverting the data comprises minimizing a cost function.

21. The method of claim 20, wherein minimizing the cost function comprises minimizing the differences between a characteristic determined in an experimentally-observed AP or calcium transient and the corresponding characteristic in an AP or calcium transient generated by the immature base CM model or the immature control CM model;

wherein the characteristic is selected from the group consisting of Vm, $APDV,n$, $APDCa,n$, maximum upstroke velocity of the intracellular calcium concentration (Cai), and a combination thereof; and wherein $APDV,n$ and $APDCa,n$, are a duration of the transmembrane voltage Vm and calcium transients, respectively, wherein each value of n is independently selected and represents a percentage of the maximum Vm value.

22. The method of claim 20, wherein the cost function is iteratively minimized.

23. The method of claim 12, wherein when vD or cD are inverted, the effect of the drug is that of reducing the maximum conductance of an ion channel or the maximum rate of an ion pump or ion exchanger.

24. The method of claim 12, wherein multiplying a vector p by Q changes the number of one or more proteins, a cell volume, and/or a cell surface area in the mature base CM model that is parameterized by p.

25. The method of claim 12, wherein a fluorescent indicator or dye is used to measure Vm and/or Cai.

* * * * *